(12) United States Patent
Kawabe et al.

(10) Patent No.: US 6,995,135 B2
(45) Date of Patent: Feb. 7, 2006

(54) PEPTIDES AND PEPTIDOMIMETICS HAVING ANTI-PROLIFERATIVE ACTIVITY AND/OR THAT AUGMENT NUCLEIC ACID DAMAGING AGENTS OR TREATMENTS

(75) Inventors: Takumi Kawabe, Numazu (JP); Hidetaka Kobayashi, Shizuoka (JP)

(73) Assignee: CanBas Co., Ltd., Numazu (JP)

( * ) Notice: Subject to any disclaimer, the term of this patent is extended or adjusted under 35 U.S.C. 154(b) by 0 days.

(21) Appl. No.: 10/347,145

(22) Filed: Jan. 17, 2003

(65) Prior Publication Data

US 2004/0248783 A1 Dec. 9, 2004

Related U.S. Application Data

(60) Provisional application No. 60/350,208, filed on Jan. 17, 2002.

(51) Int. Cl.
*A01N 37/18* (2006.01)
*A61K 38/00* (2006.01)

(52) U.S. Cl. .......................... 514/2; 930/20

(58) Field of Classification Search ................... 514/2; 930/20
See application file for complete search history.

(56) References Cited

FOREIGN PATENT DOCUMENTS

| WO | 01/21771 | 3/2001 |
|---|---|---|
| WO | 01/94411 | 12/2001 |

OTHER PUBLICATIONS

Suganuma et al., "Sensitization of Cancer Cells to DNA Damage-induced Cell Death by Specific Cell Cycle $G_2$ Checkpoint Abrogation", *Cancer Research*, Dec. 1, 1999; 59:5887-5891; XP002181645.

Kobayashi et al., "Selective Cancer Cell Killing by a Novel G2 Checkpoint Abrogating Peptide", Proceedings of the Annual Meeting of the American Assocation for Cancer Research, Mar. 2001; #4892 p. 911, XP-001173131.

Ito et al., "Phylogenetic Relationships of Amaryllidaceae Based on matK Sequence Data", *J. Plant Res.*, Jun. 1999; 112(1106):207-216, XP008027543.

Hayakawa et al., "Sequence Analysis of the *Xestia c-nigrum* Granulovirus Genome", *Virology*, Sep. 30, 1999; 262(2): 277-297, XP004439794.

Nestor et al., "Luteinizing Hormone-Releasing Hormone Antagonists Containing Very Hydrophobic Amino Acids", *J. Med. Chem.*, 1984; 27:1170-1174, XP002288202.

Maryanoff et al., "Protease-Activated Receptor-2 (PAR-2): Structure-Function Study of Receptor Activation by Diverse Peptides Related to Tethered-Ligand Epitopes", *Archives of Biochemistry and Biophysics*, Feb. 15, 2001; 386(2):195-204, XP002971306.

*Primary Examiner*—Bruce R. Campell
*Assistant Examiner*—Jennifer Ione Harle
(74) *Attorney, Agent, or Firm*—Pillsbury Winthrop Shaw Pittman LLP

(57) ABSTRACT

This invention provides compounds including peptides and peptidomimetics that can be used to treat cell proliferative disorders, such as those associated with benign and malignant tumor cells. While the invention is not limited to any particular mechanism, the compounds of the invention appear to function at least in part by inhibiting G2 cell cycle checkpoint. Thus, invention compounds can be used to inhibit cell growth alone or be used in combination with a nucleic acid damaging treatment to inhibit cell growth.

40 Claims, 9 Drawing Sheets

SEQUENCE LISTING

```
<160> NUMBER OF SEQ ID NOS: 139

<210> SEQ ID NO 1
<211> LENGTH: 6
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<220> FEATURE:
<223> OTHER INFORMATION: Xaa is any amino acid with one or two
      aromatic,piperidine,pyrazine,pyrimidine,piperazine,morpholine,pyr
      imidine group(s),indole,pentalene,indene,naphthalene,benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is Bpa,Phe4NO2,any one amino acid,Tyr,Phe
      or nothing

<400> SEQUENCE: 1

Xaa Xaa Xaa Xaa Xaa Xaa
```

-continued

```
<210> SEQ ID NO 2
<211> LENGTH: 6
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Bpa,Phe4NO2,any one amino acid,Tyr,Phe
      or nothing
<220> FEATURE:
<221> NAME/KEY: MOD_RES
<222> LOCATION: (2)
<223> OTHER INFORMATION: Xaa is any amino acid or absent
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is  any amino acid or absent
<220> FEATURE:
<221> NAME/KEY: MOD_RES
<222> LOCATION: (5)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<220> FEATURE:
<223> OTHER INFORMATION: Xaa is any amino acid with one or two
      aromatic,piperidine,pyrazine,pyrimidine,
      piperazine,morpholine,pyrimidine
      group(s),indole,pentalene,indene,naphthalene,benzofuran,
<220> FEATURE:
<223> OTHER INFORMATION: benzothiophene, quinoline,indoline,chroman,
      quinoxaline or quinazoline group in the side chain
<220> FEATURE:
<221> NAME/KEY: MOD_RES
<222> LOCATION: (6)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,benzothiophene,
<220> FEATURE:
<223> OTHER INFORMATION: quinoline,indoline,chroman,quinoxaline or
      quinazoline group in the side chain

<400> SEQUENCE: 2

Xaa Xaa Xaa Xaa Xaa Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
```

```
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is Bpa,Phe4NO2,any one amino acid,Tyr or
      Phe

<400> SEQUENCE: 3 xaa Xaa Xaa Xaa Xaa Xaa
1               5

<210> SEQ ID NO 4
<211> LENGTH: 6
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Bpa,Phe4NO2,any one amino acid,Tyr or
      Phe
<220> FEATURE:
<221> NAME/KEY: MOD_RES
<222> LOCATION: (2)
<223> OTHER INFORMATION: Xaa is any amino acid or absent
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is Cha,Nal(2),(Phe-2,3,4,5,6-F),(Phe-3,4,
      5F),(Phe-4CF3)or an amino acid that occupies a similar side chain
      space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
```

```
<221> NAME/KEY: MOD_RES
<222> LOCATION: (6)
<223> OTHER INFORMATION: Xaa is Cha,Nal(2),(Phe-2,3,4,5,6-F),(Phe-3,4,
      5F),(Phe-4CF3),Bpa,Phe4NO2 oran amino acid that occupies a similar
      side chain space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain

<400> SEQUENCE: 4

Xaa Xaa Xaa Xaa Xaa Xaa
1               5

<210> SEQ ID NO 5
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3),Bpa,Phe4NO2 or any amino acid that occupies a
      similar side chain space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<223> OTHER INFORMATION: Xaa is any amino acid with one or two
      aromatic,piperidine,pyrazine,pyrimidine,
      piperazine,morpholine,pyrimidine
      group(s),indole,pentalene,indene,naphthalene,benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is Bpa,Phe4NO2,anyone amino acid,Tyr or Phe
<220> FEATURE:
<221> NAME/KEY: MOD_RES
<222> LOCATION: (7)
<223> OTHER INFORMATION: Xaa is amino acid or absent
<220> FEATURE:
<221> NAME/KEY: MOD_RES
<222> LOCATION: (8)
<223> OTHER INFORMATION: Xaa is amino acid or absent
<220> FEATURE:
<221> NAME/KEY: MOD_RES
```

```
<222> LOCATION: (9)
<223> OTHER INFORMATION: Xaa is amino acid or absent
<220> FEATURE:
<221> NAME/KEY: MOD_RES
<222> LOCATION: (10)
<223> OTHER INFORMATION: Xaa is amino acid or absent
<220> FEATURE:
<221> NAME/KEY: MOD_RES
<222> LOCATION: (11)
<223> OTHER INFORMATION: Xaa is amino acid or absent
<220> FEATURE:
<221> NAME/KEY: MOD_RES
<222> LOCATION: (12)
<223> OTHER INFORMATION: Xaa is amino acid or absent

<400> SEQUENCE: 5

Xaa Xaa Xaa Xaa Xaa Xaa Xaa Xaa Xaa Xaa Xaa Xaa
1               5                  10

<210> SEQ ID NO 6
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<220> FEATURE:
<223> OTHER INFORMATION: Xaa is any amino acid with one or two
      aromatic,piperidine,pyrazine,pyrimidine,piperazine,morpholine,
      pyrimidinegroup(s),indole,pentalene,indene,naphthalene,benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is Bpa,Phe4NO2,any one amino acid,Tyr or
      Phe
<220> FEATURE:
<221> NAME/KEY: MOD_RES
<222> LOCATION: (7)
<223> OTHER INFORMATION: Xaa is any amino acid or absent
<220> FEATURE:
<221> NAME/KEY: MOD_RES
<222> LOCATION: (8)
<223> OTHER INFORMATION: Xaa is any amino acid or absent
```

-continued

```
<220> FEATURE:
<221> NAME/KEY: MOD_RES
<222> LOCATION: (9)
<223> OTHER INFORMATION: Xaa is any amino acid or absent
<220> FEATURE:
<221> NAME/KEY: MOD_RES
<222> LOCATION: (10)
<223> OTHER INFORMATION: Xaa is any amino acid or absent
<220> FEATURE:
<221> NAME/KEY: MOD_RES
<222> LOCATION: (11)
<223> OTHER INFORMATION: Xaa is any amino acid or absent
<220> FEATURE:
<221> NAME/KEY: MOD_RES
<222> LOCATION: (12)
<223> OTHER INFORMATION: Xaa is any amino acid or absent

<400> SEQUENCE: 6

Xaa Xaa Xaa Xaa Xaa Xaa Xaa Xaa Xaa Xaa Xaa Xaa
1               5                   10

<210> SEQ ID NO 7
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Bpa,Phe4NO2,any one amino acid,Tyr or
      Phe
<220> FEATURE:
<221> NAME/KEY: MOD_RES
<222> LOCATION: (2)
<223> OTHER INFORMATION: Xaa is any amino acid or absent
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (6)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<223> OTHER INFORMATION: Xaa is any amino acid with one or two
      aromatic,piperidine,pyrazine,pyrimidine,piperazine,morpholine or
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (7)
<223> OTHER INFORMATION: Xaa is any amino acid or absent
<220> FEATURE:
```

```
<221> NAME/KEY: MOD_RES
<222> LOCATION: (8)
<223> OTHER INFORMATION: Xaa is any amino acid or absent
<220> FEATURE:
<221> NAME/KEY: MOD_RES
<222> LOCATION: (9)
<223> OTHER INFORMATION: Xaa is any amino acid or absent
<220> FEATURE:
<221> NAME/KEY: MOD_RES
<222> LOCATION: (10)
<223> OTHER INFORMATION: Xaa is any amino acid or absent
<220> FEATURE:
<221> NAME/KEY: MOD_RES
<222> LOCATION: (11)
<223> OTHER INFORMATION: Xaa is any amino acid or absent
<220> FEATURE:
<221> NAME/KEY: MOD_RES
<222> LOCATION: (12)
<223> OTHER INFORMATION: Xaa is any amino acid or absent

<400> SEQUENCE: 7

Xaa Xaa Xaa Xaa Xaa Xaa Xaa Xaa Xaa Xaa Xaa Xaa
 1               5                  10

<210> SEQ ID NO 8
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Bpa,Phe4NO2,any one amino acid,Tyr or
      Phe
<220> FEATURE:
<221> NAME/KEY: MOD_RES
<222> LOCATION: (2)
<223> OTHER INFORMATION: Xaa is any amino acid or absent
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (6)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
```

```
<222> LOCATION: (7)
<223> OTHER INFORMATION: Xaa is any amino acid or absent
<220> FEATURE:
<221> NAME/KEY: MOD_RES
<222> LOCATION: (8)
<223> OTHER INFORMATION: Xaa is any amino acid or absent
<220> FEATURE:
<221> NAME/KEY: MOD_RES
<222> LOCATION: (9)
<223> OTHER INFORMATION: Xaa is any amino acid or absent
<220> FEATURE:
<221> NAME/KEY: MOD_RES
<222> LOCATION: (10)
<223> OTHER INFORMATION: Xaa is any amino acid or absent
<220> FEATURE:
<221> NAME/KEY: MOD_RES
<222> LOCATION: (11)
<223> OTHER INFORMATION: Xaa is any amino acid or absent
<220> FEATURE:
<221> NAME/KEY: MOD_RES
<222> LOCATION: (12)
<223> OTHER INFORMATION: Xaa is any amino acid or absent

<400> SEQUENCE: 8

Xaa Xaa Xaa Xaa Xaa Xaa Xaa Xaa Xaa Xaa Xaa Xaa
1               5                   10

<210> SEQ ID NO 9
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid or absent
<220> FEATURE:
<221> NAME/KEY: MOD_RES
<222> LOCATION: (2)
<223> OTHER INFORMATION: Xaa is any amino acid or absent
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is any amino acid or absent
<220> FEATURE:
<221> NAME/KEY: MOD_RES
<222> LOCATION: (7)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<220> FEATURE:
<223> OTHER INFORMATION: Xaa is any amino acid with one or two
      aromatic,piperidine,pyrazine,pyrimidine,piperazine,
      morpholine,pyrimidine group(s),indole,pentalene,indene,
      naphthalene,benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (8)
<223> OTHER INFORMATION: Xaa is Cha,Nal(2),(Phe-2,3,4,5,6-F),(Phe-3,4,
      5F),(Phe-4CF3) or an amino acid that occupies a similar side chain
```

```
           space
<223> OTHER INFORMATION: Xaa is any amino acid with one or two aromatic
      piperidine,pyrazine,pyrimidine,piperazine, morpholine,pyrimidine
      group(s),indole,pentalene,indene,naphthalene,benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (9)
<223> OTHER INFORMATION: Xaa is any amino acid or absent
<220> FEATURE:
<221> NAME/KEY: MOD_RES
<222> LOCATION: (10)
<223> OTHER INFORMATION: Xaa is any amino acid or absent
<220> FEATURE:
<221> NAME/KEY: MOD_RES
<222> LOCATION: (11)
<223> OTHER INFORMATION: Xaa is any amino acid or absent
<220> FEATURE:
<221> NAME/KEY: MOD_RES
<222> LOCATION: (12)
<223> OTHER INFORMATION: Xaa is Bpa,Phe4NO2,any one amino acid,Tyr or
      Phe

<400> SEQUENCE: 9

Xaa Xaa Xaa Xaa Xaa Xaa Xaa Xaa Xaa Xaa Xaa Xaa
1               5                   10

<210> SEQ ID NO 10
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any one amino or absent
<220> FEATURE:
<221> NAME/KEY: MOD_RES
<222> LOCATION: (2)
<223> OTHER INFORMATION: Xaa is any one amino or absent
<220> FEATURE:
<221> NAME/KEY: MOD_RES
<222> LOCATION: (3)
<223> OTHER INFORMATION: Xaa is any one amino or absent
<220> FEATURE:
<221> NAME/KEY: MOD_RES
<222> LOCATION: (4)
<223> OTHER INFORMATION: Xaa is any one amino or absent
<220> FEATURE:
<221> NAME/KEY: MOD_RES
<222> LOCATION: (5)
<223> OTHER INFORMATION: Xaa is any one amino or absent
<220> FEATURE:
<221> NAME/KEY: MOD_RES
<222> LOCATION: (6)
<223> OTHER INFORMATION: Xaa is any one amino or absent
<220> FEATURE:
<221> NAME/KEY: MOD_RES
<222> LOCATION: (7)
<223> OTHER INFORMATION: Xaa is Bpa,Phe4NO2,any one amino acid,Tyr or
      Phe
<220> FEATURE:
<221> NAME/KEY: MOD_RES
<222> LOCATION: (8)
<223> OTHER INFORMATION: Xaa is any amino acid or absent
<220> FEATURE:
<221> NAME/KEY: MOD_RES
<222> LOCATION: (9)
<223> OTHER INFORMATION: Xaa is any amino acid or absent
<220> FEATURE:
<221> NAME/KEY: MOD_RES
<222> LOCATION: (10)
<223> OTHER INFORMATION: Xaa is any amino acid or absent
```

```
<220> FEATURE:
<221> NAME/KEY: MOD_RES
<222> LOCATION: (11)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (12)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain

<400> SEQUENCE: 10

Xaa Xaa Xaa Xaa Xaa Xaa Xaa Xaa Xaa Xaa Xaa Xaa
1               5                   10

<210> SEQ ID NO 11
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid or absent
<220> FEATURE:
<221> NAME/KEY: MOD_RES
<222> LOCATION: (2)
<223> OTHER INFORMATION: Xaa is any amino acid or absent
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is any amino acid or absent
<220> FEATURE:
<221> NAME/KEY: MOD_RES
<222> LOCATION: (7)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
```

```
<220> FEATURE:
<221> NAME/KEY: MOD_RES
<222> LOCATION: (8)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (9)
<223> OTHER INFORMATION: Xaa is any amino acid or absent
<220> FEATURE:
<221> NAME/KEY: MOD_RES
<222> LOCATION: (10)
<223> OTHER INFORMATION: Xaa is any amino acid or absent
<220> FEATURE:
<221> NAME/KEY: MOD_RES
<222> LOCATION: (11)
<223> OTHER INFORMATION: Xaa is any amino acid or absent
<220> FEATURE:
<221> NAME/KEY: MOD_RES
<222> LOCATION: (12)
<223> OTHER INFORMATION: Xaa is Bpa,Phe4NO2,any one amino acid,Tyr or
      Phe

<400> SEQUENCE: 11

Xaa Xaa Xaa Xaa Xaa Xaa Xaa Xaa Xaa Xaa Xaa Xaa
1               5                   10

<210> SEQ ID NO 12
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid or absent
<220> FEATURE:
<221> NAME/KEY: MOD_RES
<222> LOCATION: (2)
<223> OTHER INFORMATION: Xaa is any amino acid or absent
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is any amino acid or absent
<220> FEATURE:
<221> NAME/KEY: MOD_RES
<222> LOCATION: (7)
<223> OTHER INFORMATION: Xaa is Bpa,Phe4NO2,any one amino acid,Tyr or
      Phe
<220> FEATURE:
<221> NAME/KEY: MOD_RES
<222> LOCATION: (8)
<223> OTHER INFORMATION: Xaa is any amino acid or absent
<220> FEATURE:
<221> NAME/KEY: MOD_RES
```

```
<222> LOCATION: (9)
<223> OTHER INFORMATION: Xaa is any amino acid or absent
<220> FEATURE:
<221> NAME/KEY: MOD_RES
<222> LOCATION: (10)
<223> OTHER INFORMATION: Xaa is any amino acid or absent
<220> FEATURE:
<221> NAME/KEY: MOD_RES
<222> LOCATION: (11)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (12)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain

<400> SEQUENCE: 12

Xaa Xaa Xaa Xaa Xaa Xaa Xaa Xaa Xaa Xaa Xaa Xaa
1               5                   10

<210> SEQ ID NO 13
<211> LENGTH: 8
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid or absent
<220> FEATURE:
<221> NAME/KEY: MOD_RES
<222> LOCATION: (2)
<223> OTHER INFORMATION: Xaa is any amino acid or absent
<220> FEATURE:
<221> NAME/KEY: MOD_RES
<222> LOCATION: (3)
<223> OTHER INFORMATION: Xaa is Bpa,Phe4NO2,any one amino acid,Tyr or
      Phe
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is any amino acid or absent
<220> FEATURE:
<221> NAME/KEY: MOD_RES
<222> LOCATION: (7)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<220> FEATURE:
```

```
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (8)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain

<400> SEQUENCE: 13

Xaa Xaa Xaa Xaa Xaa Xaa Xaa Xaa
1               5

<210> SEQ ID NO 14
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid or absent
<220> FEATURE:
<221> NAME/KEY: MOD_RES
<222> LOCATION: (2)
<223> OTHER INFORMATION: Xaa is any amino acid or absent
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is Bpa,Phe4NO2,any one amino acid,Tyr,or
      Phe
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is Bpa,Phe4NO2,any one amino acid,Tyr or
      Phe
<220> FEATURE:
<221> NAME/KEY: MOD_RES
<222> LOCATION: (7)
<223> OTHER INFORMATION: Xaa is any amino acid or absent or absent
<220> FEATURE:
<221> NAME/KEY: MOD_RES
<222> LOCATION: (8)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
```

```
<221> NAME/KEY: MOD_RES
<222> LOCATION: (9)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<223> OTHER INFORMATION: or any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain

<400> SEQUENCE: 14

Xaa Xaa Xaa Xaa Xaa Xaa Xaa Xaa Xaa
1               5

<210> SEQ ID NO 15
<211> LENGTH: 8
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3),Bpa,Phe4NO2,an amino acid that occupies a similar
      side chain space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (2)
<223> OTHER INFORMATION: Xaa is Cha, Nal(2),(Phe-2,3,4,5,6-F),(Phe-3,4,
      5F),(Phe-4CF3) or an amino acid that occupies a similar side chain
      space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is Bpa,Phe4NO2,any one amino acid,Tyr or
      Phe
<220> FEATURE:
<221> NAME/KEY: MOD_RES
<222> LOCATION: (7)
<223> OTHER INFORMATION: Xaa is any amino acid or absent
<220> FEATURE:
<221> NAME/KEY: MOD_RES
<222> LOCATION: (8)
<223> OTHER INFORMATION: Xaa is any amino acid or absent
```

```
<400> SEQUENCE: 15

Xaa Xaa Xaa Xaa Xaa Xaa Xaa Xaa
1               5

<210> SEQ ID NO 16
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3),Bpa,Phe4NO2,an amino acid that occupies a similar
      side chain space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is Bpa,Phe4NO2,any one amino acid,Tyr or
      Phe
<220> FEATURE:
<221> NAME/KEY: MOD_RES
<222> LOCATION: (7)
<223> OTHER INFORMATION: Xaa is any amino acid or absent
<220> FEATURE:
<221> NAME/KEY: MOD_RES
<222> LOCATION: (8)
<223> OTHER INFORMATION: Xaa is any amino acid or absent
<220> FEATURE:
<221> NAME/KEY: MOD_RES
<222> LOCATION: (9)
<223> OTHER INFORMATION: Xaa is any amino acid or absent

<400> SEQUENCE: 16

Xaa Xaa Xaa Xaa Xaa Xaa Xaa Xaa Xaa
1               5

<210> SEQ ID NO 17
<211> LENGTH: 12
<212> TYPE: PRT
```

```
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space,
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (3)
<223> OTHER INFORMATION: Xaa is any amino acid or absent
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino acid or absent
<220> FEATURE:
<221> NAME/KEY: MOD_RES
<222> LOCATION: (6)
<223> OTHER INFORMATION: Xaa is Bpa,Phe4NO2,any one amino acid,Tyr,Phe
      or nothing
<220> FEATURE:
<221> NAME/KEY: MOD_RES
<222> LOCATION: (7)
<223> OTHER INFORMATION: Xaa is any amino acid
<220> FEATURE:
<221> NAME/KEY: MOD_RES
<222> LOCATION: (8)
<223> OTHER INFORMATION: Xaa is any amino acid
<220> FEATURE:
<221> NAME/KEY: MOD_RES
<222> LOCATION: (9)
<223> OTHER INFORMATION: Xaa is any amino acid
<220> FEATURE:
<221> NAME/KEY: MOD_RES
<222> LOCATION: (10)
<223> OTHER INFORMATION: Xaa is any amino acid
<220> FEATURE:
<221> NAME/KEY: MOD_RES
<222> LOCATION: (11)
<223> OTHER INFORMATION: Xaa is any amino acid
<220> FEATURE:
<221> NAME/KEY: MOD_RES
<222> LOCATION: (12)
<223> OTHER INFORMATION: Xaa is any amino acid

<400> SEQUENCE: 17

Xaa Xaa Xaa Xaa Xaa Xaa Xaa Xaa Xaa Xaa Xaa Xaa
1               5                   10
```

-continued

```
<210> SEQ ID NO 18
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid
<220> FEATURE:
<221> NAME/KEY: MOD_RES
<222> LOCATION: (2)
<223> OTHER INFORMATION: Xaa is any amino acid
<220> FEATURE:
<221> NAME/KEY: MOD_RES
<222> LOCATION: (3)
<223> OTHER INFORMATION: Xaa is any amino acid
<220> FEATURE:
<221> NAME/KEY: MOD_RES
<222> LOCATION: (4)
<223> OTHER INFORMATION: Xaa is any amino acid
<220> FEATURE:
<221> NAME/KEY: MOD_RES
<222> LOCATION: (5)
<223> OTHER INFORMATION: Xaa is any amino acid
<220> FEATURE:
<221> NAME/KEY: MOD_RES
<222> LOCATION: (6)
<223> OTHER INFORMATION: Xaa is any amino acid
<220> FEATURE:
<221> NAME/KEY: MOD_RES
<222> LOCATION: (7)
<223> OTHER INFORMATION: Xaa is Bpa,Phe4NO2,any one amino acid,Tyr,Phe,
      or nothing
<220> FEATURE:
<221> NAME/KEY: MOD_RES
<222> LOCATION: (8)
<223> OTHER INFORMATION: Xaa is any amino acid or absent
<220> FEATURE:
<221> NAME/KEY: MOD_RES
<222> LOCATION: (9)
<223> OTHER INFORMATION: Xaa is any amino acid or absent
<220> FEATURE:
<221> NAME/KEY: MOD_RES
<222> LOCATION: (10)
<223> OTHER INFORMATION: Xaa is any amino acid or absent
<220> FEATURE:
<221> NAME/KEY: MOD_RES
<222> LOCATION: (11)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain
<220> FEATURE:
<221> NAME/KEY: MOD_RES
<222> LOCATION: (12)
<223> OTHER INFORMATION: Xaa is Cha,Nal(2),(Phe-2,3,4,5,6-F),(Phe-3,4,
      5F),(Phe-4CF3) or an amino acid that occupies a similar side chain
      space
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman
      quinoxaline or quinazoline group in the side chain

<400> SEQUENCE: 18

Xaa Xaa Xaa Xaa Xaa Xaa Xaa Xaa Xaa Xaa Xaa Xaa
```

```
                  1               5              10

<210> SEQ ID NO 19
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid
<220> FEATURE:
<221> NAME/KEY: MOD_RES
<222> LOCATION: (2)
<223> OTHER INFORMATION: Xaa is any amino acid
<220> FEATURE:
<221> NAME/KEY: MOD_RES
<222> LOCATION: (3)
<223> OTHER INFORMATION: Xaa is any amino acid
<220> FEATURE:
<221> NAME/KEY: MOD_RES
<222> LOCATION: (4)
<223> OTHER INFORMATION: Xaa is any amino acid
<220> FEATURE:
<221> NAME/KEY: MOD_RES
<222> LOCATION: (5)
<223> OTHER INFORMATION: Xaa is Bpa,Phe4NO2,any one amino acid,Tyr,Phe,
      or nothing
<220> FEATURE:
<221> NAME/KEY: MOD_RES
<222> LOCATION: (6)
<223> OTHER INFORMATION: Xaa is any amino acid
<220> FEATURE:
<221> NAME/KEY: MOD_RES
<222> LOCATION: (7)
<223> OTHER INFORMATION: Xaa is any amino acid or absent
<220> FEATURE:
<221> NAME/KEY: MOD_RES
<222> LOCATION: (8)
<223> OTHER INFORMATION: Xaa is any amino acid
<220> FEATURE:
<221> NAME/KEY: MOD_RES
<222> LOCATION: (9)
<223> OTHER INFORMATION: Xaa is Cha, Nal(2),(Phe-2,3,4,5,6-F),(Phe-3,4,
      5F),(Phe-4CF3) or an amino acid that occupies a similar side chain
      space
<220> FEATURE:
<223> OTHER INFORMATION: Xaa is any amino acid with one or two
      aromatic,piperidine,pyrazine,pyrimidine,piperazine,morpholine,
      pyrimidine group(s),indole,pentalene,indene,naphthalene,
      benzofuran,
<220> FEATURE:
<223> OTHER INFORMATION: benzothiophene,quinoline,indoline,chroman,
      quinoxaline or quinazoline group in the side chain

<400> SEQUENCE: 19

Xaa Xaa Xaa Xaa Xaa Xaa Xaa Xaa Xaa
1               5

<210> SEQ ID NO 20
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3),Bpa,Phe4NO2 or an amino acid that occupies a
      similar side chain space
<220> FEATURE:
<223> OTHER INFORMATION: Xaa is any amino acid with one or two
```

```
        aromatic,piperidine,pyrazine,pyrimidine,piperazine,morpholine,
        pyrimidine group(s),indole,pentalene,indene,naphthalene,
        benzofuran,
<220> FEATURE:
<223> OTHER INFORMATION: benzothiophene,quinoline,indoline,chroman,
        quinoxaline or quinazoline group in the side chain
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
        5F),(Phe-4CF3) or an amino acid that occupies a similar side chain
        space
<223> OTHER INFORMATION: Xaa is any amino acid with one or two
        aromatic,piperidine,pyrazine,pyrimidine,piperazine,morpholine,
        pyrimidine group(s),indole,pentalene,indene,naphthalene,
        benzofuran,
<220> FEATURE:
<223> OTHER INFORMATION: benzothiophene,quinoline,indoline,chroman,
        quinoxaline,quinazoline group in the side chain
<220> FEATURE:
<221> NAME/KEY: MOD_RES
<222> LOCATION: (3)
<223> OTHER INFORMATION: Xaa is any amino acid
<220> FEATURE:
<221> NAME/KEY: MOD_RES
<222> LOCATION: (4)
<223> OTHER INFORMATION: Xaa is any amino acid or absent
<220> FEATURE:
<221> NAME/KEY: MOD_RES
<222> LOCATION: (5)
<223> OTHER INFORMATION: Xaa is any amino
<220> FEATURE:
<221> NAME/KEY: MOD_RES
<222> LOCATION: (6)
<223> OTHER INFORMATION: Xaa is Bpa,Phe4NO2,any one amino acid,Tyr,Phe
        or nothing
<220> FEATURE:
<221> NAME/KEY: MOD_RES
<222> LOCATION: (7)
<223> OTHER INFORMATION: Xaa is any amino acid
<220> FEATURE:
<221> NAME/KEY: MOD_RES
<222> LOCATION: (8)
<223> OTHER INFORMATION: Xaa is any amino acid
<220> FEATURE:
<221> NAME/KEY: MOD_RES
<222> LOCATION: (9)
<223> OTHER INFORMATION: Xaa is any amino acid

<400> SEQUENCE: 20

Xaa Xaa Xaa Xaa Xaa Xaa Xaa Xaa Xaa
1               5

<210> SEQ ID NO 21
<211> LENGTH: 6
<212> TYPE: PRT
<213> ORGANISM: Artificial sequence
<220> FEATURE:
<223> OTHER INFORMATION: Description of artificial sequence: Synthetic
        peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
        5F),(Phe-4CF3),Bpa,Phe4NO2,Tyr or Phe
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
        5F),(Phe-4CF3),Bpa,Phe4NO2,Tyr or Phe
<220> FEATURE:
<221> NAME/KEY: MOD_RES
<222> LOCATION: (3)
<223> OTHER INFORMATION: Xaa is Ser,Arg,Cys,Pro or Asn
<220> FEATURE:
<221> NAME/KEY: MOD_RES
<222> LOCATION: (5)
```

```
<223> OTHER INFORMATION: Xaa is Ser,Arg,Asn,Ser,Arg,Cys,Pro,Asn, Trp, a
      single aminoundecanoic acid or a single 8-aminocaprylic acid
<220> FEATURE:
<221> NAME/KEY: MOD_RES
<222> LOCATION: (6)
<223> OTHER INFORMATION: Xaa is Bpa or Phe4NO2

<400> SEQUENCE: 21

Xaa Xaa Xaa Trp Xaa Xaa
1               5

<210> SEQ ID NO 22
<211> LENGTH: 6
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Bpa or Phe4NO2
<220> FEATURE:
<221> NAME/KEY: MOD_RES
<222> LOCATION: (2)
<223> OTHER INFORMATION: Xaa is is Ser,Arg,Asn,Ser,Arg,Cys,Pro,Asn,Trp a
      single aminoundecanoic acid or a single 8-aminocaprylic acid
<220> FEATURE:
<221> NAME/KEY: MOD_RES
<222> LOCATION: (4)
<223> OTHER INFORMATION: Xaa is Ser,Arg,Cys,Pro or Asn
<220> FEATURE:
<221> NAME/KEY: MOD_RES
<222> LOCATION: (5)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (6)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe

<400> SEQUENCE: 22

Xaa Xaa Trp Xaa Xaa Xaa
1               5

<210> SEQ ID NO 23
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (3)
<223> OTHER INFORMATION: Xaa is Ser,Arg,Cys,Pro or Asn
<220> FEATURE:
<221> NAME/KEY: MOD_RES
<222> LOCATION: (5)
<223> OTHER INFORMATION: Xaa is Ser,Arg,Asn, Ser,Arg,Cys,Pro,Asn,Trp,a
      single aminoundecanoic acid or a single 8-aminocaprylic acid
<220> FEATURE:
<221> NAME/KEY: MOD_RES
<222> LOCATION: (6)
```

```
<223> OTHER INFORMATION: Xaa is Bpa or Phe4NO2
<220> FEATURE:
<221> NAME/KEY: MOD_RES
<222> LOCATION: (7)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (8)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (9)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (10)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (11)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (12)
<223> OTHER INFORMATION: Xaa is any amino acid if 3 or more Xaa at site
      7,8,9,10,11 or 12 are Arg or Lys

<400> SEQUENCE: 23

Xaa Xaa Xaa Trp Xaa xaa Xaa Xaa Xaa Xaa Xaa Xaa
1               5                   10

<210> SEQ ID NO 24
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (3)
<223> OTHER INFORMATION: Xaa is Ser,Arg,Cys,Pro or Asn
<220> FEATURE:
<221> NAME/KEY: MOD_RES
<222> LOCATION: (5)
<223> OTHER INFORMATION: Xaa is Ser,Arg,Asn,Ser,Arg,Cys,Pro,Asn,Trp,a
      single aminoundecanoic acid or a single 8-aminocaprylic acid
<220> FEATURE:
<221> NAME/KEY: MOD_RES
<222> LOCATION: (6)
<223> OTHER INFORMATION: Xaa is Bpa or Phe4NO2
<220> FEATURE:
<221> NAME/KEY: MOD_RES
<222> LOCATION: (7)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (8)
<223> OTHER INFORMATION: Xaa is any amino acid if 3 or more Xaa at site
      7,8,9,10,11 or 12 are Arg or Lys
<220> FEATURE:
```

```
<221> NAME/KEY: MOD_RES
<222> LOCATION: (9)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (10)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (11)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (12)
<223> OTHER INFORMATION: Xaa is any amino acid if 3 or more Xaa at site
      7,8,9,10,11 or 12 are Arg or Lys

<400> SEQUENCE: 24

Xaa Xaa Xaa Trp Xaa Xaa Xaa Xaa Xaa Xaa Xaa Xaa
1               5                   10

<210> SEQ ID NO 25
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Bpa or Phe4NO2
<220> FEATURE:
<221> NAME/KEY: MOD_RES
<222> LOCATION: (2)
<223> OTHER INFORMATION: Xaa is Ser,Arg,Asn,Ser,Arg,Cys,Pro,Asn,Trp,a
      single aminoundecanoic acid or a single 8-aminocaprylic acid
<220> FEATURE:
<221> NAME/KEY: MOD_RES
<222> LOCATION: (4)
<223> OTHER INFORMATION: Xaa is Ser,Arg,Cys,Pro or Asn
<220> FEATURE:
<221> NAME/KEY: MOD_RES
<222> LOCATION: (5)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (6)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (7)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (8)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (9)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (10)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (11)
```

```
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (12)
<223> OTHER INFORMATION: Xaa is any amino acid if 3 or more Xaa at site
      7,8,9,10,11 or 12 are Arg or Lys

<400> SEQUENCE: 25

Xaa Xaa Trp Xaa Xaa Xaa Xaa Xaa Xaa Xaa Xaa Xaa
1               5                   10

<210> SEQ ID NO 26
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Bpa or Phe4NO2
<220> FEATURE:
<221> NAME/KEY: MOD_RES
<222> LOCATION: (2)
<223> OTHER INFORMATION: Xaa is Ser,Arg,Asn, Ser,Arg,Cys,Pro,Asn,Trp,a
      single aminoundecanoic acid or a single 8-aminocaprylic acid
<220> FEATURE:
<221> NAME/KEY: MOD_RES
<222> LOCATION: (4)
<223> OTHER INFORMATION: Xaa is Ser,Arg,Cys,Pro,or Asn
<220> FEATURE:
<221> NAME/KEY: MOD_RES
<222> LOCATION: (5)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (6)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (7)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (8)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (9)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (10)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (11)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (12)
<223> OTHER INFORMATION: Xaa is any amino acid if 3 or more Xaa at site
      7,8,9,10,11 or 12 are Arg or Lys

<400> SEQUENCE: 26

Xaa Xaa Trp Xaa Xaa Phe Xaa Xaa Xaa Xaa Xaa Xaa
1               5                   10
```

```
<210> SEQ ID NO 27
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (2)
<223> OTHER INFORMATION:
<220> FEATURE:
<221> NAME/KEY: MOD_RES
<222> LOCATION: (3)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (4)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (5)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (6)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (7)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (8)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (9)
<223> OTHER INFORMATION: Xaa is Ser,Arg,Cys,Pro or Asn
<220> FEATURE:
<221> NAME/KEY: MOD_RES
<222> LOCATION: (11)
<223> OTHER INFORMATION: Xaa is Ser,Arg,Asn,Ser,Arg,Cys,Pro,Asn,Trp,a
      single aminoundecanoic acid or a single 8-aminocaprylic acid
<220> FEATURE:
<221> NAME/KEY: MOD_RES
<222> LOCATION: (12)
<223> OTHER INFORMATION: Xaa is Bpa or Phe4NO2

<400> SEQUENCE: 27

Xaa Xaa Xaa Xaa Xaa Xaa Xaa Xaa Xaa Trp Xaa Xaa
1               5                   10

<210> SEQ ID NO 28
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid if 3 or more Xaa at site
```

1,2,3,4,5,or 6 are Arg or Lys
<220> FEATURE:
<221> NAME/KEY: MOD_RES
<222> LOCATION: (2)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (3)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (4)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (5)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (6)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (7)
<223> OTHER INFORMATION: Xaa is Bpa or Phe4NO2
<220> FEATURE:
<221> NAME/KEY: MOD_RES
<222> LOCATION: (8)
<223> OTHER INFORMATION: Xaa is Ser,Arg,Asn,Ser,Arg,Cys,Pro,Asn,Trp a
      single aminoundecanoic acid or a single 8-aminocaprylic acid
<220> FEATURE:
<221> NAME/KEY: MOD_RES
<222> LOCATION: (10)
<223> OTHER INFORMATION: Xaa is Ser,Arg,Cys,Pro or Asn
<220> FEATURE:
<221> NAME/KEY: MOD_RES
<222> LOCATION: (11)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (12)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe

<400> SEQUENCE: 28

Xaa Xaa Xaa Xaa Xaa Xaa Xaa Xaa Trp Xaa Xaa Xaa
1               5                   10

<210> SEQ ID NO 29
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (2)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (3)
<223> OTHER INFORMATION: Xaa is any amino acid if 3 or more Xaa at site
      1,2,3,4,5,or 6 are Arg or Lys
<220> FEATURE:

```
<221> NAME/KEY: MOD_RES
<222> LOCATION: (4)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (5)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (6)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (7)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (8)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (9)
<223> OTHER INFORMATION: Xaa is Ser,Arg,Cys,Pro or Asn
<220> FEATURE:
<221> NAME/KEY: MOD_RES
<222> LOCATION: (11)
<223> OTHER INFORMATION: Xaa is Ser,Arg,Asn,Ser,Arg,Cys,Pro,Asn,Trp,a
      single aminoundecanoic acid or a single 8-aminocaprylic acid
<220> FEATURE:
<221> NAME/KEY: MOD_RES
<222> LOCATION: (12)
<223> OTHER INFORMATION: Xaa is Bpa or Phe4NO2

<400> SEQUENCE: 29

Xaa Xaa Xaa Xaa Xaa Xaa Xaa Xaa Xaa Trp Xaa Xaa
1               5                   10

<210> SEQ ID NO 30
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (2)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (3)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (4)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (5)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (6)
```

```
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (7)
<223> OTHER INFORMATION: Xaa is Bpa or Phe4NO2
<220> FEATURE:
<221> NAME/KEY: MOD_RES
<222> LOCATION: (8)
<223> OTHER INFORMATION: Xaa is Ser,Arg,Asn,Ser,Arg,Cys,Pro,Asn,Trp,a
      single aminoundecanoic acid or a single 8-aminocaprylic acid
<220> FEATURE:
<221> NAME/KEY: MOD_RES
<222> LOCATION: (9)
<223> OTHER INFORMATION: Xaa is Ser,Arg,Cys,Pro or Asn
<220> FEATURE:
<221> NAME/KEY: MOD_RES
<222> LOCATION: (11)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (12)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe

<400> SEQUENCE: 30

Xaa Xaa Xaa Xaa Xaa Xaa Xaa Xaa Trp Xaa Xaa Xaa
1               5                   10

<210> SEQ ID NO 31
<211> LENGTH: 8
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (2)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (3)
<223> OTHER INFORMATION: Xaa is Bpa or Phe4NO2
<220> FEATURE:
<221> NAME/KEY: MOD_RES
<222> LOCATION: (4)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (5)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (6)
<223> OTHER INFORMATION: Xaa is any amino acid if 3 or more Xaa at site
      1,2,3,4,5,or 6 are Arg or Lys
<220> FEATURE:
<221> NAME/KEY: MOD_RES
<222> LOCATION: (7)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (8)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
```

-continued

```
<400> SEQUENCE: 31

Xaa Xaa Xaa Xaa Xaa Xaa Xaa Xaa
1               5

<210> SEQ ID NO 32
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid if 3 or more Xaa at site
      1,2,3,4,5,or 7 are Arg or Lys
<220> FEATURE:
<221> NAME/KEY: MOD_RES
<222> LOCATION: (2)
<223> OTHER INFORMATION: Xaa is any amino acid if 3 or more Xaa at site
      1,2,3,4,5,or 7 are Arg or Lys
<220> FEATURE:
<221> NAME/KEY: MOD_RES
<222> LOCATION: (3)
<223> OTHER INFORMATION: Xaa is any amino acid if 3 or more Xaa at site
      1,2,3,4,5,or 7 are Arg or Lys
<220> FEATURE:
<221> NAME/KEY: MOD_RES
<222> LOCATION: (4)
<223> OTHER INFORMATION: Xaa is Bpa or Phe4NO2
<220> FEATURE:
<221> NAME/KEY: MOD_RES
<222> LOCATION: (5)
<223> OTHER INFORMATION: Xaa is any amino acid if 3 or more Xaa at site
      1,2,3,4,5,or 7 are Arg or Lys
<220> FEATURE:
<221> NAME/KEY: MOD_RES
<222> LOCATION: (7)
<223> OTHER INFORMATION: Xaa is any amino acid if 3 or more Xaa at site
      1,2,3,4,5,or 7 are Arg or Lys
<220> FEATURE:
<221> NAME/KEY: MOD_RES
<222> LOCATION: (8)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (9)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe

<400> SEQUENCE: 32

Xaa Xaa Xaa Xaa Xaa Trp Xaa Xaa xaa
1               5

<210> SEQ ID NO 33
<211> LENGTH: 8
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (3)
```

```
<223> OTHER INFORMATION: Xaa is any amino acid if 3 or more Xaa at site
      3,4,5,6,7 or 8 are Arg or Lys
<220> FEATURE:
<221> NAME/KEY: MOD_RES
<222> LOCATION: (4)
<223> OTHER INFORMATION: Xaa is any amino acid if 3 or more Xaa at site
      3,4,5,6,7 or 8 are Arg or Lys
<220> FEATURE:
<221> NAME/KEY: MOD_RES
<222> LOCATION: (5)
<223> OTHER INFORMATION: Xaa is any amino acid if 3 or more Xaa at site
      3,4,5,6,7 or 8 are Arg or Lys
<220> FEATURE:
<221> NAME/KEY: MOD_RES
<222> LOCATION: (6)
<223> OTHER INFORMATION: Xaa is Bpa or Phe4NO2
<220> FEATURE:
<221> NAME/KEY: MOD_RES
<222> LOCATION: (7)
<223> OTHER INFORMATION: Xaa is any amino acid if 3 or more Xaa at site
      3,4,5,6,7 or 8 are Arg or Lys
<220> FEATURE:
<221> NAME/KEY: MOD_RES
<222> LOCATION: (8)
<223> OTHER INFORMATION: Xaa is any amino acid if 3 or more Xaa at site
      3,4,5,6,7 or 8 are Arg or Lys

<400> SEQUENCE: 33

Xaa Xaa Xaa Xaa Xaa Xaa Xaa Xaa
1               5

<210> SEQ ID NO 34
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (2)
<223> OTHER INFORMATION: Xaa is Cha,Nal(2),(Phe-2,3,4,5,6-F),(Phe-3,4,
      5F),(Phe-4CF3),Bpa,Phe4NO2,Tyr or Phe
<220> FEATURE:
<221> NAME/KEY: MOD_RES
<222> LOCATION: (3)
<223> OTHER INFORMATION: Xaa is any amino acid if 3 or more Xaa at site
      3,5,7,8 or 9 are Arg or Lys
<220> FEATURE:
<221> NAME/KEY: MOD_RES
<222> LOCATION: (5)
<223> OTHER INFORMATION: Xaa is any amino acid if 3 or more Xaa at site
      3,5,7,8 or 9 are Arg or Lys
<220> FEATURE:
<221> NAME/KEY: MOD_RES
<222> LOCATION: (6)
<223> OTHER INFORMATION: Xaa is Bpa or Phe4NO2
<220> FEATURE:
<221> NAME/KEY: MOD_RES
<222> LOCATION: (7)
<223> OTHER INFORMATION: Xaa is any amino acid if 3 or more Xaa at site
      3,5,7,8 or 9 are Arg or Lys
<220> FEATURE:
<221> NAME/KEY: MOD_RES
<222> LOCATION: (8)
<223> OTHER INFORMATION: Xaa is any amino acid if 3 or more Xaa at site
      3,5,7,8 or 9 are Arg or Lys
<220> FEATURE:
<221> NAME/KEY: MOD_RES
<222> LOCATION: (9)
<223> OTHER INFORMATION: Xaa is any amino acid if 3 or more Xaa at site
      3,5,7,8 or 9 are Arg or Lys
```

<400> SEQUENCE: 34

Xaa Xaa Xaa Trp Xaa Xaa Xaa Xaa Xaa
1               5

<210> SEQ ID NO 35
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha or Nal(2)
<220> FEATURE:
<221> NAME/KEY: MOD_RES
<222> LOCATION: (2)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (5)
<223> OTHER INFORMATION: Xaa is Ser or Asn
<220> FEATURE:
<221> NAME/KEY: MOD_RES
<222> LOCATION: (6)
<223> OTHER INFORMATION: Xaa is Bpa or Phe4NO2
<220> FEATURE:
<221> NAME/KEY: MOD_RES
<222> LOCATION: (7)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (8)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (9)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (10)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (11)
<223> OTHER INFORMATION: Xaa is any amino acid if 3 or more Xaa at site
      7,8,9,10,11 or 12 are Arg or Lys
<220> FEATURE:
<221> NAME/KEY: MOD_RES
<222> LOCATION: (12)
<223> OTHER INFORMATION: Xaa is any amino acid if 3 or more Xaa at site
      7,8,9,10,11 or 12 are Arg or Lys

<400> SEQUENCE: 35

Xaa Xaa Ser Trp Xaa Xaa Xaa Xaa Xaa Xaa Xaa Xaa
1               5                   10

<210> SEQ ID NO 36
<211> LENGTH: 12
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is any amino acid if 3 or more Xaa at site 1,2,3,4,5 or 6 are Arg or Lys
<220> FEATURE:
<221> NAME/KEY: MOD_RES
<222> LOCATION: (2)
<223> OTHER INFORMATION: Xaa is any amino acid if 3 or more Xaa at site
    1,2,3,4,5 or 6 are Arg or Lys
<220> FEATURE:
<221> NAME/KEY: MOD_RES
<222> LOCATION: (3)
<223> OTHER INFORMATION: Xaa is any amino acid if 3 or more Xaa at site
    1,2,3,4,5 or 6 are Arg or Lys
<220> FEATURE:
<221> NAME/KEY: MOD_RES
<222> LOCATION: (4)
<223> OTHER INFORMATION: Xaa is any amino acid if 3 or more Xaa at site
    1,2,3,4,5 or 6 are Arg or Lys
<220> FEATURE:
<221> NAME/KEY: MOD_RES
<222> LOCATION: (5)
<223> OTHER INFORMATION: Xaa is any amino acid if 3 or more Xaa at site
    1,2,3,4,5 or 6 are Arg or Lys
<220> FEATURE:
<221> NAME/KEY: MOD_RES
<222> LOCATION: (6)
<223> OTHER INFORMATION: Xaa is any amino acid if 3 or more Xaa at site
    1,2,3,4,5 or 6 are Arg or Lys
<220> FEATURE:
<221> NAME/KEY: MOD_RES
<222> LOCATION: (7)
<223> OTHER INFORMATION: Xaa is Bpa or Phe4NO2
<220> FEATURE:
<221> NAME/KEY: MOD_RES
<222> LOCATION: (8)
<223> OTHER INFORMATION: Xaa is Ser or Asn
<220> FEATURE:
<221> NAME/KEY: MOD_RES
<222> LOCATION: (11)
<223> OTHER INFORMATION: Xaa is (Phe-2,3,4,5,6-F),(Phe-3,4,5F) or (Phe-
    4CF3)
<220> FEATURE:
<221> NAME/KEY: MOD_RES
<222> LOCATION: (12)
<223> OTHER INFORMATION: Xaa is Cha or Nal(2)

<400> SEQUENCE: 36

Xaa Xaa Xaa Xaa Xaa Xaa Xaa Xaa Trp Ser Xaa Xaa
1               5                   10

<210> SEQ ID NO 37
<211> LENGTH: 9
<212> TYPE: PRT
<213> ORGANISM: Artificial sequence
<220> FEATURE:
<223> OTHER INFORMATION: Description of artificial sequence: Synthetic
    peptide
<220> FEATURE:
<221> NAME/KEY: MOD_RES
<222> LOCATION: (1)
<223> OTHER INFORMATION: Xaa is any amino acid if 3 or more Xaa at site
    1,2,3,5,7 or 8 are Arg or Lys
<220> FEATURE:
<221> NAME/KEY: MOD_RES
<222> LOCATION: (2)
<223> OTHER INFORMATION: Xaa is any amino acid if 3 or more Xaa at site
    1,2,3,5,7 or 8 are Arg or Lys
<220> FEATURE:
<221> NAME/KEY: MOD_RES
<222> LOCATION: (3)
<223> OTHER INFORMATION: Xaa is any amino acid if 3 or more Xaa at site
    1,2,3,5,7 or 8 are Arg or Lys
<220> FEATURE:
<221> NAME/KEY: MOD_RES
<222> LOCATION: (4)
<223> OTHER INFORMATION: Xaa is Bpa,Phe4NO2,(Ser-Tyr) or (Ser-Phe)
<220> FEATURE:
<221> NAME/KEY: MOD_RES
<222> LOCATION: (5)

```
<223> OTHER INFORMATION: Xaa is any amino acid if 3 or more Xaa at site
      1,2,3,5,7 or 8 are Arg or Lys
<220> FEATURE:
<221> NAME/KEY: MOD_RES
<222> LOCATION: (7)
<223> OTHER INFORMATION: Xaa is any amino acid if 3 or more Xaa at site
      1,2,3,5,7 or 8 are Arg or Lys
<220> FEATURE:
<221> NAME/KEY: MOD_RES
<222> LOCATION: (8)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (9)
<223> OTHER INFORMATION: Xaa is Cha or Nal(2)

<400> SEQUENCE: 37

Xaa Xaa Xaa Xaa Xaa Trp Xaa Xaa Xaa
1               5

<210> SEQ ID NO 38
<211> LENGTH: 9
<212> TYPE: PRT
<213> ORGANISM: Artificial sequence
<220> FEATURE:
<223> OTHER INFORMATION: Description of artificial sequence: Synthetic
      peptide
<220> FEATURE:
<221> NAME/KEY: MOD_RES
<222> LOCATION: (1)
<223> OTHER INFORMATION: Xaa is Cha or Nal(2)
<220> FEATURE:
<221> NAME/KEY: MOD_RES
<222> LOCATION: (2)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (3)
<223> OTHER INFORMATION: Xaa is any amino acid if 3 or more Xaa at site
      1,3,5,7,8 or 9 are Arg or Lys
<220> FEATURE:
<221> NAME/KEY: MOD_RES
<222> LOCATION: (5)
<223> OTHER INFORMATION: Xaa is any amino acid if 3 or more Xaa at site
      1,3,5,7,8 or 9 are Arg or Lys
<220> FEATURE:
<221> NAME/KEY: MOD_RES
<222> LOCATION: (6)
<223> OTHER INFORMATION: Xaa is Bpa or Phe4NO2
<220> FEATURE:
<221> NAME/KEY: MOD_RES
<222> LOCATION: (7)
<223> OTHER INFORMATION: Xaa is any amino acid if 3 or more Xaa at site
      1,3,5,7,8 or 9 are Arg or Lys
<220> FEATURE:
<221> NAME/KEY: MOD_RES
<222> LOCATION: (8)
<223> OTHER INFORMATION: Xaa is any amino acid if 3 or more Xaa at site
      1,3,5,7,8 or 9 are Arg or Lys
<220> FEATURE:
<221> NAME/KEY: MOD_RES
<222> LOCATION: (9)
<223> OTHER INFORMATION: Xaa is any amino acid if 3 or more Xaa at site
      1,3,5,7,8 or 9 are Arg or Lys

<400> SEQUENCE: 38

Xaa Xaa Xaa Trp Xaa Xaa Xaa Xaa Xaa
1               5

<210> SEQ ID NO 39
<211> LENGTH: 6
<212> TYPE: PRT
<213> ORGANISM: Artificial sequence
```

```
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Cha or d-Nal(2)
<220> FEATURE:
<221> NAME/KEY: MOD_RES
<222> LOCATION: (2)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (6)
<223> OTHER INFORMATION: Xaa is d-Bpa

<400> SEQUENCE: 39

Xaa Xaa Ser Trp Ser Xaa
1               5

<210> SEQ ID NO 40
<211> LENGTH: 6
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Bpa
<220> FEATURE:
<221> NAME/KEY: MOD_RES
<222> LOCATION: (5)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (6)
<223> OTHER INFORMATION: Xaa is d-Cha or d-Nal(2)

<400> SEQUENCE: 40

Xaa Ser Trp Ser Xaa Xaa
1               5

<210> SEQ ID NO 41
<211> LENGTH: 6
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Cha or d-Nal(2)
<220> FEATURE:
<221> NAME/KEY: MOD_RES
<222> LOCATION: (2)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (3)
<223> OTHER INFORMATION: Xaa is any amino acid
<220> FEATURE:
<221> NAME/KEY: MOD_RES
<222> LOCATION: (4)
<223> OTHER INFORMATION: Xaa is d- or l-Trp
<220> FEATURE:
<221> NAME/KEY: MOD_RES
<222> LOCATION: (5)
<223> OTHER INFORMATION: Xaa is any amino acid
<220> FEATURE:
```

<221> NAME/KEY: MOD_RES
<222> LOCATION: (6)
<223> OTHER INFORMATION: Xaa is d-Bpa

<400> SEQUENCE: 41

Xaa Xaa Xaa Xaa Xaa Xaa
1               5

<210> SEQ ID NO 42
<211> LENGTH: 6
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Bpa
<220> FEATURE:
<221> NAME/KEY: MOD_RES
<222> LOCATION: (2)
<223> OTHER INFORMATION: Xaa is any amino acid
<220> FEATURE:
<221> NAME/KEY: MOD_RES
<222> LOCATION: (3)
<223> OTHER INFORMATION: Xaa is d- or l-Trp
<220> FEATURE:
<221> NAME/KEY: MOD_RES
<222> LOCATION: (4)
<223> OTHER INFORMATION: Xaa is any amino acid
<220> FEATURE:
<221> NAME/KEY: MOD_RES
<222> LOCATION: (5)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (6)
<223> OTHER INFORMATION: Xaa is d-Cha or d-Nal(2)

<400> SEQUENCE: 42

Xaa Xaa Xaa Xaa Xaa Xaa
1               5

<210> SEQ ID NO 43
<211> LENGTH: 12
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Cha or d-Nal(2)
<220> FEATURE:
<221> NAME/KEY: MOD_RES
<222> LOCATION: (2)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (3)
<223> OTHER INFORMATION: Xaa is any amino acid
<220> FEATURE:
<221> NAME/KEY: MOD_RES
<222> LOCATION: (4)
<223> OTHER INFORMATION: Xaa is d- or l-Trp
<220> FEATURE:
<221> NAME/KEY: MOD_RES
<222> LOCATION: (5)
<223> OTHER INFORMATION: Xaa is any amino acid
<220> FEATURE:
<221> NAME/KEY: MOD_RES

```
<222> LOCATION: (6)
<223> OTHER INFORMATION: Xaa is d-Bpa

<400> SEQUENCE: 43

Xaa Xaa Xaa Xaa Xaa Xaa Arg Arg Arg Arg Arg Arg
1               5                   10

<210> SEQ ID NO 44
<211> LENGTH: 12
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Cha or d-Nal(2)
<220> FEATURE:
<221> NAME/KEY: MOD_RES
<222> LOCATION: (2)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (3)
<223> OTHER INFORMATION: Xaa is any amino acid
<220> FEATURE:
<221> NAME/KEY: MOD_RES
<222> LOCATION: (4)
<223> OTHER INFORMATION: Xaa is d- or l-Trp
<220> FEATURE:
<221> NAME/KEY: MOD_RES
<222> LOCATION: (5)
<223> OTHER INFORMATION: Xaa is any amino acid
<220> FEATURE:
<221> NAME/KEY: MOD_RES
<222> LOCATION: (6)
<223> OTHER INFORMATION: Xaa is d-Bpa
<220> FEATURE:
<221> NAME/KEY: MOD_RES
<222> LOCATION: (7)
<223> OTHER INFORMATION: Xaa is d- or l-Arg

<400> SEQUENCE: 44

Xaa Xaa Xaa Xaa Xaa Xaa Xaa Arg Arg Arg Arg Arg
1               5                   10

<210> SEQ ID NO 45
<211> LENGTH: 12
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Bpa
<220> FEATURE:
<221> NAME/KEY: MOD_RES
<222> LOCATION: (2)
<223> OTHER INFORMATION: Xaa is any amino acid
<220> FEATURE:
<221> NAME/KEY: MOD_RES
<222> LOCATION: (3)
<223> OTHER INFORMATION: Xaa is d- or l-Trp
<220> FEATURE:
<221> NAME/KEY: MOD_RES
<222> LOCATION: (4)
<223> OTHER INFORMATION: Xaa is any amino acid
<220> FEATURE:
<221> NAME/KEY: MOD_RES
<222> LOCATION: (5)
<223> OTHER INFORMATION: Xaa is (Phe-2,3,4,5,6-F),(Phe-3,4,5F) or (Phe-
```

```
        4CF3)
<220> FEATURE:
<221> NAME/KEY: MOD_RES
<222> LOCATION: (6)
<223> OTHER INFORMATION: Xaa is d-Cha or d-Nal(2)
<220> FEATURE:
<221> NAME/KEY: MOD_RES
<222> LOCATION: (12)
<223> OTHER INFORMATION: Xaa is d- or l-Arg

<400> SEQUENCE: 45

Xaa Xaa Xaa Xaa Xaa Xaa Arg Arg Arg Arg Arg Xaa
 1               5                  10

<210> SEQ ID NO 46
<211> LENGTH: 12
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Bpa
<220> FEATURE:
<221> NAME/KEY: MOD_RES
<222> LOCATION: (2)
<223> OTHER INFORMATION: Xaa is any amino acid
<220> FEATURE:
<221> NAME/KEY: MOD_RES
<222> LOCATION: (3)
<223> OTHER INFORMATION: Xaa is d- or l-Trp
<220> FEATURE:
<221> NAME/KEY: MOD_RES
<222> LOCATION: (4)
<223> OTHER INFORMATION: Xaa is any amino acid
<220> FEATURE:
<221> NAME/KEY: MOD_RES
<222> LOCATION: (5)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (6)
<223> OTHER INFORMATION: Xaa is d-Cha or d-Nal(2)
<220> FEATURE:
<221> NAME/KEY: MOD_RES
<222> LOCATION: (7)
<223> OTHER INFORMATION: Xaa is d- or l-Arg

<400> SEQUENCE: 46

Xaa Xaa Xaa Xaa Xaa Xaa Xaa Arg Arg Arg Arg Arg
 1               5                  10

<210> SEQ ID NO 47
<211> LENGTH: 12
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (6)
<223> OTHER INFORMATION: Xaa is d- or l-Arg
<220> FEATURE:
<221> NAME/KEY: MOD_RES
<222> LOCATION: (7)
<223> OTHER INFORMATION: Xaa is d-Cha or d-Nal(2)
<220> FEATURE:
<221> NAME/KEY: MOD_RES
<222> LOCATION: (8)
<223> OTHER INFORMATION: Xaa is (Phe-2,3,4,5,6-F),(Phe-3,4,5F) or (Phe-
      4CF3)
```

```
<220> FEATURE:
<221> NAME/KEY: MOD_RES
<222> LOCATION: (9)
<223> OTHER INFORMATION: Xaa is any amino acid
<220> FEATURE:
<221> NAME/KEY: MOD_RES
<222> LOCATION: (10)
<223> OTHER INFORMATION: Xaa is d- or l-Trp
<220> FEATURE:
<221> NAME/KEY: MOD_RES
<222> LOCATION: (11)
<223> OTHER INFORMATION: Xaa is any amino acid
<220> FEATURE:
<221> NAME/KEY: MOD_RES
<222> LOCATION: (12)
<223> OTHER INFORMATION: Xaa is d-Bpa

<400> SEQUENCE: 47

Arg Arg Arg Arg Arg Xaa Xaa Xaa Xaa Xaa Xaa Xaa
1               5                   10

<210> SEQ ID NO 48
<211> LENGTH: 12
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (6)
<223> OTHER INFORMATION: Xaa is d- or l-Arg
<220> FEATURE:
<221> NAME/KEY: MOD_RES
<222> LOCATION: (7)
<223> OTHER INFORMATION: Xaa is d-Bpa
<220> FEATURE:
<221> NAME/KEY: MOD_RES
<222> LOCATION: (8)
<223> OTHER INFORMATION: Xaa is any amino acid
<220> FEATURE:
<221> NAME/KEY: MOD_RES
<222> LOCATION: (9)
<223> OTHER INFORMATION: Xaa is d- or l-Trp
<220> FEATURE:
<221> NAME/KEY: MOD_RES
<222> LOCATION: (10)
<223> OTHER INFORMATION: Xaa is any amino acid
<220> FEATURE:
<221> NAME/KEY: MOD_RES
<222> LOCATION: (11)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (12)
<223> OTHER INFORMATION: Xaa is d-Cha or d-Nal(2)

<400> SEQUENCE: 48

Arg Arg Arg Arg Arg Xaa Xaa Xaa Xaa Xaa Xaa Xaa
1               5                   10

<210> SEQ ID NO 49
<211> LENGTH: 12
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d- or l-Arg
<220> FEATURE:
<221> NAME/KEY: MOD_RES
```

```
<222> LOCATION: (7)
<223> OTHER INFORMATION: Xaa is d-Cha or d-Nal(2)
<220> FEATURE:
<221> NAME/KEY: MOD_RES
<222> LOCATION: (8)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (9)
<223> OTHER INFORMATION: Xaa is any amino acid
<220> FEATURE:
<221> NAME/KEY: MOD_RES
<222> LOCATION: (10)
<223> OTHER INFORMATION: Xaa is d- or l-Trp
<220> FEATURE:
<221> NAME/KEY: MOD_RES
<222> LOCATION: (11)
<223> OTHER INFORMATION: Xaa is any amino acid
<220> FEATURE:
<221> NAME/KEY: MOD_RES
<222> LOCATION: (12)
<223> OTHER INFORMATION: Xaa is d-Bpa

<400> SEQUENCE: 49

Xaa Arg Arg Arg Arg Arg Xaa Xaa Xaa Xaa Xaa Xaa
1               5                   10

<210> SEQ ID NO 50
<211> LENGTH: 12
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d- or l-Arg
<220> FEATURE:
<221> NAME/KEY: MOD_RES
<222> LOCATION: (7)
<223> OTHER INFORMATION: Xaa is d-Bpa
<220> FEATURE:
<221> NAME/KEY: MOD_RES
<222> LOCATION: (8)
<223> OTHER INFORMATION: Xaa is any amino acid
<220> FEATURE:
<221> NAME/KEY: MOD_RES
<222> LOCATION: (9)
<223> OTHER INFORMATION: Xaa is d- or l-Trp
<220> FEATURE:
<221> NAME/KEY: MOD_RES
<222> LOCATION: (10)
<223> OTHER INFORMATION: Xaa is any amino acid
<220> FEATURE:
<221> NAME/KEY: MOD_RES
<222> LOCATION: (11)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (12)
<223> OTHER INFORMATION: Xaa is d-Cha or d-Nal(2)

<400> SEQUENCE: 50

Xaa Arg Arg Arg Arg Arg Xaa Xaa Xaa Xaa Xaa Xaa
1               5                   10

<210> SEQ ID NO 51
<211> LENGTH: 8
<212> TYPE: PRT
<213> ORGANISM: Artificial sequence
<220> FEATURE:
<223> OTHER INFORMATION: Description of artificial sequence: sequence
```

```
                    containing d-form peptide
<220> FEATURE:
<221> NAME/KEY: MOD_RES
<222> LOCATION: (1)
<223> OTHER INFORMATION: Xaa is d- or l-Arg
<220> FEATURE:
<221> NAME/KEY: MOD_RES
<222> LOCATION: (3)
<223> OTHER INFORMATION: Xaa is d-Bpa
<220> FEATURE:
<221> NAME/KEY: MOD_RES
<222> LOCATION: (7)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (8)
<223> OTHER INFORMATION: Xaa is d-Cha or d-Nal(2)

<400> SEQUENCE: 51

Xaa Arg Xaa Arg Arg Arg Xaa Xaa
1               5

<210> SEQ ID NO 52
<211> LENGTH: 9
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Cha or d-Nal(2)
<220> FEATURE:
<221> NAME/KEY: MOD_RES
<222> LOCATION: (4)
<223> OTHER INFORMATION: Xaa is d-Bpa
<220> FEATURE:
<221> NAME/KEY: MOD_RES
<222> LOCATION: (6)
<223> OTHER INFORMATION: Xaa is d- or l-Trp
<220> FEATURE:
<221> NAME/KEY: MOD_RES
<222> LOCATION: (8)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (9)
<223> OTHER INFORMATION: Xaa is d-Cha or d-Nal(2)

<400> SEQUENCE: 52

Xaa Arg Arg Xaa Arg Xaa Arg Xaa Xaa
1               5

<210> SEQ ID NO 53
<211> LENGTH: 8
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Cha or d-Nal(2)
<220> FEATURE:
<221> NAME/KEY: MOD_RES
<222> LOCATION: (2)
<223> OTHER INFORMATION: Xaa is (Phe-2,3,4,5,6-F),(Phe-3,4,5F) or (Phe-
      4CF3)
<220> FEATURE:
<221> NAME/KEY: MOD_RES
<222> LOCATION: (6)
```

```
<223> OTHER INFORMATION: Xaa is d-Bpa
<220> FEATURE:
<221> NAME/KEY: MOD_RES
<222> LOCATION: (8)
<223> OTH

```
      containing d-form peptide
<220> FEATURE:
<221> NAME/KEY: MOD_RES
<222> LOCATION: (3)
<223> OTHER INFORMATION: Xaa is Gln or Arg
<220> FEATURE:
<221> NAME/KEY: MOD_RES
<222> LOCATION: (7)
<223> OTHER INFORMATION: Xaa is d-Bpa
<220> FEATURE:
<221> NAME/KEY: MOD_RES
<222> LOCATION: (11)
<223> OTHER INFORMATION: Xaa is Phe-2,3,4,5,6-F
<220> FEATURE:
<221> NAME/KEY: MOD_RES
<222> LOCATION: (12)
<223> OTHER INFORMATION: Xaa is d-Cha or d-Nal(2)

<400> SEQUENCE: 56

Arg Arg Xaa Arg Arg Arg Xaa Ser Trp Ser Xaa Xaa
1               5                   10

<210> SEQ ID NO 57
<211> LENGTH: 9
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (3)
<223> OTHER INFORMATION: Xaa is Gln or Arg
<220> FEATURE:
<221> NAME/KEY: MOD_RES
<222> LOCATION: (4)
<223> OTHER INFORMATION: Xaa is d-Bpa
<220> FEATURE:
<221> NAME/KEY: MOD_RES
<222> LOCATION: (8)
<223> OTHER INFORMATION: Xaa is Phe-2,3,4,5,6-F
<220> FEATURE:
<221> NAME/KEY: MOD_RES
<222> LOCATION: (9)
<223> OTHER INFORMATION: Xaa is d-Cha or d-Nal(2)

<400> SEQUENCE: 57

Arg Arg Xaa Xaa Arg Trp Arg Xaa Xaa
1               5

<210> SEQ ID NO 58
<211> LENGTH: 9
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: MOD_RES
<222> LOCATION: (1)
<223> OTHER INFORMATION: Xaa is d-Cha or d-Nal(2)
<220> FEATURE:
<221> NAME/KEY: MOD_RES
<222> LOCATION: (2)
<223> OTHER INFORMATION: Xaa is Phe-2,3,4,5,6-F
<220> FEATURE:
<221> NAME/KEY: MOD_RES
<222> LOCATION: (6)
<223> OTHER INFORMATION: Xaa is d-Bpa
<220> FEATURE:
<221> NAME/KEY: MOD_RES
<222> LOCATION: (7)
<223> OTHER INFORMATION: Xaa is Gln or Arg

<400> SEQUENCE: 58
```

```
Xaa Xaa Arg Trp Arg Xaa Xaa Arg Arg
1               5
```

<210> SEQ ID NO 59
<211> LENGTH: 12
<212> TYPE: PRT
<213> ORGANISM: Artificial sequence
<220> FEATURE:
<223> OTHER INFORMATION: Description of artificial sequence: sequence
      containing d-form peptide
<220> FEATURE:
<221> NAME/KEY: misc_feature
<222> LOCATION: (1)
<223> OTHER INFORMATION: Xaa is d-Benzoyl-phenylalanine
<220> FEATURE:
<221> NAME/KEY: misc_feature
<222> LOCATION: (6)
<223> OTHER INFORMATION: Xaa is d-Cyclohexyl-alanine

<400> SEQUENCE: 59

```
Xaa Ser Trp Ser Phe Xaa Arg Arg Gln Arg Arg Arg
1               5                   10
```

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Gln
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Bpa
<220> FEATURE:
<221> NAME/KEY: MISC_FEATURE
<222> LOCATION: (8)..(8)
<223> OTHER INFORMATION: Xaa is d-Ser
<220> FEATURE:
<221> NAME/KEY: MISC_FEATURE
<222> LOCATION: (9)..(9)
<223> OTHER INFORMATION: Xaa is d-Trp
<220> FEATURE:
<221> NAME/KEY: MISC_FEATURE
<222> LOCATION: (10)..(10)
<223> OTHER INFORMATION: Xaa is d-Ser
<220> FEATURE:
<221> NAME/KEY: MISC_FEATURE
<222> LOCATION: (11)..(11)
<223> OTHER INFORMATION: Xaa is d-Phe-2,3,4,5,6-F
<220> FEATURE:

<221> NAME/KEY: MISC_FEATURE
<222> LOCATION: (12)..(12)
<223> OTHER INFORMATION: Xaa is d-Cha

<400> SEQUENCE: 60

Xaa Xaa Xaa Xaa Xaa Xaa Xaa Xaa Xaa Xaa Xaa Xaa
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Cha
<220> FEATURE:
<221> NAME/KEY: MISC_FEATURE
<222> LOCATION: (2)..(2)
<223> OTHER INFORMATION: Xaa is d-Phe-2,3,4,5,6-F
<220> FEATURE:
<221> NAME/KEY: MISC_FEATURE
<222> LOCATION: (3)..(3)
<223> OTHER INFORMATION: Xaa is d-Ser
<220> FEATURE:
<221> NAME/KEY: MISC_FEATURE
<222> LOCATION: (4)..(4)
<223> OTHER INFORMATION: Xaa is d-Trp
<220> FEATURE:
<221> NAME/KEY: MISC_FEATURE
<222> LOCATION: (5)..(5)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Bpa
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 61

Xaa Xaa Xaa Xaa Xaa Xaa Xaa Xaa Xaa Xaa Xaa Xaa
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids

```
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Gln
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Phe-2,3,4,5,6-F
<220> FEATURE:
<221> NAME/KEY: MISC_FEATURE
<222> LOCATION: (9)..(9)
<223> OTHER INFORMATION: Xaa is d-Ser
<220> FEATURE:
<221> NAME/KEY: MISC_FEATURE
<222> LOCATION: (10)..(10)
<223> OTHER INFORMATION: Xaa is d-Trp
<220> FEATURE:
<221> NAME/KEY: MISC_FEATURE
<222> LOCATION: (11)..(11)
<223> OTHER INFORMATION: Xaa is d-Ser
<220> FEATURE:
<221> NAME/KEY: MISC_FEATURE
<222> LOCATION: (12)..(12)
<223> OTHER INFORMATION: Xaa is d-Bpa

<400> SEQUENCE: 62

Xaa Xaa Xaa Xaa Xaa Xaa Xaa Xaa Xaa Xaa Xaa Xaa
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Cha
<220> FEATURE:
<221> NAME/KEY: MISC_FEATURE
<222> LOCATION: (2)..(2)
<223> OTHER INFORMATION: Xaa is d-Phe-2,3,4,5,6-F
<220> FEATURE:
<221> NAME/KEY: MISC_FEATURE
<222> LOCATION: (3)..(3)
<223> OTHER INFORMATION: Xaa is d-Ser
<220> FEATURE:
<221> NAME/KEY: MISC_FEATURE
<222> LOCATION: (4)..(4)
<223> OTHER INFORMATION: Xaa is d-Trp
<220> FEATURE:
```

```
<221> NAME/KEY: MISC_FEATURE
<222> LOCATION: (5)..(5)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Bpa
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Gln
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 63

Xaa Xaa Xaa Xaa Xaa Xaa Xaa Xaa Xaa Xaa Xaa Xaa
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Gln
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Phe-2,3,4,5,6-F
<220> FEATURE:
<221> NAME/KEY: MISC_FEATURE
```

```
<222> LOCATION: (9)..(9)
<223> OTHER INFORMATION: Xaa is d-Ser
<220> FEATURE:
<221> NAME/KEY: MISC_FEATURE
<222> LOCATION: (10)..(10)
<223> OTHER INFORMATION: Xaa is d-Trp
<220> FEATURE:
<221> NAME/KEY: MISC_FEATURE
<222> LOCATION: (11)..(11)
<223> OTHER INFORMATION: Xaa is d-Ser
<220> FEATURE:
<221> NAME/KEY: MISC_FEATURE
<222> LOCATION: (12)..(12)
<223> OTHER INFORMATION: Xaa is d-Bpa

<400> SEQUENCE: 64

Xaa Xaa Xaa Xaa Xaa Xaa Xaa Xaa Xaa Xaa Xaa Xaa
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Phe-2,3,4,5,6-F
<220> FEATURE:
<221> NAME/KEY: MISC_FEATURE
<222> LOCATION: (9)..(9)
<223> OTHER INFORMATION: Xaa is d-Ser
<220> FEATURE:
<221> NAME/KEY: MISC_FEATURE
<222> LOCATION: (10)..(10)
<223> OTHER INFORMATION: Xaa is d-Trp
<220> FEATURE:
<221> NAME/KEY: MISC_FEATURE
<222> LOCATION: (11)..(11)
<223> OTHER INFORMATION: Xaa is d-Ser
<220> FEATURE:
<221> NAME/KEY: MISC_FEATURE
<222> LOCATION: (12)..(12)
<223> OTHER INFORMATION: Xaa is d-Bpa

<400> SEQUENCE: 65
```

```
Xaa Xaa Xaa Xaa Xaa Xaa Xaa Xaa Xaa Xaa Xaa Xaa
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Cha
<220> FEATURE:
<221> NAME/KEY: MISC_FEATURE
<222> LOCATION: (2)..(2)
<223> OTHER INFORMATION: Xaa is d-Phe-2,3,4,5,6-F
<220> FEATURE:
<221> NAME/KEY: MISC_FEATURE
<222> LOCATION: (3)..(3)
<223> OTHER INFORMATION: Xaa is d-Ser
<220> FEATURE:
<221> NAME/KEY: MISC_FEATURE
<222> LOCATION: (4)..(4)
<223> OTHER INFORMATION: Xaa is d-Trp
<220> FEATURE:
<221> NAME/KEY: MISC_FEATURE
<222> LOCATION: (5)..(5)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Bpa
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 66

Xaa Xaa Xaa Xaa Xaa Xaa Xaa Xaa Xaa Xaa Xaa Xaa
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
```

```
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Bpa
<220> FEATURE:
<221> NAME/KEY: MISC_FEATURE
<222> LOCATION: (8)..(8)
<223> OTHER INFORMATION: Xaa is d-Ser
<220> FEATURE:
<221> NAME/KEY: MISC_FEATURE
<222> LOCATION: (9)..(9)
<223> OTHER INFORMATION: Xaa is d-Trp
<220> FEATURE:
<221> NAME/KEY: MISC_FEATURE
<222> LOCATION: (10)..(10)
<223> OTHER INFORMATION: Xaa is d-Ser
<220> FEATURE:
<221> NAME/KEY: MISC_FEATURE
<222> LOCATION: (11)..(11)
<223> OTHER INFORMATION: Xaa is d-Phe-2,3,4,5,6-F
<220> FEATURE:
<221> NAME/KEY: MISC_FEATURE
<222> LOCATION: (12)..(12)
<223> OTHER INFORMATION: Xaa is d-Cha

<400> SEQUENCE: 67

Xaa Xaa Xaa Xaa Xaa Xaa Xaa Xaa Xaa Xaa Xaa Xaa
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
```

```
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 68

Xaa Xaa Xaa Xaa Xaa Xaa Xaa Xaa Xaa Xaa Xaa Xaa
1               5                   10

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Bpa
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Phe-2,3,4,5,6-F
<220> FEATURE:
<221> NAME/KEY: MISC_FEATURE
<222> LOCATION: (8)..(8)
<223> OTHER INFORMATION: Xaa is d-Cha

<400> SEQUENCE: 69

Xaa Xaa Xaa Xaa Xaa Xaa Xaa Xaa
1               5

<210> SEQ ID NO 70
```

```
<211> LENGTH: 8
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Cha
<220> FEATURE:
<221> NAME/KEY: MISC_FEATURE
<222> LOCATION: (2)..(2)
<223> OTHER INFORMATION: Xaa is d-Phe-2,3,4,5,6-F
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Bpa
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg

<400> SEQUENCE: 70

Xaa Xaa Xaa Xaa Xaa Xaa Xaa Xaa
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Bpa
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Trp
<220> FEATURE:
<221> NAME/KEY: MISC_FEATURE
<222> LOCATION: (7)..(7)
```

```
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Phe-2,3,4,5,6-F
<220> FEATURE:
<221> NAME/KEY: MISC_FEATURE
<222> LOCATION: (9)..(9)
<223> OTHER INFORMATION: Xaa is d-Cha

<400> SEQUENCE: 71

Xaa Xaa Xaa Xaa Xaa Xaa Xaa Xaa Xaa
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Cha
<220> FEATURE:
<221> NAME/KEY: MISC_FEATURE
<222> LOCATION: (2)..(2)
<223> OTHER INFORMATION: Xaa is d-Phe-2,3,4,5,6,-F
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Trp
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Bpa
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg

<400> SEQUENCE: 72

Xaa Xaa Xaa Xaa Xaa Xaa Xaa Xaa Xaa
1               5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
```

```
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Bpa
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Trp
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Phe-2,3,4,5,6-F
<220> FEATURE:
<221> NAME/KEY: MISC_FEATURE
<222> LOCATION: (10)..(10)
<223> OTHER INFORMATION: Xaa is d-Cha

<400> SEQUENCE: 73

Xaa Xaa Xaa Xaa Xaa Xaa Xaa Xaa Xaa Xaa
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Cha
<220> FEATURE:
<221> NAME/KEY: MISC_FEATURE
<222> LOCATION: (2)..(2)
<223> OTHER INFORMATION: Xaa is d-Phe-2,3,4,5,6,7-F
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Trp
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Bpa
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
```

```
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg

<400> SEQUENCE: 74

Xaa Xaa Xaa Xaa Xaa Xaa Xaa Xaa Xaa Xaa
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Bpa
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Phe-2,3,4,5,6-F
<220> FEATURE:
<221> NAME/KEY: MISC_FEATURE
<222> LOCATION: (9)..(9)
<223> OTHER INFORMATION: Xaa is d-Cha

<400> SEQUENCE: 75

Xaa Xaa Xaa Xaa Xaa Xaa Xaa Xaa Xaa
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Cha
<220> FEATURE:
<221> NAME/KEY: MISC_FEATURE
```

```
<222> LOCATION: (2)..(2)
<223> OTHER INFORMATION: Xaa is d-Phe-2,3,4,5,6,-F
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Bpa
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg

<400> SEQUENCE: 76

Xaa Xaa Xaa Xaa Xaa Xaa Xaa Xaa Xaa
 1               5

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6,-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
```

```
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 77

Xaa Xaa Xaa Xaa Xaa Xaa Xaa Xaa Xaa Xaa xaa Xaa
1               5                   10

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (10)..(10)
<223> OTHER INFORMATION: Xaa is d-Cha
<220> FEATURE:
<221> NAME/KEY: MISC_FEATURE
<222> LOCATION: (11)..(11)
<223> OTHER INFORMATION: Xaa is d-Phe-2,3,4,5,6-F

<400> SEQUENCE: 78

Gly Arg Lys Lys Arg Arg Gln Arg Arg Xaa Xaa Arg Ser Pro Ser Tyr Tyr
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6,-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
```

<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (13)..(13)
<223> OTHER INFORMATION: Xaa is d-Lys
<220> FEATURE:
<221> NAME/KEY: MISC_FEATURE
<222> LOCATION: (14)..(14)
<223> OTHER INFORMATION: Xaa is d-Lys
<220> FEATURE:
<221> NAME/KEY: MISC_FEATURE
<222> LOCATION: (15)..(15)
<223> OTHER INFORMATION: Xaa is d-Arg

<400> SEQUENCE: 79

Xaa Xaa Xaa Xaa Xaa Xaa Xaa Xaa Xaa Xaa xaa Xaa Xaa xaa Xaa
1               5                   10                  15

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)

```
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 80

Xaa Xaa Xaa Xaa Xaa Xaa Xaa Xaa Xaa Xaa Xaa Xaa
1               5                   10

<210> SEQ ID NO 81
<211> LENGTH: 6
<212> TYPE: PRT
<213> ORGANISM: Artificial sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha

<400> SEQUENCE: 81

Xaa Xaa Xaa Xaa Xaa Xaa
1               5

<210> SEQ ID NO 82
<211> LENGTH: 10
<212> TYPE: PRT
<213> ORGANISM: Artificial sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
```

```
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Gln
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg

<400> SEQUENCE: 82

Xaa Xaa Xaa Xaa Xaa Xaa Xaa Xaa Xaa Xaa
1               5                   10

<210> SEQ ID NO 83
<211> LENGTH: 11
<212> TYPE: PRT
<213> ORGANISM: Artificial sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Gln
<220> FEATURE:
<221> NAME/KEY: MISC_FEATURE
<222> LOCATION: (10)..(10)
```

```
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Arg

<400> SEQUENCE: 83

Xaa Xaa Xaa Xaa Xaa Xaa Xaa Xaa Xaa Xaa Xaa
1               5                   10

<210> SEQ ID NO 84
<211> LENGTH: 10
<212> TYPE: PRT
<213> ORGANISM: Artificial sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln

<400> SEQUENCE: 84

Xaa Xaa Xaa Xaa Xaa Xaa Xaa Xaa Xaa Xaa
1               5                   10

<210> SEQ ID NO 85
<211> LENGTH: 11
<212> TYPE: PRT
<213> ORGANISM: Artificial sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
```

```
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln
<220> FEATURE:
<221> NAME/KEY: MISC_FEATURE
<222> LOCATION: (11)..(11)
<223> OTHER INFORMATION: Xaa is d-Arg

<400> SEQUENCE: 85

Xaa Xaa Xaa Xaa Xaa Xaa Xaa Xaa Xaa Xaa Xaa
1               5                   10

<210> SEQ ID NO 86
<211> LENGTH: 6
<212> TYPE: PRT
<213> ORGANISM: Artificial sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Gln
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg

<400> SEQUENCE: 86
```

```
Xaa Xaa Xaa Xaa Xaa Xaa
1               5
```

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Tyr
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Pro
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is l-Cha
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Gln
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (13)..(13)
<223> OTHER INFORMATION: Xaa is l-Arg

<400> SEQUENCE: 87

```
Xaa Xaa Xaa Trp Ser Xaa Xaa Xaa Xaa Xaa Xaa Xaa Xaa
1               5                   10
```

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Tyr
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE

```
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Gln
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (13)..(13)
<223> OTHER INFORMATION: Xaa is d-Arg

<400> SEQUENCE: 88

Xaa Xaa Pro Trp Ser Xaa Xaa Xaa Xaa Xaa Xaa Xaa Xaa
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe4NO2
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
```

```
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 89

Xaa Xaa Xaa Xaa Xaa Xaa Xaa Xaa Xaa Xaa Xaa Xaa
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Arg

<400> SEQUENCE: 90

Xaa Xaa Xaa Xaa Xaa Xaa Xaa Xaa Xaa Xaa Xaa
1               5                   10

<210> SEQ ID NO 91
```

```
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 91

Xaa Xaa Xaa Xaa Xaa Xaa Xaa Xaa Xaa Xaa Xaa Xaa
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
```

```
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Lys
<220> FEATURE:
<221> NAME/KEY: MISC_FEATURE
<222> LOCATION: (8)..(8)
<223> OTHER INFORMATION: Xaa is d-Lys
<220> FEATURE:
<221> NAME/KEY: MISC_FEATURE
<222> LOCATION: (9)..(9)
<223> OTHER INFORMATION: Xaa is d-Lys
<220> FEATURE:
<221> NAME/KEY: MISC_FEATURE
<222> LOCATION: (10)..(10)
<223> OTHER INFORMATION: Xaa is d-Lys
<220> FEATURE:
<221> NAME/KEY: MISC_FEATURE
<222> LOCATION: (11)..(11)
<223> OTHER INFORMATION: Xaa is d-Lys
<220> FEATURE:
<221> NAME/KEY: MISC_FEATURE
<222> LOCATION: (12)..(12)
<223> OTHER INFORMATION: Xaa is d-Lys

<400> SEQUENCE: 92

Xaa Xaa Xaa Xaa Xaa Xaa Xaa Xaa Xaa Xaa Xaa Xaa
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Gln
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Cha
```

```
<220> FEATURE:
<221> NAME/KEY: MISC_FEATURE
<222> LOCATION: (8)..(8)
<223> OTHER INFORMATION: Xaa is d-Phe-2,3,4,5,6-F
<220> FEATURE:
<221> NAME/KEY: MISC_FEATURE
<222> LOCATION: (9)..(9)
<223> OTHER INFORMATION: Xaa is d-Ser
<220> FEATURE:
<221> NAME/KEY: MISC_FEATURE
<222> LOCATION: (10)..(10)
<223> OTHER INFORMATION: Xaa is d-Trp
<220> FEATURE:
<221> NAME/KEY: MISC_FEATURE
<222> LOCATION: (11)..(11)
<223> OTHER INFORMATION: Xaa is d-Ser
<220> FEATURE:
<221> NAME/KEY: MISC_FEATURE
<222> LOCATION: (12)..(12)
<223> OTHER INFORMATION: Xaa is d-Bpa

<400> SEQUENCE: 93

Xaa Xaa Xaa Xaa Xaa Xaa Xaa Xaa Xaa Xaa Xaa Xaa
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Gln
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Bpa
<220> FEATURE:
<221> NAME/KEY: MISC_FEATURE
<222> LOCATION: (8)..(8)
<223> OTHER INFORMATION: Xaa is d-Ser
<220> FEATURE:
<221> NAME/KEY: MISC_FEATURE
<222> LOCATION: (9)..(9)
<223> OTHER INFORMATION: Xaa is d-Trp
<220> FEATURE:
<221> NAME/KEY: MISC_FEATURE
<222> LOCATION: (10)..(10)
<223> OTHER INFORMATION: Xaa is d-Ser
<220> FEATURE:
<221> NAME/KEY: MISC_FEATURE
<222> LOCATION: (11)..(11)
<223> OTHER INFORMATION: Xaa is d-Phe-2,3,4,5,6-F
<220> FEATURE:
```

<221> NAME/KEY: MISC_FEATURE
<222> LOCATION: (12)..(12)
<223> OTHER INFORMATION: Xaa is d-Cha

<400> SEQUENCE: 94

Xaa Xaa Xaa Xaa Xaa Xaa Xaa Xaa Xaa Xaa Xaa Xaa
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Phe-2,3,4,5,6-F
<220> FEATURE:
<221> NAME/KEY: MISC_FEATURE
<222> LOCATION: (9)..(9)
<223> OTHER INFORMATION: Xaa is d-Ser
<220> FEATURE:
<221> NAME/KEY: MISC_FEATURE
<222> LOCATION: (10)..(10)
<223> OTHER INFORMATION: Xaa is d-Trp
<220> FEATURE:
<221> NAME/KEY: MISC_FEATURE
<222> LOCATION: (11)..(11)
<223> OTHER INFORMATION: Xaa is d-Ser
<220> FEATURE:
<221> NAME/KEY: MISC_FEATURE
<222> LOCATION: (12)..(12)
<223> OTHER INFORMATION: Xaa is d-Bpa

<400> SEQUENCE: 95

Xaa Xaa Xaa Xaa Xaa Xaa Xaa Xaa Xaa Xaa Xaa Xaa
1               5                   10

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: peptide
      containing modified amino acids and d-form amino acids

```
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Bpa
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Phe-2,3,4,5,6-F
<220> FEATURE:
<221> NAME/KEY: MISC_FEATURE
<222> LOCATION: (8)..(8)
<223> OTHER INFORMATION: Xaa is d-Cha

<400> SEQUENCE: 96

Xaa Xaa Xaa Xaa Xaa Xaa Xaa Xaa
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Bpa
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Trp
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Phe-2,3,4,5,6-F
<220> FEATURE:
```

```
<221> NAME/KEY: MISC_FEATURE
<222> LOCATION: (9)..(9)
<223> OTHER INFORMATION: Xaa is d-Cha

<400> SEQUENCE: 97

Xaa Xaa Xaa Xaa Xaa Xaa Xaa Xaa Xaa
1               5

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Bpa
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Trp
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Phe-2,3,4,5,6-F
<220> FEATURE:
<221> NAME/KEY: MISC_FEATURE
<222> LOCATION: (10)..(10)
<223> OTHER INFORMATION: Xaa is d-Cha

<400> SEQUENCE: 98

Xaa Xaa Xaa Xaa Xaa Xaa Xaa Xaa Xaa Xaa
1               5                   10

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
```

```
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Bpa
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Phe-2,3,4,5,6-F
<220> FEATURE:
<221> NAME/KEY: MISC_FEATURE
<222> LOCATION: (9)..(9)
<223> OTHER INFORMATION: Xaa is d-Cha

<400> SEQUENCE: 99

Xaa Xaa Xaa Xaa Xaa Xaa Xaa Xaa Xaa
1               5

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Gln
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Bpa
<220> FEATURE:
<221> NAME/KEY: MISC_FEATURE
<222> LOCATION: (8)..(8)
<223> OTHER INFORMATION: Xaa is d-Ser
<220> FEATURE:
<221> NAME/KEY: MISC_FEATURE
<222> LOCATION: (9)..(9)
<223> OTHER INFORMATION: Xaa is d-Trp
<220> FEATURE:
```

```
<221> NAME/KEY: MISC_FEATURE
<222> LOCATION: (10)..(10)
<223> OTHER INFORMATION: Xaa is d-Ser
<220> FEATURE:
<221> NAME/KEY: MISC_FEATURE
<222> LOCATION: (11)..(11)
<223> OTHER INFORMATION: Xaa is d-Phe-2,3,4,5,6-F
<220> FEATURE:
<221> NAME/KEY: MISC_FEATURE
<222> LOCATION: (12)..(12)
<223> OTHER INFORMATION: Xaa is d-Cha

<400> SEQUENCE: 100

Xaa Xaa Xaa Xaa Xaa Xaa Xaa Xaa Xaa Xaa Xaa Xaa
1               5                   10

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha

<400> SEQUENCE: 101

Xaa Xaa Xaa Xaa Xaa Xaa
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Tyr
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Pro
<220> FEATURE:
<221> NAME/KEY: MISC_FEATURE
<222> LOCATION: (4)..(4)
<223> OTHER INFORMATION: Xaa is d-Trp
```

```
<220> FEATURE:
<221> NAME/KEY: MISC_FEATURE
<222> LOCATION: (5)..(5)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is d-Cha

<400> SEQUENCE: 102

Xaa Xaa Xaa Xaa Xaa Xaa Xaa
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Cys
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Cys

<400> SEQUENCE: 103

Xaa Xaa Xaa Xaa Xaa Xaa Xaa
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Tyr
<220> FEATURE:
<221> NAME/KEY: MISC_FEATURE
<222> LOCATION: (2)..(2)
<223> OTHER INFORMATION: Xaa is d-Cys
<220> FEATURE:
<221> NAME/KEY: MISC_FEATURE
<222> LOCATION: (3)..(3)
```

```
<223> OTHER INFORMATION: Xaa is d-Pro
<220> FEATURE:
<221> NAME/KEY: MISC_FEATURE
<222> LOCATION: (4)..(4)
<223> OTHER INFORMATION: Xaa is d-Trp
<220> FEATURE:
<221> NAME/KEY: MISC_FEATURE
<222> LOCATION: (5)..(5)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Cys

<400> SEQUENCE: 104

Xaa Xaa Xaa Xaa Xaa Xaa Xaa Xaa
1               5

<210> SEQ ID NO 105
<211> LENGTH: 19
<212> TYPE: PRT
<213> ORGANISM: Artificial Sequence
<220> FEATURE:
<223> OTHER INFORMATION: Description of Artificial Sequence: peptide
      containing modified amino acids
<220> FEATURE:
<221> NAME/KEY: MISC_FEATURE
<222> LOCATION: (12)..(12)
<223> OTHER INFORMATION: Xaa is l-Cha
<220> FEATURE:
<221> NAME/KEY: MOD-RES
<222> LOCATION: (13)..(13)
<223> OTHER INFORMATION: Xaa is l-Phe-2,3,4,5,6-F

<400> SEQUENCE: 105

Tyr Gly Arg Lys Lys Arg Arg Gln Arg Arg Xaa Xaa Arg Ser
1               5                   10                  15

Pro Ser Tyr Tyr

<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: peptide
      containing modified amino acids
<220> FEATURE:
<221> NAME/KEY: MISC_FEATURE
<222> LOCATION: (12)..(12)
<223> OTHER INFORMATION: Xaa is l-Cha
<220> FEATURE:
<221> NAME/KEY: MOD-RES
<222> LOCATION: (13)..(13)
<223> OTHER INFORMATION: Xaa is l-Phe-2,3,4,5,6-F

<400> SEQUENCE: 106

Tyr Gly Arg Lys Lys Arg Arg Gln Arg Arg Xaa Xaa Arg Ser Pro
1               5                   10                  15

Ser Tyr

<210> SEQ ID NO 107
<211> LENGTH: 11
<212> TYPE: PRT
```

```
<213> ORGANISM: Artificial Sequence
<220> FEATURE:
<223> OTHER INFORMATION: Description of Artificial Sequence: peptide
      containing modified amino acids
<220> FEATURE:
<221> NAME/KEY: MISC_FEATURE
<222> LOCATION: (4)..(4)
<223> OTHER INFORMATION: Xaa is 1-Cha
<220> FEATURE:
<221> NAME/KEY: MOD-RES
<222> LOCATION: (5)..(5)
<223> OTHER INFORMATION: Xaa is 1-Phe-2,3,4,5,6-F

<400> SEQUENCE: 107

Arg Arg Arg Xaa Xaa Arg Ser Pro Ser Tyr Tyr
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: peptide
      containing modified amino acids
<220> FEATURE:
<221> NAME/KEY: MISC_FEATURE
<222> LOCATION: (7)..(7)
<223> OTHER INFORMATION: Xaa is 1-Cha
<220> FEATURE:
<221> NAME/KEY: MOD-RES
<222> LOCATION: (8)..(8)
<223> OTHER INFORMATION: Xaa is 1-Phe-2,3,4,5,6-F

<400> SEQUENCE: 108

Arg Arg Gln Arg Arg Arg Xaa Xaa Arg Ser Pro Ser Tyr Tyr
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (7)..(7)
<223> OTHER INFORMATION: Xaa is 1-Cha
<220> FEATURE:
<221> NAME/KEY: MISC_FEATURE
<222> LOCATION: (8)..(8)
<223> OTHER INFORMATION: Xaa is 1-Phe-2,3,4,5,6-F
<220> FEATURE:
<221> NAME/KEY: MISC_FEATURE
<222> LOCATION: (9)..(9)
<223> OTHER INFORMATION: Xaa is d-Ser
<220> FEATURE:
<221> NAME/KEY: MISC_FEATURE
<222> LOCATION: (10)..(10)
<223> OTHER INFORMATION: Xaa is d-Trp

<400> SEQUENCE: 109

Arg Arg Gln Arg Arg Arg Xaa Xaa Xaa Xaa Pro Ser Tyr
1               5                   10

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: peptide
      containing modified amino acids
<220> FEATURE:
```

```
<221> NAME/KEY: MISC_FEATURE
<222> LOCATION: (12)..(12)
<223> OTHER INFORMATION: Xaa is 1-Cha
<220> FEATURE:
<221> NAME/KEY: MISC_FEATURE
<222> LOCATION: (13)..(13)
<223> OTHER INFORMATION: Xaa is 1-Phe-2,3,4,5,6-F
<220> FEATURE:
<221> NAME/KEY: MISC_FEATURE
<222> LOCATION: (14)..(14)
<223> OTHER INFORMATION: 1-aminoundecanoic acid

<400> SEQUENCE: 110

Tyr Gly Arg Lys Lys Arg Arg Gln Arg Arg Xaa Xaa Xaa Tyr Tyr
1               5                   10                  15

<210> SEQ ID NO 111
<211> LENGTH: 19
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Tyr
<220> FEATURE:
<221> NAME/KEY: MISC_FEATURE
<222> LOCATION: (2)..(2)
<223> OTHER INFORMATION: Xaa is d-Tyr
<220> FEATURE:
<221> NAME/KEY: MISC_FEATURE
<222> LOCATION: (3)..(3)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is 1-Phe-2,3,4,5,6-F
<220> FEATURE:
<221> NAME/KEY: MISC_FEATURE
<222> LOCATION: (8)..(8)
<223> OTHER INFORMATION: Xaa is 1-Cha
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Gln
<220> FEATURE:
<221> NAME/KEY: MISC_FEATURE
<222> LOCATION: (13)..(13)
<223> OTHER INFORMATION: Xaa is d-Arg
<220> FEATURE:
<221> NAME/KEY: MISC_FEATURE
<222> LOCATION: (14)..(14)
<223> OTHER INFORMATION: Xaa is d-Arg
<220> FEATURE:
<221> NAME/KEY: MISC_FEATURE
```

```
<222> LOCATION: (15)..(15)
<223> OTHER INFORMATION: Xaa is d-Lys
<220> FEATURE:
<221> NAME/KEY: MISC_FEATURE
<222> LOCATION: (16)..(16)
<223> OTHER INFORMATION: Xaa is d-Lys
<220> FEATURE:
<221> NAME/KEY: MISC_FEATURE
<222> LOCATION: (17)..(17)
<223> OTHER INFORMATION: Xaa is d-Arg
<220> FEATURE:
<221> NAME/KEY: MISC_FEATURE
<222> LOCATION: (19)..(19)
<223> OTHER INFORMATION: Xaa is d-Tyr

<400> SEQUENCE: 111

Xaa Xaa Xaa Gly Xaa Xaa Xaa Xaa Xaa Xaa Xaa Xaa Xaa Xaa Xaa Xaa
1               5                   10                  15

Xaa Gly Xaa

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Tyr
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Pro
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is d-Pro
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Gln
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (13)..(13)
<223> OTHER INFORMATION: Xaa is d-Arg

<400> SEQUENCE: 112

Xaa Xaa Xaa Trp Ser Xaa Xaa Xaa Xaa Xaa Xaa Xaa Xaa
1               5                   10
```

```
<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Tyr
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Gln
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (13)..(13)
<223> OTHER INFORMATION: Xaa is d-Arg

<400> SEQUENCE: 113

Xaa Xaa Pro Trp Ser Xaa Pro Xaa Xaa Xaa Xaa Xaa Xaa
1               5                   10

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (3)..(3)
<223> OTHER INFORMATION: Xaa is 1-aminoundecanoic acid
<220> FEATURE:
<221> NAME/KEY: MISC_FEATURE
<222> LOCATION: (4)..(4)
<223> OTHER INFORMATION: Xaa is d-Phe 2,3,4,5,6-F
<220> FEATURE:
<221> NAME/KEY: MISC_FEATURE
<222> LOCATION: (5)..(5)
<223> OTHER INFORMATION: Xaa is d-Cha
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Arg
```

```
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Gln
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Lys
<220> FEATURE:
<221> NAME/KEY: MISC_FEATURE
<222> LOCATION: (13)..(13)
<223> OTHER INFORMATION: Xaa is d-Lys
<220> FEATURE:
<221> NAME/KEY: MISC_FEATURE
<222> LOCATION: (14)..(14)
<223> OTHER INFORMATION: Xaa is d-Arg
<220> FEATURE:
<221> NAME/KEY: MISC_FEATURE
<222> LOCATION: (16)..(16)
<223> OTHER INFORMATION: Xaa is d-Tyr

<400> SEQUENCE: 114

Tyr Tyr Xaa Xaa Xaa Xaa Xaa Xaa Xaa Xaa Xaa Xaa Xaa Xaa Gly Xaa
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (2)..(2)
<223> OTHER INFORMATION: Xaa is d-aminoundecanoic acid
<220> FEATURE:
<221> NAME/KEY: MISC_FEATURE
<222> LOCATION: (3)..(3)
<223> OTHER INFORMATION: Xaa is d-Phe-2,3,4,5,6-F
<220> FEATURE:
<221> NAME/KEY: MISC_FEATURE
<222> LOCATION: (4)..(4)
<223> OTHER INFORMATION: Xaa is d-Cha
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Gln
<220> FEATURE:
<221> NAME/KEY: MISC_FEATURE
<222> LOCATION: (9)..(9)
<223> OTHER INFORMATION: Xaa is d-Arg
<220> FEATURE:
```

```
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Lys
<220> FEATURE:
<221> NAME/KEY: MISC_FEATURE
<222> LOCATION: (12)..(12)
<223> OTHER INFORMATION: Xaa is d-Lys
<220> FEATURE:
<221> NAME/KEY: MISC_FEATURE
<222> LOCATION: (13)..(13)
<223> OTHER INFORMATION: Xaa is d-Arg
<220> FEATURE:
<221> NAME/KEY: MISC_FEATURE
<222> LOCATION: (15)..(15)
<223> OTHER INFORMATION: Xaa is d-Tyr

<400> SEQUENCE: 115

Tyr Xaa Xaa Xaa Xaa Xaa Xaa Xaa Xaa Xaa Xaa Xaa Xaa Gly Xaa
1               5                   10                  15

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (2)..(2)
<223> OTHER INFORMATION: Xaa is l-aminoundecanoic acid
<220> FEATURE:
<221> NAME/KEY: MISC_FEATURE
<222> LOCATION: (3)..(3)
<223> OTHER INFORMATION: Xaa is d-Phe-2,3,4,5,6-F
<220> FEATURE:
<221> NAME/KEY: MISC_FEATURE
<222> LOCATION: (4)..(4)
<223> OTHER INFORMATION: Xaa is d-Cha

<400> SEQUENCE: 116

Tyr Xaa Xaa Xaa
1

<210> SEQ ID NO 117
<211> LENGTH: 14
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is l-aminoundecanoic acid
<220> FEATURE:
<221> NAME/KEY: MISC_FEATURE
<222> LOCATION: (2)..(2)
<223> OTHER INFORMATION: Xaa is l-Phe-2,3,4,5,6-F
<220> FEATURE:
<221> NAME/KEY: MISC_FEATURE
<222> LOCATION: (3)..(3)
<223> OTHER INFORMATION: Xaa is d-Cha
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
```

```
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Gln
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Lys
<220> FEATURE:
<221> NAME/KEY: MISC_FEATURE
<222> LOCATION: (11)..(11)
<223> OTHER INFORMATION: Xaa is d-Lys
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (14)..(14)
<223> OTHER INFORMATION: Xaa is d-Tyr

<400> SEQUENCE: 117

Xaa Xaa Xaa Xaa Xaa Xaa Xaa Xaa Xaa Xaa Xaa Xaa Gly Xaa
1               5                   10

<210> SEQ ID NO 118
<211> LENGTH: 3
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is 1-aminoundecanoic acid
<220> FEATURE:
<221> NAME/KEY: MISC_FEATURE
<222> LOCATION: (2)..(2)
<223> OTHER INFORMATION: Xaa is d-Phe-2,3,4,5,6-F
<220> FEATURE:
<221> NAME/KEY: MISC_FEATURE
<222> LOCATION: (3)..(3)
<223> OTHER INFORMATION: Xaa is d-Cha

<400> SEQUENCE: 118

Xaa Xaa Xaa
1

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is 1-aminoundecanoic acid
<220> FEATURE:
<221> NAME/KEY: MISC_FEATURE
<222> LOCATION: (2)..(2)
```

```
<223> OTHER INFORMATION: Xaa is d-Phe-2,3,4,5,6-F
<220> FEATURE:
<221> NAME/KEY: MISC_FEATURE
<222> LOCATION: (3)..(3)
<223> OTHER INFORMATION: Xaa is d-Cha
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Gln
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg

<400> SEQUENCE: 119

Xaa Xaa Xaa Xaa Xaa Xaa Xaa Xaa Xaa
 1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is 1-8-aminoundecanoic acid
<220> FEATURE:
<221> NAME/KEY: MISC_FEATURE
<222> LOCATION: (2)..(2)
<223> OTHER INFORMATION: Xaa is d-Cha
<220> FEATURE:
<221> NAME/KEY: MISC_FEATURE
<222> LOCATION: (3)..(3)
<223> OTHER INFORMATION: Xaa is d-Phe-2,3,4,5,6-F
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Gln
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
```

```
<400> SEQUENCE: 120

Xaa Xaa Xaa Xaa Xaa Xaa Xaa Xaa Xaa
1               5

<210> SEQ ID NO 121
<211> LENGTH: 2
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Phe-2,3,4,5,6-F
<220> FEATURE:
<221> NAME/KEY: MISC_FEATURE
<222> LOCATION: (2)..(2)
<223> OTHER INFORMATION: Xaa is d-Cha

<400> SEQUENCE: 121

Xaa Xaa
1

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Cha
<220> FEATURE:
<221> NAME/KEY: MISC_FEATURE
<222> LOCATION: (2)..(2)
<223> OTHER INFORMATION: Xaa is d-Phe-2,3,4,5,6-F
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Gln
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg

<400> SEQUENCE: 122

Xaa Xaa Xaa Xaa Xaa Xaa Xaa Xaa
1               5

<210> SEQ ID NO 123
<211> LENGTH: 13
<212> TYPE: PRT
<213> ORGANISM: Artificial Sequence
```

```
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Tyr
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Ser
<220> FEATURE:
<221> NAME/KEY: MISC_FEATURE
<222> LOCATION: (4)..(4)
<223> OTHER INFORMATION: Xaa is d-Trp
<220> FEATURE:
<221> NAME/KEY: MISC_FEATURE
<222> LOCATION: (5)..(5)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Gln
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (13)..(13)
<223> OTHER INFORMATION: Xaa is d-Arg

<400> SEQUENCE: 123

Xaa Xaa Xaa Xaa Xaa Xaa Xaa Xaa Xaa Xaa Xaa Xaa Xaa
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Tyr
<220> FEATURE:
<221> NAME/KEY: MISC_FEATURE
<222> LOCATION: (2)..(2)
<223> OTHER INFORMATION: Xaa is d-Bpa
<220> FEATURE:
<221> NAME/KEY: MISC_FEATURE
```

```
<222> LOCATION: (3)..(3)
<223> OTHER INFORMATION: Xaa is d-Ser
<220> FEATURE:
<221> NAME/KEY: MISC_FEATURE
<222> LOCATION: (4)..(4)
<223> OTHER INFORMATION: Xaa is d-Trp
<220> FEATURE:
<221> NAME/KEY: MISC_FEATURE
<222> LOCATION: (5)..(5)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Gln
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (13)..(13)
<223> OTHER INFORMATION: Xaa is d-Arg

<400> SEQUENCE: 124

Xaa Xaa Xaa Xaa Xaa Xaa Xaa Xaa Xaa Xaa Xaa Xaa Xaa
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is 1-8-aminoundecanoic acid
<220> FEATURE:
<221> NAME/KEY: MISC_FEATURE
<222> LOCATION: (3)..(3)
<223> OTHER INFORMATION: Xaa is d-Cha
<220> FEATURE:
<221> NAME/KEY: MISC_FEATURE
<222> LOCATION: (4)..(4)
<223> OTHER INFORMATION: Xaa is d-Phe-2,3,4,5,6-F
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
```

```
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Gln
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg

<400> SEQUENCE: 125

Xaa Xaa Xaa Xaa Xaa Xaa Xaa Xaa Xaa Xaa
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is Xaa is 1-8-aminoundecanoic acid
<220> FEATURE:
<221> NAME/KEY: MISC_FEATURE
<222> LOCATION: (3)..(3)
<223> OTHER INFORMATION: Xaa is d-Phe-2,3,4,5,6-F
<220> FEATURE:
<221> NAME/KEY: MISC_FEATURE
<222> LOCATION: (4)..(4)
<223> OTHER INFORMATION: Xaa is d-Cha
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Gln
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg

<400> SEQUENCE: 126

Xaa Xaa Xaa Xaa Xaa Xaa Xaa Xaa Xaa Xaa
1               5                   10

<210> SEQ ID NO 127
```

```
<211> LENGTH: 13
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Asp
<220> FEATURE:
<221> NAME/KEY: MISC_FEATURE
<222> LOCATION: (2)..(2)
<223> OTHER INFORMATION: Xaa is d-Bpa
<220> FEATURE:
<221> NAME/KEY: MISC_FEATURE
<222> LOCATION: (3)..(3)
<223> OTHER INFORMATION: Xaa is d-Ser
<220> FEATURE:
<221> NAME/KEY: MISC_FEATURE
<222> LOCATION: (4)..(4)
<223> OTHER INFORMATION: Xaa is d-Trp
<220> FEATURE:
<221> NAME/KEY: MISC_FEATURE
<222> LOCATION: (5)..(5)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Gln
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (13)..(13)
<223> OTHER INFORMATION: Xaa is d-Arg

<400> SEQUENCE: 127

Xaa Xaa Xaa Xaa Xaa Xaa Xaa Xaa Xaa Xaa Xaa Xaa Xaa
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
```

```
<223> OTHER INFORMATION: Xaa is d-Asp
<220> FEATURE:
<221> NAME/KEY: MISC_FEATURE
<222> LOCATION: (3)..(3)
<223> OTHER INFORMATION: Xaa is d-Ser
<220> FEATURE:
<221> NAME/KEY: MISC_FEATURE
<222> LOCATION: (4)..(4)
<223> OTHER INFORMATION: Xaa is d-Trp
<220> FEATURE:
<221> NAME/KEY: MISC_FEATURE
<222> LOCATION: (5)..(5)
<223> OTHER INFORMATION: Xaa is d-Ser
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Gln
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (13)..(13)
<223> OTHER INFORMATION: Xaa is d-Arg

<400> SEQUENCE: 128

Xaa Xaa Xaa Xaa Xaa Xaa Xaa Xaa Xaa Xaa Xaa Xaa Xaa
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Asp
```

```
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg
<220> FEATURE:
<221> NAME/KEY: MISC_FEATURE
<222> LOCATION: (11)..(11)
<223> OTHER INFORMATION: Xaa is d-Gln
<220> FEATURE:
<221> NAME/KEY: MISC_FEATURE
<222> LOCATION: (12)..(12)
<223> OTHER INFORMATION: Xaa is d-Arg
<220> FEATURE:
<221> NAME/KEY: MISC_FEATURE
<222> LOCATION: (13)..(13)
<223> OTHER INFORMATION: Xaa is d-Arg

<400> SEQUENCE: 129

Xaa Xaa Xaa Xaa Xaa Xaa Xaa Xaa Xaa Xaa Xaa Xaa Xaa
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Ser
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Ser
<220> FEATURE:
<221> NAME/KEY: MISC_FEATURE
<222> LOCATION: (5)..(5)
<223> OTHER INFORMATION: Xaa is d-Bpa
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
```

<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 130

Xaa Xaa Xaa Xaa Xaa Xaa Xaa Xaa Xaa Xaa Xaa Xaa
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is 1-8-aminocaprylic acid
<220> FEATURE:
<221> NAME/KEY: MISC_FEATURE
<222> LOCATION: (3)..(3)
<223> OTHER INFORMATION: Xaa is d-Bpa
<220> FEATURE:
<221> NAME/KEY: MISC_FEATURE
<222> LOCATION: (4)..(4)
<223> OTHER INFORMATION: Xaa is d-Cha
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Gln
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Arg

<400> SEQUENCE: 131

Xaa Xaa Xaa Xaa Xaa Xaa Xaa Xaa Xaa Xaa
1               5                   10

<210> SEQ ID NO 132
<211> LENGTH: 12
<212> TYPE: PRT

```
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Pro
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Pro
<220> FEATURE:
<221> NAME/KEY: MISC_FEATURE
<222> LOCATION: (5)..(5)
<223> OTHER INFORMATION: Xaa is d-Phe4NO2
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 132

Xaa Xaa Xaa Xaa Xaa Xaa Xaa Xaa Xaa Xaa Xaa Xaa
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Pro
<220> FEATURE:
<221> NAME/KEY: MISC_FEATURE
<222> LOCATION: (3)..(3)
<223> OTHER INFORMATION: Xaa is d-Trp
<220> FEATURE:
```

```
<221> NAME/KEY: MISC_FEATURE
<222> LOCATION: (4)..(4)
<223> OTHER INFORMATION: Xaa is d-Pro
<220> FEATURE:
<221> NAME/KEY: MISC_FEATURE
<222> LOCATION: (5)..(5)
<223> OTHER INFORMATION: Xaa is d-Phe4NO2
<220> FEATURE:
<221> NAME/KEY: MISC_FEATURE
<222> LOCATION: (6)..(6)
<223> OTHER INFORMATION: Xaa is d-Nal2
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 133

Xaa Xaa Xaa Xaa Xaa Xaa Xaa Xaa Xaa Xaa Xaa Xaa
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Phe4NO2
<220> FEATURE:
<221> NAME/KEY: MISC_FEATURE
<222> LOCATION: (2)..(2)
<223> OTHER INFORMATION: Xaa is d-Pro
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Pro
<220> FEATURE:
<221> NAME/KEY: MISC_FEATURE
<222> LOCATION: (5)..(5)
<223> OTHER INFORMATION: Xaa is d-Phe4NO2
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Arg
<220> FEATURE:
<221> NAME/KEY: MISC_FEATURE
```

```
<222> LOCATION: (8)..(8)
<223> OTHER INFORMATION: Xaa is d-Arg
<220> FEATURE:
<221> NAME/KEY: MISC_FEATURE
<222> LOCATION: (9)..(9)
<223> OTHER INFORMATION: Xaa is d-Arg
<220> FEATURE:
<221> NAME/KEY: MISC_FEATURE
<222> LOCATION: (10)..(10)
<223> OTHER INFORMATION: Xaa is d-Gln
<220> FEATURE:
<221> NAME/KEY: MISC_FEATURE
<222> LOCATION: (11)..(11)
<223> OTHER INFORMATION: Xaa is d-Arg
<220> FEATURE:
<221> NAME/KEY: MISC_FEATURE
<222> LOCATION: (12)..(12)
<223> OTHER INFORMATION: Xaa is d-Arg

<400> SEQUENCE: 134

Xaa Xaa Xaa Xaa Xaa Xaa Xaa Xaa Xaa Xaa Xaa Xaa
1               5                   10

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Bpa
<220> FEATURE:
<221> NAME/KEY: MISC_FEATURE
<222> LOCATION: (2)..(2)
<223> OTHER INFORMATION: Xaa is d-Cys
<220> FEATURE:
<221> NAME/KEY: MISC_FEATURE
<222> LOCATION: (3)..(3)
<223> OTHER INFORMATION: Xaa is d-Trp
<220> FEATURE:
<221> NAME/KEY: MISC_FEATURE
<222> LOCATION: (4)..(4)
<223> OTHER INFORMATION: Xaa is d-Arg
<220> FEATURE:
<221> NAME/KEY: MISC_FEATURE
<222> LOCATION: (5)..(5)
<223> OTHER INFORMATION: Xaa is d-Phe-2,3,4,5,6-F
<220> FEATURE:
<221> NAME/KEY: MISC_FEATURE
<222> LOCATION: (6)..(6)
<223> OTHER INFORMATION: Xaa is d-Cha
<220> FEATURE:
<221> NAME/KEY: MISC_FEATURE
<222> LOCATION: (7)..(7)
<223> OTHER INFORMATION: Xaa is d-Cys

<400> SEQUENCE: 135

Xaa Xaa Xaa Xaa Xaa Xaa Xaa
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Tyr
<220> FEATURE:
```

```
<221> NAME/KEY: MISC_FEATURE
<222> LOCATION: (2)..(2)
<223> OTHER INFORMATION: Xaa is d-Cys
<220> FEATURE:
<221> NAME/KEY: MISC_FEATURE
<222> LOCATION: (3)..(3)
<223> OTHER INFORMATION: Xaa is d-Pro
<220> FEATURE:
<221> NAME/KEY: MISC_FEATURE
<222> LOCATION: (4)..(4)
<223> OTHER INFORMATION: Xaa is d-Trp
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Phe-2,3,4,5,6-F
<220> FEATURE:
<221> NAME/KEY: MISC_FEATURE
<222> LOCATION: (7)..(7)
<223> OTHER INFORMATION: Xaa is d-Cha
<220> FEATURE:
<221> NAME/KEY: MISC_FEATURE
<222> LOCATION: (8)..(8)
<223> OTHER INFORMATION: Xaa is d-Cys

<400> SEQUENCE: 136

Xaa Xaa Xaa Xaa Xaa Xaa Xaa Xaa
 1               5

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: peptide
      containing modified amino acids and d-form amino acids
<220> FEATURE:
<221> NAME/KEY: MISC_FEATURE
<222> LOCATION: (1)..(1)
<223> OTHER INFORMATION: Xaa is d-Arg
<220> FEATURE:
<221> NAME/KEY: MISC_FEATURE
<222> LOCATION: (2)..(2)
<223> OTHER INFORMATION: Xaa is d-Arg
<220> FEATURE:
<221> NAME/KEY: MISC_FEATURE
<222> LOCATION: (3)..(3)
<223> OTHER INFORMATION: Xaa is d-Arg
<220> FEATURE:
<221> NAME/KEY: MISC_FEATURE
<222> LOCATION: (4)..(4)
<223> OTHER INFORMATION: Xaa is d-Gln
<220> FEATURE:
<221> NAME/KEY: MISC_FEATURE
<222> LOCATION: (5)..(5)
<223> OTHER INFORMATION: Xaa is d-Arg
<220> FEATURE:
<221> NAME/KEY: MISC_FEATURE
<222> LOCATION: (6)..(6)
<223> OTHER INFORMATION: Xaa is d-Arg

<400> SEQUENCE: 137

Xaa Xaa Xaa Xaa Xaa Xaa
 1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: peptide
      containing modified amino acids
```

```
<220> FEATURE:
<221> NAME/KEY: MISC_FEATURE
<222> LOCATION: (6)..(6)
<223> OTHER INFORMATION: Xaa is Phe-2,3,4,5,6-F
<220> FEATURE:
<221> NAME/KEY: MISC_FEATURE
<222> LOCATION: (7)..(7)
<223> OTHER INFORMATION: Xaa is Cha

<400> SEQUENCE: 138

Tyr Ser Pro Trp Ser Xaa Xaa
1               5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: peptide
      containing modified amino acids
<220> FEATURE:
<221> NAME/KEY: MISC_FEATURE
<222> LOCATION: (1)..(1)
<223> OTHER INFORMATION: Xaa is Bpa
<220> FEATURE:
<221> NAME/KEY: MISC_FEATURE
<222> LOCATION: (5)..(5)
<223> OTHER INFORMATION: Xaa is Phe-2,3,4,5,6-F
<220> FEATURE:
<221> NAME/KEY: MISC_FEATURE
<222> LOCATION: (6)..(6)
<223> OTHER INFORMATION: Xaa is Cha

<400> SEQUENCE: 139

Xaa Ser Trp Ser Xaa Xaa
1               5
```

PEPTIDES AND PEPTIDOMIMETICS HAVING ANTI-PROLIFERATIVE ACTIVITY AND/OR THAT AUGMENT NUCLEIC ACID DAMAGING AGENTS OR TREATMENTS

RELATED APPLICATIONS

This application claims priority to U.S. Application Ser. No. 60/350,208, filed Jan. 17, 2002.

TECHNICAL FIELD

This invention relates to compounds including peptides and peptidomimetics having anti-cell proliferative activity alone, and in combination with treatments that either directly or indirectly damage nucleic acid (e.g., DNA). The invention compounds are therefore useful for inhibiting cell proliferation and, as such, for treating cell proliferative disorders including cancer. In particular, the invention compounds are useful in treating metastatic and non-metastatic solid or liquid tumors.

BACKGROUND

The cell cycle comprises S phase (DNA replication), M phase (mitosis), and two gap phases (G1 and G2 phases) between S and M phases. Checkpoints in the cell cycle ensure accurate progression, such as monitoring the state of DNA integrity, DNA replication, cell size, and the surrounding environment (Maller, J. L. Curr. Opin. Cell Biol., 3:26 (1991)). It is especially important for multi-cellular organisms to maintain integrity of genome, and there are multiple checkpoints that monitor the state of genome. Among them are G1 and G2 checkpoints existing before DNA replication and mitosis, respectively. It is crucial to correct DNA damage before entering S phase, because once damaged DNA is replicated it often gives rise to mutations (Hartwell, L. Cell, 71: 543 (1992)). Progression through G1 and G2 checkpoints without repairing extensive DNA damage induces apoptosis and/or catastrophe.

Most cancer cells carry abnormalities in G1 checkpoint-related proteins such as p53, Rb, MDM-2, p16$^{INK4}$ and p19$^{ARF}$ (Levine, A. J. Cell, 88:323 (1997)). Alternatively, mutations can cause over-expression and/or over activation of oncogene products, e.g., Ras, MDM-2 and cyclin D, which reduce the stringency of G1 checkpoint. In addition to these mutations, excessive growth factor signaling can be caused by the over expression of growth factors and can reduce the stringency of G1 checkpoint. Together with loss and gain-of-function mutations, continuous activation of growth factor receptors or downstream signal-transducing molecules can cause cell transformation by overriding the G1 checkpoint. Abrogated G1 checkpoint contributes to higher mutation rates and the many mutations observed in cancer cells. As a result, most cancer cells depend on G2 checkpoint for survival against excessive DNA damage (O'Connor and Fan, Prog. Cell Cycle Res., 2:165 (1996)).

The mechanism that promotes the cell cycle G2 arrest after DNA damage is believed to be conserved among species from yeast to human. In the presence of damaged DNA, Cdc2/Cyclin B kinase is kept inactive because of inhibitory phosphorylation of threonine-14 and tyrosine-15 residues on Cdc2 kinase or the protein level of Cyclin B is reduced. At the onset of mitosis, the dual phosphatase Cdc25 removes these inhibitory phosphates and thereby activates Cdc2/Cyclin B kinase. The activation of Cdc2/Cyclin B is equivalent to the onset of M phase.

In fission yeast, the protein kinase Chk1 is required for the cell cycle arrest in response to damaged DNA. Chk1 kinase acts downstream of several rad gene products and is modified by the phosphorylation upon DNA damage. The kinases Rad53 of budding yeast and Cds1 of fission yeast are known to conduct signals from unreplicated DNA. It appears that there is some redundancy between Chk1 and Cds1 because elimination of both Chk1 and Cds1 culminated in disruption of the G2 arrest induced by damaged DNA. Interestingly, both Chk1 and Cds1 phosphorylate Cdc25 and promote Rad24 binding to Cdc25, which sequesters Cdc25 to cytosol and prevents Cdc2/Cyclin B activation. Therefore Cdc25 appears to be a common target of these kinases implying that this molecule is an indispensable factor in the G2 checkpoint.

In humans, both hChk1, a human homologue of fission yeast Chk1, and Chk2/HuCds1, a human homologue of the budding yeast Rad53 and fission yeast Cds1, phosphorylate Cdc25C at serine-216, a critical regulatory site, in response to DNA damage. This phosphorylation creates a binding site for small acidic proteins 14-3-3s, human homologues of Rad24 and Rad25 of fission yeast. The regulatory role of this phosphorylation was clearly indicated by the fact that substitution of serine-216 to alanine on Cdc25C disrupted cell cycle G2 arrest in human cells. However, the mechanism of G2 checkpoint is not fully understood.

SUMMARY

In accordance with the invention, provided are peptides and peptidomimetics having one or more activities for inhibiting cell proliferation, stimulating apoptosis or catastrophe, or treating undesirable cell proliferation or survival, such as that characterized by a cell proliferative disorder. In one embodiment, a contiguous peptide or peptidomimetic sequence includes the following structure: P1, P2, P3, P4, P5, P6 (SEQ ID NO:1) or P6, P5, P4, P3, P2, P1 (SEQ ID NO:2). P1 is Cha, Nal (2), (Phe-2,3,4,5,6-F), (Phe-3,4,5F), (Phe-4CF3), an amino acid that occupies a similar side chain space (e.g., Tyr or Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, quinazoline group in the side chain; P2 is Cha, Nal(2), (Phe-2,3,4,5,6-F), (Phe-3,4,5F), (Phe-4CF3), Bpa, Phe4NO2, an amino acid that occupies a similar side chain space (e.g., Tyr or Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P3, P4, P5 are any amino acid (e.g., P4 is Trp), or wherein one or more of P3, P4, P5 is a simple carbon chain (e.g., 11-aminoundecanoic acid, 10-aminodecanoic acid, 9-aminononanoic acid, 8-aminocaprylic acid, 7-aminoheptanoic acid, 6-aminocaproic acid, or a similar structure with one or more unsaturated carbon bonds) such that the distance between P2 and P6 is about the same as the distance when each of P3, P4, P5 are amino acids; and P6 is Bpa, Phe4NO2, any one amino acid and Tyr (e.g., Ser-Tyr), any one amino acid and Phe (e.g., Ser-Phe), any amino acid, or nothing.

In another embodiment, a contiguous peptide or peptidomimetic sequence includes the following structure: P1, P2, P3, P4, P5, P6 (SEQ ID NO:3); P6, P5, P4, P3, P2, P1 (SEQ ID NO:4); P1, P2, P3, P4, P5, P6, P7, P8, P9, P10, P11, P12 (SEQ ID NO:5); P1, P2, P3, P4, P5, P6, P12, P11, P10, P9, P8, P7 (SEQ ID NO:6); P6, P5, P4, P3, P2, P1, P7, P8, P9, P10, P11, P12 (SEQ ID NO:7); P6, P5, P4, P3, P2, P1, P12, P11, P10, P9, P8, P7 (SEQ ID NO:8); P7, P8, P9, P10, P11, P12, P1, P2, P3, P4, P5, P6 (SEQ ID NO:9); P7, P8, P9, P10, P11, P12, P6, P5, P4, P3, P2, P1 (SEQ ID NO:10); P12, P11, P10, P9, P8, P7, P1, P2, P3, P4, P5, P6 (SEQ ID NO:11); P12, P11, P10, P9, P8, P7, P6, P5, P4, P3, P2, P1 (SEQ ID NO:12); P12, P1, P6, P9, P8, P7, P2, P1 (SEQ ID NO:13); P12, P11, P10, P6, P9, P4, P7, P2, P1 (SEQ ID NO:14); P1, P2, P7, P8, P9, P6, P11, P12 (SEQ ID NO:15); or P1, P2, P7, P4, P9, P6, P10, P11, P12 (SEQ ID NO:16). P1 is Cha, Nal(2), (Phe-2,3,4,5,6-F), (Phe-3,4,5F), (Phe-4CF3), Bpa, Phe4NO2, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P2 is Cha, Nal(2), (Phe-2,3,4,5,6-F), (Phe-3,4,5F), (Phe-4CF3), or an amino acid that occupies a similar side chain space (e.g., Tyr or Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, quinazoline group in the side chain; P3, P4, P5 is any amino acid (e.g., P4 is Trp), or one or more of P3, P4, P5 is a simple carbon chain (e.g., 11-aminoundecanoic acid, 10-aminodecanoic acid, 9-aminononanoic acid, 8-aminocaprylic acid, 7-aminoheptanoic acid, 6-aminocaproic acid, or a similar structure with one or more unsaturated carbon bonds) such that the distance between P2 and P6 is about the same as the distance when each of P3, P4, P5 are amino acids; P6 is Bpa, Phe4NO2, any one amino acid and Tyr (e.g., Ser-Tyr), any one amino acid and Phe (e.g., Ser-Phe); and at least three of P7, P8, P9, P10, P11, P12 are basic amino acids with the rest being any amino acid or absent.

In a further embodiment, a contiguous peptide or peptidomimetic sequence includes the following structure: P1, P2, P3, P4, P5, P6, P7, P8, P9, P10, P11, P12 (SEQ ID NO:17); P12, P11, P10, P9, P8, P7, P6, P5, P4, P3, P2, P1(SEQ ID NO:18); P12, P11, P10, P6, P9, P4, P7, P2, P1(SEQ ID NO:19); or P1, P2, P7, P4, P9, P6, P10, P11, P12 (SEQ ID NO:20). P1 is Cha, Nal(2), (Phe-2,3,4,5,6-F), (Phe-3,4,5F), (Phe-4CF3), Bpa, Phe4NO2, an amino acid that occupies a similar side chain space, or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P2 is Cha, Nal(2), (Phe-2,3,4,5,6-F), (Phe-3,4,5F), (Phe-4CF3), an amino acid that occupies a similar side chain space (e.g., Tyr or Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, quinazoline group in the side chain; P3, P4, P5 are any amino acid (e.g., P4 is Trp), or one or more of P3, P4, P5 is a simple carbon chain (e.g., aminoundecanoic acid or 8-aminocaprylic acid) such that the distance between P2 and P6 is about the same as the distance when each of P3, P4, P5 are amino acids; P6 is Bpa, Phe4NO2, any one amino acid and Tyr (e.g., Ser-Tyr), any one amino acid and Phe (e.g., Ser-Phe), any amino acid, or nothing; and at least three of P7, P8, P9, P10, P11, P12 are basic amino acids with the rest being any amino acid or absent.

In an additional embodiment, a contiguous peptide or peptidomimetic sequence includes the following structure: P1, P2, P3, P4, P5, P6 (SEQ ID NO:21) or P6, P5, P4, P3, P2, P1 (SEQ ID NO:22). P1 is Cha, Nal(2), (Phe-2,3,4,5,6-F), (Phe-3,4,5F), (Phe-4CF3), Bpa, Phe4NO2, Tyr, or Phe; P2 is Cha, Nal(2), (Phe-2,3,4,5,6-F), (Phe-3,4,5F), (Phe-4CF3), Bpa, Phe4NO2, Tyr, or Phe; P3 is Ser, Arg, Cys, Pro, or Asn; P4 is Trp; P5 is Ser, Arg, or Asn; or P3, P4, P5 is a single aminoundecanoic acid or a single 8-aminocaprylic acid; and P6 is Bpa, Phe4NO2, (Ser-Tyr), or (Ser-Phe).

In yet another embodiment, a contiguous peptide or peptidomimetic sequence includes the following structure: P1, P2, P3, P4, P5, P6, P7, P8, P9, P10, P11, P12 (SEQ ID NO:23); P1, P2, P3, P4, P5, P6, P12, P11, P10, P9, P8, P7 (SEQ ID NO:24); P6, P5, P4, P3, P2, P1, P7, P8, P9, P10, P11, P12 (SEQ ID NO:25); P6, P5, P4, P3, P2, P1, P12, P11, P10, P9, P8, P7 (SEQ ID NO:26); P7, P8, P9, P10, P11, P12, P1, P2, P3, P4, P5, P6 (SEQ ID NO:27); P7, P8, P9, P10, P11, P12, P6, P5, P4, P3, P2, P1 (SEQ ID NO:28); P12, P11, P10, P9, P8, P7, P1, P2, P3, P4, P5, P6 (SEQ ID NO:29); P12, P11, P10, P9, P8, P7, P6, P5, P4, P3, P2, P1 (SEQ ID NO:30); P12, P1, P6, P9, P8, P7, P2, P1 (SEQ ID NO:31); P12, P11, P10, P6, P9, P4, P7, P2, P1 (SEQ ID NO:32); P1, P2, P7, P8, P9, P6, P11, P12 (SEQ ID NO:33); or P1, P2, P7, P4, P9, P6, P10, P11, P12 (SEQ ID NO:34). P1 is Cha, Nal(2), (Phe-2,3,4,5,6-F), (Phe-3,4,5F), (Phe-4CF3), Bpa, Phe4NO2, Tyr, or Phe; P2 is Cha, Nal(2), (Phe-2,3,4,5,6-F), (Phe-3,4,5F), (Phe-4CF3), Bpa, Phe4NO2, Tyr, or Phe; P3 is Ser, Arg, Cys, Pro, or Asn; P4 is Trp; P5 is Ser. Arg, or Asn; or P3, P4, P5 is a single aminoundecanoic acid or a single 8-aminocaprylic acid; P6 is Bpa, Phe4NO2, (d-Ser-d-Tyr), or (d-Ser-d-Phe); and at least three of P7, P8, P9, P10, P11, P12 are Arg or Lys with the rest being any amino acid or absent.

In still another embodiment, a contiguous peptide or peptidomimetic sequence includes the following structure: P1, P2, P3, P4, P5, P6, P7, P8, P9, P10, P11, P12 (SEQ ID NO:35); P12, P11, P10, P9, P8, P7, P6, P5, P4, P3, P2, P1 (SEQ ID NO:36); P12, P11, P10, P6, P9, P4, P7, P2, P1 (SEQ ID NO:37); or P1, P2, P7, P4, P9, P6, P10, P11, P12 (SEQ ID NO:38). P1 is Cha, or Nal(2); P2 is (Phe-2,3,4,5,6-F), (Phe-3,4,5F), (Phe-4CF3); P3 is Ser; P4 is Trp; P5 is Ser or Asn; P6 is Bpa, Phe4NO2, (Ser-Tyr), or (Ser-Phe); and at least three of P7, P8, P9, P10, P11, P12 are Arg with the rest being any amino acid or absent.

In yet an additional embodiment, a contiguous peptide or peptidomimetic sequence includes the following structure: P1, P2, P3, P4, P5, P6 (SEQ ID NO:39) or P6, P5, P4, P3, P2, P1 (SEQ ID NO:40). P1 is Cha, or Nal(2); P2 is (Phe-2,3,4,5,6-F), (Phe-3,4,5F) or (Phe-4CF3); P3 is Ser; P4 is Trp; P5 is Ser; and P6 is Bpa, or (Ser-Tyr).

In yet a further embodiment, a contiguous peptide or peptidomimetic sequence comprising the following structure:P1, P2, P3, P4, P5, P6 (SEQ ID NO:41); P6, P5, P4, P3, P2, P1 (SEQ ID NO:42); P1, P2, P3, P4, P5, P6, P7, P8, P9, P10, P11, P12 (SEQ ID NO:43); P1, P2, P3, P4, P5, P6, P12, P11, P10, P9, P8, P7 (SEQ ID NO:44); P6, P5, P4, P3, P2, P1, P7, P8, P9, P10, P11, P12 (SEQ ID NO:45); P6, P5, P4, P3, P2, P1, P12, P11, P10, P9, P8, P7 (SEQ ID NO:46); P7, P8, P9, P10, P11, P12, P1, P2, P3, P4, P5, P6 (SEQ ID NO:47); P7, P8, P9, P10, P11, P12, P6, P5, P4, P3, P2, P1 (SEQ ID NO:48); P12, P11, P10, P9, P8, P7, P1, P2, P3, P4, P5, P6 (SEQ ID NO:49); P12, P11, P10, P9, P8, P7, P6, P5, P4, P3, P2, P1 (SEQ ID NO:50); P12, P11, P6, P9, P8, P7, P2, P1 (SEQ ID NO:51); P12, P11, P10, P6, P9, P4, P7, P2, P1 (SEQ ID NO:52); P1, P2, P7, P8, P9, P6, P11, P12 (SEQ ID NO:53); or P1, P2, P7, P4, P9, P6, P10, P11, P12 (SEQ ID NO:54). P1 is Cha, or Nal(2); P2 is (Phe-2,3,4,5,6-F), (Phe-3,4,5F) or (Phe-4CF3); P3 is any amino acid (e.g., Ser, or Pro); P4 is d- or l-Trp; P5 is any amino acid (e.g., Ser, or Pro); P6 is Bpa or (Ser-Tyr); P7 is Arg; P8 is Arg; P9 is Arg; P10 is Gln or Arg; P11 is Arg; and P12 is d- or l-Arg.

In still further embodiments, a contiguous peptide or peptidomimetic sequence includes the following structure: P1, P2, P3, P4, P5, P6, P7, P8, P9, P10, P11, P12 (SEQ ID NO:55); P12, P11, P10, P9, P8, P7, P6, P5, P4, P3, P2, P1 (SEQ ID NO:56); P12, P11, P10, P6, P9, P4, P7, P2, P1 (SEQ ID NO:57); or P1, P2, P7, P4, P9, P6, P10, P11, P12 (SEQ ID NO:58). P1 is Cha or Nal(2); P2 is (Phe-2,3,4,5,6-F); P3 is Ser; P4 is Trp; P5 is Ser; P6 is Bpa or (Ser-Tyr); P7 is Arg; P8 is Arg; P9 is Arg; P10 is Gln or Arg; P11 is Arg; and P12 is Arg.

In particular aspects, a contiguous peptide or peptidomimetic sequence includes the following structure: (d-Bpa) (d-Ser)(d-Trp)(d-Ser) (d-Phe-2,3,4,5,6-F)(d-Cha)(d-Arg) (d-Arg) (d-Arg) (d-Gln)(d-Arg) (d-Arg) (SEQ ID NO:80); (d-Arg) (d-Arg) (d-Arg) (d-Gln)(d-Arg) (d-Arg) (d-Bpa)(d-Ser)(d-Trp)(d-Ser) (d-Phe-2,3,4,5,6-F) (d-Cha) (SEQ ID NO:100); (d-Bpa) (d-Ser)(d-Trp)(d-Ser) (d-Phe-2,3,4,5,6-F) (d-Cha)(d-Arg) (d-Arg) (d-Gln) (d-Arg) (d-Arg) (d-Arg) (SEQ ID NO:59); (d-Arg) (d-Arg) (d-Gln) (d-Arg) (d-Arg) (d-Arg) (d-Bpa) (d-Ser)(d-Trp)(d-Ser) (d-Phe-2,3,4,5,6-F) (d-Cha) (SEQ ID NO:60); (d-Cha) (d-Phe-2,3,4,5,6-F)(d-Ser)(d-Trp) (d-Ser) (d-Bpa) (d-Arg) (d-Arg) (d-Arg) (d-Gln) (d-Arg) (d-Arg) (SEQ ID NO:61); (d-Arg) (d-Arg) (d-Arg) (d-Gln)(d-Arg) (d-Arg) (d-Cha) (d-Phe-2,3,4,5,6-F)(d-Ser) (d-Trp)(d-Ser)(d-Bpa)(SEQ ID NO:62); (d-Cha)(d-Phe-2,3,4,5,6-F) (d-Ser)(d-Trp) (d-Ser) (d-Bpa) (d-Arg) (d-Arg) (d-Gln) (d-Arg) (d-Arg) (d-Arg) (SEQ ID NO:63); (d-Arg) (d-Arg) (d-Gln) (d-Arg) (d-Arg) (d-Cha) (d-Phe-2,3,4,5,6-F) (d-Ser)(d-Trp) (d-Ser) (d-Bpa) (SEQ ID NO:64); (d-Arg) (d-Arg) (d-Arg) (d-Arg) (d-Arg) (d-Arg) (d-Cha) (d-Phe-2,3,4,5,6-F) (d-Ser) (d-Trp)(d-Ser) (d-Bpa) (SEQ ID NO:65); (d-Cha) (d-Phe-2,3,4,5,6-F) (d-Ser)(d-Trp)(d-Ser) (d-Bpa) (d-Arg)(d-Arg) (d-Arg)(d-Arg) (d-Arg) (d-Arg) (SEQ ID NO:66); (d-Arg) (d-Arg) (d-Arg) (d-Arg) (d-Arg) (d-Arg) (d-Bpa) (d-Ser)(d-Trp)(d-Ser) (d-Phe-2,3,4,5,6-F) (d-Cha) (SEQ ID NO:67); (d-Bpa) (d-Ser) (d-Trp)(d-Ser) (d-Phe-2,3,4,5,6-F)(d-Cha) (d-Arg) (d-Arg) (d-Arg) (d-Arg) (d-Arg) (d-Arg)(SEQ ID NO:68); (d-Arg)(d-Arg)(d-Bpa)(d-Arg)(d-Arg)(d-Arg) (d-Phe-2,3,4,5,6-F) (d-Cha) (SEQ ID NO:69); (d-Cha) (d-Phe-2,3,4,5,6-F) (d-Arg) (d-Arg) (d-Arg) (d-Bpa) (d-Arg)(d-Arg) (SEQ ID NO:70); (d-Arg) (d-Arg) (d-Arg) (d-Bpa) (d-Arg)(d-Trp) (d-Arg) (d-Phe-2,3,4,5,6-F)(d-Cha) (SEQ ID NO:71); (d-Cha) (d-Phe-2,3,4,5,6-F) (d-Arg)(d-Trp) (d-Arg) (d-Bpa) (d-Arg) (d-Arg) (d-Arg) (SEQ ID NO:72); (d-Arg) (d-Arg) (d-Arg) (d-Arg) (d-Bpa) (d-Arg)(d-Trp) (d-Arg) (d-Phe-2,3,4,5,6-F)(d-Cha) (SEQ ID NO:73); (d-Cha) (d-Phe-2,3,4,5,6-F) (d-Arg)(d-Trp) (d-Arg) (d-Bpa) (d-Arg) (d-Arg) (d-Arg) (d-Arg) (SEQ ID NO:74); (d-Arg) (d-Arg) (d-Arg)(d-Bpa)(d-Arg)(d-Arg) (d-Arg) (d-Phe-2,3,4,5,6-F)(d-Cha) (SEQ ID NO:75); or (d-Cha) (d-Phe-2,3,4,5,6-F) (d-Arg) (d-Arg) (d-Arg) (d-Bpa) (d-Arg) (d-Arg) (d-Arg) (SEQ ID NO:76); (d-Bpa) (d-Ser)(d-Trp)(d-Ser)(d-Phe-2,3,4,5,6-F) (d-Cha)(d-Arg) (d-Arg)(d-Arg)(d-Gln)(d-Arg)(d-Arg) (SEQ ID NO:77).

In additional aspects, peptides and peptidomimetic sequences include one or more l-type or d-type residues; a d-residue substituted with an l-residue; or an l-residue substituted with a d-residue.

Peptides and peptidomimetic sequences include one or more of the following activities: inhibits proliferation of a cell; abrogates cell cycle G2 checkpoint of a cell; stimulates apoptosis of a cell; stimulates catastrophe of a cell.

Peptides and peptidomimetic sequences include a sequence having a length from about 6 to about 12, 10 to about 20, 18 to about 25, 25 to about 100, 25 to about 200, or 50 to about 300 residues in length.

Further provided are compositions including peptides and peptidomimetic sequences of the invention. In one embodiment, a composition includes a peptide or peptidomimetic sequence and a nucleic acid damaging agent. In another embodiment, a composition includes a peptide or peptidomimetic sequence and an anti-proliferative agent. In an additional embodiment, a composition includes a pharmaceutically acceptable carrier or excipient and a peptide or peptidomimetic sequence and optionally a nucleic acid damaging agent or an anti-proliferative agent.

Moroever, provided are kits including peptides and peptidomimetic sequences of the invention optionally in combination with a nucleic acid damaging treatment (e.g., a nucleic acid damaging agent), or an anti-proliferative agent. In one embodiment, a kit includes a peptide or peptidomimetic sequence and instructions for use in practicing a method of the invention. In a particular aspect, instructions are for inhibiting cell proliferation.

The invention also provides methods of using the peptides and peptidomimetic sequences of the invention. In one embodiment, a method includes contacting a cell with an amount of a peptide or peptidomimetic sufficient to inhibit proliferation of the cell. In another embodiment, a method includes contacting a cell with a nucleic acid damaging agent or exposing a cell to a nucleic acid damaging treatment.

The invention provides methods of increasing sensitivity of a cell to a nucleic acid damaging agent or treatment. In one embodiment, a method includes contacting the cell with an amount of a peptide or peptidomimetic sufficient to increase sensitivity of the cell to a nucleic acid damaging agent or treatment.

The invention further provides methods of increasing nucleic acid damage to a cell. In one embodiment, a method includes contacting a cell with an amount of a peptide or peptidomimetic sufficient to increase nucleic acid damage of the cell.

In various aspects of the methods of the invention, the cell is a cultured cell, or is present in a subject. In additional aspects, the method further includes contacting the cell with a nucleic acid damaging agent or exposing the cell to a nucleic acid damaging treatment.

The invention moreover provides methods of treating a cell proliferative disorder. In one embodiment, a method includes administering to a subject having or at risk of having a cell proliferative disorder an amount of peptide or peptidomimetic effective to treat the cell proliferative disorder. In particular aspects, the cell proliferative disorder comprises a benign or malignant solid or liquid tumor (e.g., metastatic or non-metatstaic sarcoma or carcinoma, or hematopoietic cancer such as a myeloma, lymphoma or leukemia). In additional particular aspects, at least a part of the cells comprising the cell proliferative disorder is located in blood, breast, lung, thyroid, head or neck, brain, lymph, gastrointestinal tract, nasopharynx, genito-urinary tract, bladder, kidney, pancreas, liver, bone, muscle, or skin.

Invention methods include administration by any route. In particular embodiments, a peptide or peptidomimetic is administered locally, regionally or systemically.

Invention methods include treatments resulting in improving the condition of a subject. In particular embodiments, an improvement includes one or more of decreased cell proliferation, decreased numbers of cells, inhibiting increased cell proliferation, inhibiting increases in numbers of cells, increased apoptosis, or decreased survival, of at least a portion of the cells comprising the cell proliferative disorder.

Invention methods include administering a nucleic acid damaging agent, a nucleic acid damaging treatment, an anti-proliferative agent, or an anti-proliferative treatment to the subject. In particular aspects, the agent or treatment comprises a drug (e.g., a chemotherapeutic drug such as 5-fluorouracil (5-FU), rebeccamycin, adriamycin (ADR), bleomycin (Bleo), pepleomycin, a cisplatin derivative such as cisplatin (CDDP) or oxaliplatin, or camptotecin (CPT)), radiation (e.g., UV radiation, IR radiation, or alpha-, beta- or gamma-radiation), a radioisotope (e.g., $I^{131}$, $I^{125}$, $^{90}Y$, $^{177}Lu$, $^{213}Bi$, or $^{211}At$), environmental shock (e.g., hyperthermia).

µg/ml peptide; 4, 0.78 µg/ml peptide; 5, 1.56 µg/ml peptide; 6, 3.125 µg/ml peptide; 7, 6.25 µg/ml peptide; 8, 12.5 µg/ml peptide; 9, 25 µg/ml peptide; and 10, 50 µg/ml peptide. Peptide sequences are as follows: CBP501, (d-Bpa)(d-Ser)(d-Trp)(d-Ser) (d-Phe-2,3,4,5,6-F)(d-Cha) (d-Arg)(d-Arg)(d-Arg)(d-Gln) (d-Arg) (d-Arg) (SEQ ID NO:80); CBP700, (d-Arg)(d-Arg)(d-Bpa) (d-Arg) (d-Arg) (d-Arg) (d-Phe-2,3, 4,5,6-F) (d-Cha) (SEQ ID NO:96); CBP701, (d-Arg) (d-Arg) (d-Arg) (d-Bpa) (d-Arg)(d-Trp) (d-Arg) (d-Phe-2,3, 4,5,6-F)(d-Cha) (SEQ ID NO:97); CBP702, (d-Arg) (d-Arg) (d-Arg) (d-Arg) (d-Bpa) (d-Arg)(d-Trp) (d-Arg) (d-Phe-2,3, 4,5,6-F)(d-Cha) (SEQ ID NO:98); CBP703, (d-Arg) (d-Arg) (d-Arg)(d-Bpa) (d-Arg) (d-Arg) (d-Arg) (d-Phe-2,3,4,5,6-F) (d-Cha) (SEQ ID NO:99).

Figure 12:
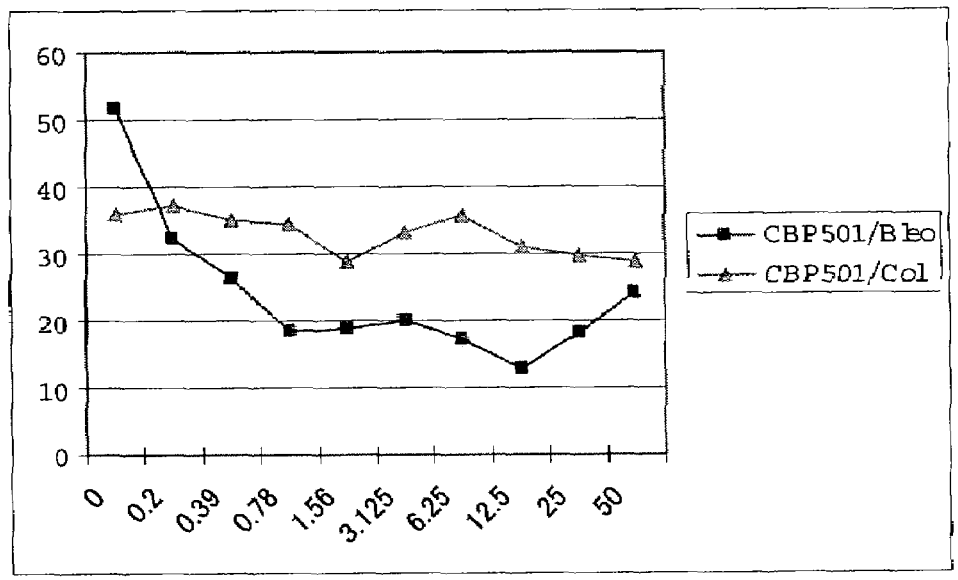

FIG. 12 shows a comparison between G2 abrogating activity and M abrogating activity and/or non specific toxicity of peptides with Bleomycin for G2 abrogation analysis and colchicine for M abrogating activity and/or non specific toxicity. Indicated peptides were added to Jurkat cells with bleomycin or colchicine. The % G2/M cells is indicated on the Y-axis. X-axis is as follows: 1, Bleomycin or Colchicine alone; 2, 0.2 µg/ml peptide; 3, 0.39 µg/ml peptide; 4, 0.78 µg/ml peptide; 5, 1.56 µg/ml peptide; 6, 3.125 µg/ml peptide; 7, 6.25 µg/ml peptide; 8, 12.5 µg/ml peptide; 9, 25 µg/ml peptide; and 10, 50 µg/ml peptide. Peptide sequence is as follows: CBP501, (d-Bpa)(d-Ser)(d-Trp)(d-Ser) (d-Phe-2,3, 4,5,6-F)(d-Cha) (d-Arg)(d-Arg)(d-Arg)(d-Gln) (d-Arg) (d-Arg) (SEQ ID NO:80).

DETAILED DESCRIPTION

The invention provides compounds including peptides and peptidomimetics that inhibit cell proliferation. The invention compounds are therefore useful for treating cell proliferative disorders or physiological conditions characterized by undesirable or unwanted cell proliferation, such as benign and malignant tumor cells. The ability of invention peptides and peptidomimetics to inhibit cell proliferation appears to be due at least in part to abrogation of the cell cycle G2 checkpoint. Because cells can be induced to enter the cell cycle G2 checkpoint in response to nucleic acid damage to allow the cell to repair the damage before DNA replication and cell division occurs, by inhibiting the G2 checkpoint, invention peptides and peptidomimetics sensitize cells to nucleic acid damaging agents and treatment protocols. Cells that accumulate enough nucleic acid damage will be unable to complete repair of the damaged nucleic acid because the G2 checkpoint is disrupted. Such cells will exhibit decreased proliferation (e.g., due to mutation of a gene critical for survival that is not repaired) and eventually undergo apoptosis.

Cells having a normal G1 are less susceptible to accumulating damaged nucleic acid since nucleic acid repair can also take place during G1. Thus, normal cells are less susceptible to the effects of the invention compounds. However, cells having an impaired or disrupted cell cycle G1 checkpoint are more likely to accumulate damaged nucleic acid because the G1 checkpoint is impaired or disrupted making it less likely that the cells can completely repair the damaged nucleic acid. Thus, treating G1 impaired or disrupted cells with an invention peptide or peptidomimetic that disrupts the G2 checkpoint makes the cells even less likely to be able to complete repair of the damaged nucleic acid. G1 impaired or disrupted cells are therefore particularly sensitive to such invention peptides and peptidomimetics. Thus, invention compounds including peptides and peptidomimetics can be used to inhibit or prevent cell proliferation in general and in particular inhibit proliferation of cells having an impaired or disrupted GI checkpoint.

Cells having an impaired or disrupted G1 cell cycle checkpoint include but are not limited to cells that rapidly proliferate. Cell proliferative disorders and physiological conditions characterized by rapidly growing cells, undesirably growing cells or cells that survive instead of undergoing apoptosis frequently have impaired or disrupted G1 cell cycle checkpoint. Thus, as it appears that the ability of invention peptides and peptidomimetics to inhibit proliferation or stimulate apoptosis is due, at least in part, to disrupting the G2 cell cycle checkpoint, cells that rapidly or undesirably proliferate due to an impaired or disrupted G1 checkpoint are particularly attractive targets.

Invention compounds including peptides and peptidomimetics may also suppress cell proliferation by themselves without additional treatments that damage nucleic acid or that have anti-proliferative activty since disrupting G2 checkpoint will likely lead to the accumulation of nucleic acid damage as the cells divide. Accordingly, abnormal or undesirably proliferating or surviving cells can be treated with a compound of the invention alone, or in combination with a nucleic acid damaging treatment (e.g., a chemical agent or treatment protocol), to inhibit or prevent proliferation of the cells or to stimulate cell apoptosis/catastrophe.

Unlike conventional anti-cell proliferative agents, which target rapidly proliferating cells irrespective of whether the cells are normal or abnormal (e.g., cancer cell), invention compounds preferentially target cells having an impaired or disrupted cell cycle G1 checkpoint. For example, CBP501, unlike cisplatin, does not affect the growth of HUVEC cells (see, e.g., Table 3). CBP501 also does not affect M phase cell cycle arrest and/or non specific toxicity induced by colchicine (see, e.g., FIG. 12). Consequently, invention compounds are less likely to produce excess undesirable side effects associated with conventional anti-cell proliferative treatment agents, such as bone marrow suppression, nausea, loss of appetite, diarrhea, and hair loss. In addition, because the vast majority of cancer cells have an impaired or disrupted cell cycle G1 checkpoint, cancer cells will exhibit increased sensitivity to invention compounds that abrogate cell cycle G2 checkpoint. That normal cells are less susceptible also means that invention compounds including peptides and peptidomimetics can be used in greater amounts.

In accordance with the invention, there are provided compounds including peptides and peptidomimetics having anti-cell proliferative activity and/or that abrogate the G2 cell cycle checkpoint. The peptides or peptidomimetics include sequences that inhibit proliferation of a cell or that stimulate apoptosis of a cell. The peptides or peptidomimetics also include sequences that abrogate cell cycle G2 checkpoint. In one embodiment, a contiguous peptide or peptidomimetic sequence includes the following structure: P1, P2, P3, P4, P5, P6 (SEQ ID NO:1) or P6, P5, P4, P3, P2, P1 (SEQ ID NO:2); wherein P1 is d- or l-Cha, d- or l-Nal(2), d- or l-(Phe-2,3,4,5,6-F), d- or l-(Phe-3,4,5F), d- or l-(Phe-4CF3), an amino acid that occupies a similar side chain space (e.g., d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene group, benzofuran, benzothiophene, quinoline, indoline, chroman, quinoxaline, quinazoline group in the side chain; P2 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe4NO2, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4; P6 is d- or l-Bpa, d- or l-Phe4NO2, any amino acid and d- or l-Tyr (e.g., d-Ser-d-Tyr), any amino acid and d- or l-Phe (e.g., d-Ser-d-Phe), any amino acid, or nothing. In various aspects, the amino acid having a simple carbon chain is d- or l-11-aminoundecanoic acid, d- or l-10-aminodecanoic acid, d- or l-9-aminononanoic acid, d- or l-8-aminocaprylic acid, d- or l-7-aminoheptanoic acid, d- or l-6-aminocaproic acid, or a similar structure with one or more unsaturated carbon bonds.

In another embodiment, a contiguous peptide or peptidomimetic sequence includes the following structure: P1, P2, P3, P4, P5, P6 (SEQ ID NO:3); P6, P5, P4, P3, P2, P1 (SEQ ID NO:4); P1, P2, P3, P4, P5, P6, P7, P8, P9, P10, P11, P12 (SEQ ID NO:5); P1, P2, P3, P4, P5, P6, P12, P11, P10, P9, P8, P7 (SEQ ID NO:6); P6, P5, P4, P3, P2, P1, P7, P8, P9, P10, P11, P12 (SEQ ID NO:7); P6, P5, P4, P3, P2, P1, P12, P11, P10, P9, P8, P7 (SEQ ID NO:8); P7, P8, P9, P10, P11, P12, P1, P2, P3, P4, P5, P6 (SEQ ID NO:9); P7, P8, P9, P10, P11, P12, P6, P5, P4, P3, P2, P1 (SEQ ID NO:10); P12, P11, P10, P9, P8, P7, P1, P2, P3, P4, P5, P6 (SEQ ID NO:11); P12, P11, P10, P9, P8, P7, P6, P5, P4, P3, P2, P1 (SEQ ID NO:12); P12, P11, P6, P9, P8, P7, P2, P1 (SEQ ID NO:13); P12, P11, P10, P6, P9, P4, P7, P2, P1 (SEQ ID NO:14); P1, P2, P7, P8, P9, P6, P11, P12 (SEQ ID NO:15); or P1, P2, P7, P4, P9, P6, P10, P11, P12 (SEQ ID NO:16); wherein P1 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe4NO2, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P2 is d- or l-Cha, d- or l-Nal(2), d- or l-(Phe-2,3,4,5,6-F), d- or l-(Phe-3,4,5F), d- or l-(Phe-4CF3), or an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene group, benzofuran, benzothiophene, quinoline, indoline, chroman, quinoxaline, quinazoline group(s) in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4); P6 is d- or l-Bpa, d- or l-Phe4NO2, any amino acid and d- or l-Tyr (e.g., d-Ser-d-Tyr), any amino acid and d- or l-Phe (e.g., d-Ser-d-Phe), and at least three of P7, P8, P9, P10, P11, P12 are basic amino acids with the rest being any amino acid or absent. In various aspects, the amino acid having a simple carbon chain is d- or l-11-aminoundecanoic acid, d- or l-10-aminodecanoic acid, d- or l-9-aminononanoic acid, d- or l-8-aminocaprylic acid, d- or l-7-aminoheptanoic acid, d- or l-6-aminocaproic acid or a similar structure with one or more unsaturated carbon bonds.

In a further embodiment, a contiguous peptide or peptidomimetic sequence includes the following structure: P1, P2, P3, P4, P5, P6, P7, P8, P9, P10, P 11, P12 (SEQ ID NO:17); P12, P11, P10, P9, P8, P7, P6, P5, P4, P3, P2, P1 (SEQ ID NO:18); P12, P11, P10, P6, P9, P4, P7, P2, P1 (SEQ ID NO:19); or P1, P2, P7, P4, P9, P6, P10, P11, P12 (SEQ ID NO:20); wherein P1 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe4NO2, an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, or quinazoline group in the side chain; P2 is d- or l-Cha, d- or l-Nal(2), d- or l-(Phe-2,3,4,5,6-F), d- or l-(Phe-3,4,5F), d- or l-(Phe-4CF3), an amino acid that occupies a similar side chain space (e.g. d- or l-Tyr, d- or l-Phe), or any amino acid with one or two aromatic, piperidine, pyrazine, pyrimidine, piperazine, morpholine or pyrimidine group(s), or one indole, pentalene, indene, naphthalene, benzofuran, benzothiophene, quinoline, indoline, chroman, quinoxaline, quinazoline group in the side chain; P3, P4, P5 are any amino acid or one or more of P3, P4, P5 is a simple carbon chain such that the distance between P2 and P6 is about the same as the distance when each of P3, P4, P5 are amino acids (d- or l-Trp is an example at P4); P6 is d- or l-Bpa, d- or l-Phe4NO2, any amino acid and d- or l-Tyr (e.g., d-Ser-d-Tyr), any amino acid and d- or l-Phe (e.g., d-Ser-d-Phe), any amino acid, or nothing; and at least three of P7, P8, P9, P10, P11, P12 are basic amino acids with the rest being any amino acid or absent. In various aspects, the amino acid having a simple carbon chain is d- or l-aminoundecanoic acid or d- or l-8-aminocaprylic acid.

In yet another embodiment, a contiguous peptide or peptidomimetic sequence includes the following structure: P1, P2, P3, P4, P5, P6 (SEQ ID NO:21) or P6, P5, P4, P3, P2, P1 (SEQ ID NO:22); wherein P1 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe4NO2, d- or l-Tyr, or d- or l-Phe; P2 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe4NO2, d- or l-Tyr, or d- or l-Phe; P3 is d- or l-serine, d- or l-arginine, d- or l-cysteine, d- or l-proline, or d- or l-asparagine; P4 is d- or l-tryptophan; and P5 is d- or l-serine, d- or l-arginine, or d- or l-asparagine; or P3, P4, P5 is a single d- or l-aminoundecanoic acid or a single d- or l-8-aminocaprylic acid; P6 is d- or l-Bpa, d- or l-Phe4NO2, (d-Ser-d-Tyr), or (d-Ser-d-Phe).

In still another embodiment, a contiguous peptide or peptidomimetic sequence includes the following structure: P1, P2, P3, P4, P5, P6, P7, P8, P9, P10, P11, P12 (SEQ ID NO:23); P1, P2, P3, P4, P5, P6, P12, P11 P, P10, P9, P8, P7 (SEQ ID NO:24); P6, P5, P4, P3, P2, P1, P7, P8, P9, P10, P11, P12 (SEQ ID NO:25); P6, P5, P4, P3, P2, P1, P12, P11, P10, P9, P8, P7 (SEQ ID NO:26); P7, P8, P9, P10, P11, P12, P1, P2, P3, P4, P5, P6 (SEQ ID NO:27); P7, P8, P9, P10, P11, P12, P6, P5, P4, P3, P2, P1 (SEQ ID NO:28); P12, P11, P10, P9, P8, P7, P1, P2, P3, P4, P5, P6 (SEQ ID NO:29); P12, P11, P10, P9, P8, P7, P6, P5, P4, P3, P2, P1 (SEQ ID NO:30); P12, P11, P6, P9, P8, P7, P2, P1 (SEQ ID NO:31); P12, P11, P10, P6, P9, P4, P7, P2, P1 (SEQ ID NO:32); P1, P2, P7, P8, P9, P6, P11, P12 (SEQ ID NO:33); or P1, P2, P7, P4, P9, P6, P10, P11, P12 (SEQ ID NO:34); wherein P1 is d- or l-Cha, Nal(2), d- or l-(Phe-2,3,4,5,6-F), d- or l-(Phe-3,4,5F), d- or l-(Phe-4CF3), d- or l-Bpa, d- or l-Phe4NO2, d- or l-Tyr, or d- or l-Phe; P2 is d- or l-Cha, d- or l-Nal(2), d- or l-(Phe-2,3,4,5,6-F), d- or l-(Phe-3,4,5F), d- or l-(Phe-4CF3), d- or l-Bpa, d- or l-Phe4NO2, d- or l-Tyr, or d- or l-Phe; P3 is d- or l-serine, d- or l-arginine, d- or l-cysteine, d- or l-proline, or d- or l-asparagine; P4 is d- or l-tryptophan; P5 is d- or l-serine, d- or l-arginine, or d- or l-asparagine; or P3, P4, P5 is a single d- or l-aminoundecanoic acid or a single d- or l-8-aminocaprylic acid; P6 is d- or l-Bpa, d- or l-Phe4NO2, (d-Ser-d-Tyr), or (d-Ser-d-Phe); and at least three of P7, P8, P9, P10, P11, P12 are d- or l-Arg or d- or l-Lys with the rest being any amino acid or absent.

In an additional embodiment, a contiguous peptide or peptidomimetic sequence includes the following structure: P1, P2, P3, P4, P5, P6, P7, P8, P9, P10, P11, P12 (SEQ ID NO:35); P12, P 11, P10, P9, P8, P7, P6, P5, P4, P3, P2, P1 (SEQ ID NO:36); P12, P11, P10, P6, P9, P4, P7, P2, P1(SEQ ID NO:37); or P1, P2, P7, P4, P9, P6, P10, P11, P12 (SEQ ID NO:38); wherein P1 is d- or l-Cha, or d- or l-Nal(2); P2 is d- or l-(Phe-2,3,4,5,6-F), d- or l-(Phe-3,4,5F), d- or l-(Phe-4CF3); and at least three of P7, P8, P9, P10, P11, P12 are d- or l-Arg with the rest being any amino acid or absent; P3 is d- or l-serine; P4 is d- or l-tryptophan; P5 is d- or l-serine or d- or l-asparagine; P6 is d- or l-Bpa, d- or l-Phe4NO2, (d- or l-Ser-d- or l-Tyr), or (d- or l-Ser-d- or l-Phe).

In yet an additional embodiment, a contiguous peptide or peptidomimetic sequence includes the following structure: P1, P2, P3, P4, P5, P6 (SEQ ID NO:39) or P6, P5, P4, P3, P2, P1 (SEQ ID NO:40); wherein P1 is d- or l-Cha, or d- or l-Nal(2); P2 is (d- or l-Phe-2,3,4,5,6-F), (d- or l-Phe-3,4,5F) or (d- or l-Phe-4CF3); P3 is d- or l-Ser; P4 is d- or l-Trp; P5 is d- or l-Ser; P6 is d- or l-Bpa, or (d- or l-Ser-d- or l-Tyr).

In a further embodiment, a contiguous peptide or peptidomimetic sequence includes the following structure: P1, P2, P3, P4, P5, P6 (SEQ ID NO:41); P6, P5, P4, P3, P2, P1 (SEQ ID NO:42); P1, P2, P3, P4, P5, P6, P7, P8, P9, P10, P 11, P12 (SEQ ID NO:43); P1, P2, P3, P4, P5, P6, P12, P11, P10, P9, P8, P7 (SEQ ID NO:44); P6, P5, P4, P3, P2, P1, P7, P8, P9, P10, P11, P12 (SEQ ID NO:45); P6, P5, P4, P3, P2, P1, P12, P11, P10, P9, P8, P7 (SEQ ID NO:46); P7, P8, P9, P10, P11, P12, P1, P2, P3, P4, P5, P6 (SEQ ID NO:47); P7, P8, P9, P10, P11, P12, P6, P5, P4, P3, P2, P1 (SEQ ID NO:48); P12, P11, P10, P9, P8, P7, P1, P2, P3, P4, P5, P6 (SEQ ID NO:49); P12, P11, P10, P9, P8, P7, P6, P5, P4, P3, P2, P1 (SEQ ID NO:50); P12, P11, P6, P9, P8, P7, P2, P1 (SEQ ID NO:51); P12, P11, P10, P6, P9, P4, P7, P2, P1 (SEQ ID NO:52); P1, P2, P7, P8, P9, P6, P11, P12 (SEQ ID NO:53); or P1, P2, P7, P4, P9, P6, P10, P11, P12 (SEQ ID NO:54); wherein P1 is d- or l-Cha, or d- or l-Nal(2); P2 is (d- or l-Phe-2,3,4,5,6-F), (d- or l-Phe-3,4,5F) or (d- or l-Phe-4CF3); P3 is any amino acid (e.g., d- or l-Ser, or d- or l-Pro); P4 is d- or l-Trp; P5 is any amino acid (e.g., d- or l-Ser); P7 is d- or l-Arg; P8 is d- or l-Arg; P9 is d- or l-Arg; P10 is d- or l-Gln or d- or l-Arg; P11 is d- or l-Arg; P12 is d- or l-Arg; P6 is d- or l-Bpa or (d- or l-Ser-d- or l-Tyr).

In still another embodiment, a contiguous peptide or peptidomimetic sequence includes the following structure: P1, P2, P3, P4, P5, P6, P7, P8, P9, P10, P11, P12 (SEQ ID NO:55); P12, P11, P10, P9, P8, P7, P6, P5, P4, P3, P2, P1 (SEQ ID NO:56); P12, P11, P10, P6, P9, P4, P7, P2, P1 (SEQ ID NO:57); or P1, P2, P7, P4, P9, P6, P10, P11, P12 (SEQ ID NO:58); wherein P1 is d- or l-Cha or d- or l-Nal(2); P2 is (d- or l-Phe-2,3,4,5,6-F); P3 is d- or l-Ser; P4 is d- or l-Trp; P5 is d- or l-Ser; P7 is d- or l-Arg; P8 is d- or l-Arg; P9 is d- or l-Arg; P10 is d- or l-Gln or d- or l-Arg; P11 is d- or l-Arg; P12 is d- or l-Arg; P6 is d- or l-Bpa or (d- or l-Ser-d- or l-Tyr).

In still further embodiments, a contiguous peptide or peptidomimetic sequence includes the following structure: (d-Bpa) (d-Ser)(d-Trp)(d-Ser) (d-Phe-2,3,4,5,6-F) (d-Cha) (d-Arg) (d-Arg) (d-Arg) (d-Gln)(d-Arg) (d-Arg) (SEQ ID NO:80); (d-Arg) (d-Arg) (d-Arg) (d-Gln)(d-Arg) (d-Arg) (d-Bpa)(d-Ser)(d-Trp)(d-Ser) (d-Phe-2,3,4,5,6-F) (d-Cha) (SEQ ID NO:100); (d-Bpa) (d-Ser)(d-Trp)(d-Ser) (d-Phe-2,3,4,5,6-F)(d-Cha)(d-Arg) (d-Arg) (d-Gln) (d-Arg) (d-Arg) (d-Arg) (SEQ ID NO:59); (d-Arg) (d-Arg) (d-Gln) (d-Arg) (d-Arg) (d-Arg) (d-Bpa) (d-Ser)(d-Trp)(d-Ser) (d-Phe-2,3,4,5,6-F) (d-Cha) (SEQ ID NO:60); (d-Cha) (d-Phe-2,3,4,5,6-F) (d-Ser)(d-Trp)(d-Ser) (d-Bpa) (d-Arg) (d-Arg) (d-Arg) (d-Gln)(d-Arg) (d-Arg) (SEQ ID NO:61); (d-Arg) (d-Arg) (d-Arg) (d-Gln)(d-Arg) (d-Arg) (d-Cha) (d-Phe-2,3,4,5,6-F) (d-Ser)(d-Trp)(d-Ser) (d-Bpa) (SEQ ID NO:62); (d-Cha) (d-Phe-2,3,4,5,6-F) (d-Ser) (d-Trp) (d-Ser) (d-Bpa) (d-Arg) (d-Arg) (d-Gln) (d-Arg) (d-Arg) (d-Arg) (SEQ ID NO:63); (d-Arg) (d-Arg) (d-Gln) (d-Arg) (d-Arg) (d-Arg) (d-Cha) (d-Phe-2,3,4,5,6-F) (d-Ser)(d-Trp)(d-Ser) (d-Bpa) (SEQ ID NO:64); (d-Arg) (d-Arg) (d-Arg) (d-Arg) (d-Arg) (d-Arg) (d-Cha) (d-Phe-2,3,4,5,6-F) (d-Ser) (d-Trp)(d-Ser) (d-Bpa) (SEQ ID NO:65); (d-Cha) (d-Phe-2,3,4,5,6-F) (d-Ser)(d-Trp)(d-Ser) (d-Bpa) (d-Arg) (d-Arg) (d-Arg) (d-Arg) (d-Arg) (SEQ ID NO:66); (d-Arg) (d-Arg) (d-Arg) (d-Arg) (d-Arg) (d-Arg) (d-Bpa) (d-Ser)(d-Trp)(d-Ser) (d-Phe-2,3,4,5,6-F)(d-Cha) (SEQ ID NO:67); (d-Bpa) (d-Ser)(d-Trp)(d-Ser) (d-Phe-2,3,4,5,6-F)(d-Cha) (d-Arg) (d-Arg) (d-Arg) (d-Arg) (d-Arg) (d-Arg) (SEQ ID NO:68); (d-Arg)(d-Arg)(d-Bpa) (d-Arg) (d-Arg) (d-Arg) (d-Phe-2,3,4,5,6-F)(d-Cha) (SEQ ID NO:69); (d-Cha) (d-Phe-2,3,4,5,6-F) (d-Arg) (d-Arg) (d-Arg) (d-Bpa) (d-Arg)(d-Arg) (SEQ ID NO:70); (d-Arg) (d-Arg) (d-Arg) (d-Bpa) (d-Arg)(d-Trp) (d-Arg) (d-Phe-2,3,4,5,6-F)(d-Cha) (SEQ ID NO:71); (d-Cha) (d-Phe-2,3,4,5,6-F) (d-Arg)(d-Trp) (d-Arg) (d-Bpa) (d-Arg) (d-Arg) (d-Arg) (SEQ ID NO:72); (d-Arg) (d-Arg) (d-Arg) (d-Bpa) (d-Arg)(d-Trp) (d-Arg) (d-Phe-2,3,4,5,6-F)(d-Cha) (SEQ ID NO:73); (d-Cha) (d-Phe-2,3,4,5,6-F) (d-Arg)(d-Trp) (d-Arg) (d-Bpa) (d-Arg) (d-Arg) (d-Arg) (d-Arg) (SEQ ID NO:74); (d-Arg) (d-Arg)(d-Arg) (d-Bpa)(d-Arg)(d-Arg) (d-Phe-2,3,4,5,6-F)(d-Cha) (SEQ ID NO:75); or (d-Cha) (d-Phe-2,3,4,5,6-F) (d-Arg) (d-Arg) (d-Arg) (d-Bpa) (d-Arg)(d-Arg)(d-Arg) (SEQ ID NO:76).

In still additional embodiments, a contiguous peptide or peptidomimetic sequence includes the following structure: (d-Bpa)(d-Ser)(d-Trp)(d-Ser)(d-Phe-2,3,4,5,6-F)(d-Cha)(d-Arg)(d-Arg)(d-Arg)(d-Gln) (d-Arg)(d-Arg) (SEQ ID NO:77).

Invention peptides and peptidomimetics optionally contain a poly-lys and/or arg sequence in order to assist traversing the cell membrane. Because other amino acid sequences (e.g., HIV tat, ligands for cell surface receptors/proteins, etc.) are capable of traversing the membrane and other molecules can be used to facilitate cell entry of G2 abrogating peptides and peptidomimetics (e.g., liposomes, micelles and other lipid molecules, viral and other vectors, electroporation, etc.), including poly-lys and/or poly-arg sequences is optional. Thus, in additional embodiments, the peptides and peptidomimetics do not have a poly-lys and/or arg sequence that assists with cell entry. For example, in two particular embodiments, a minimum sequence without a poly-lys/arg sequence assisting with cell membrane traversal includes P6, P5, P4, P3, P2, P1 e.g., d-Bpa, d-Ser, d-Trp, d-Ser, d-Phe-2,3,4,5,6F, d-Cha (SEQ ID NO:101); and d-Tyr, d-Ser, d-Pro, d-Trp, d-Ser, d-Phe-2,3,4,5,6F, d-Cha (SEQ ID NO: 102). In two additional particular embodiments, a minimum sequence without a poly-lys/arg sequence assisting with cell membrane traversal includes, for example, d-Bpa, d-Cys, d-Trp, d-Ser, d-Phe-2,3,4,5,6F, d-Cha, d-Cys (SEQ ID NO:103); and d-Tyr, d-Cys, d-Pro, d-Tip, d-Ser, d-Phe-2,3,4,5,6F, d-Cha, d-Cys (SEQ ID NO:104); the Cys residues are optionally cyclized.

As discussed, invention compounds have anti-cell proliferative activity or G2 abrogating activity alone. Anti-cell proliferative activity can be increased by combining such invention compounds with treatments that directly or indirectly-cause nucleic acid damage. Anti-cell proliferative activity also can be increased by combining such invention compounds with treatments that inhibit cell proliferation whether or not the treatments damage nucleic acid. The invention therefore further provides compositions including a compound of the invention (e.g., a peptide or peptidomimetic sequence) and a nucleic acid damaging agent, and compositions including a compound of the invention (e.g., a peptide or peptidomimetic sequence) and an anti-proliferative agent.

As used herein, the terms "abrogate the cell cycle G2 checkpoint," "disrupt the cell cycle G2 checkpoint," "impair the cell cycle G2 checkpoint" and grammatical variations thereof, means inhibiting a cell to arrest cell cycle at the G2 checkpoint. A cell in which the cell cycle G2 checkpoint is abrogated exhibits a decrease in the length of time that the cell is in the G2 checkpoint, which can range from absence of G2 checkpoint altogether to a G2 checkpoint having a decrease in duration of minutes, hours, days, weeks or longer under appropriate conditions. Thus, a cell contacted with an invention compound has a G2 checkpoint time shorter in length than the cell normally would have in the absence of the compound. For example, a decrease in the length of G2 checkpoint time would mean that a cell which is in G2 for a certain time, e.g., 4 hours, when contacted with an invention compound, is in G2 for less than 4 hours, e.g., 3.5, 3, 2.5, 2, 1 or fewer hours.

As used herein, the term "apoptosis" refers to programmed cell death, and assciated changes in cell physiology, e.g., nucleic acid fragmentation, caspase activation, etc., as is understood in the art. The term "catastrophe" means cell death resulting from an error in the mitotic process. In catastrophe, there are fewer features present that are characteristic of apoptosis e.g., caspase activation, chromosome condensation, etc.

As used herein, the terms "peptide," "polypeptide" and "protein" are used interchangeably and refer to two or more amino acids covalently linked by an amide bond or non-amide equivalent. The peptides of the invention can be of any length. For example, the peptides can have from about 5 to 100 or more residues, such as, 5 to 12, 12 to 15, 15 to 18, 18 to 25, 25 to 50, 50 to 75, 75 to 100, or more in length. The peptides of the invention include 1- and d-isomers, and combinations of 1- and d-isomers. The peptides can include modifications typically associated with post-translational processing of proteins, for example, cyclization (e.g., disulfide or amide bond), phosphorylation, glycosylation, carboxylation, ubiquitination, myristylation, or lipidation.

Peptides disclosed herein further include compounds having amino acid structural and functional analogues, for example, peptidomimetics having synthetic or non-natural amino acids or amino acid analogues, so long as the mimetic has one or more functions or activities. The compounds of the invention therefore include "mimetic" and "peptidomimetic" forms.

As used herein, the terms "mimetic" and "peptidomimetic" refer to a synthetic chemical compound which has substantially the same structural and/or functional characteristics of the peptides of the invention. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the mimetic's activity. As with polypeptides of the invention which are conservative variants, routine testing can be used to determine whether a mimetic has the requisite activity, e.g., that it has detectable cell cycle G2 checkpoint abrogating activity. A mimetic, when administered to a subject or contacted on a cell, that detectably disrupts the G2 cell cycle checkpoint, would therefore have G2 checkpoint abrogating activity.

Peptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., a beta turn, gamma turn, beta sheet, alpha helix conformation, and the like. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267–357, "Peptide and Backbone Modifications," Marcel Decker, N.Y.).

As discussed, a peptide can be characterized as a mimetic by containing one or more non-natural residues in place of a naturally occurring amino acid residue. Non-natural residues are known in the art. Particular non-limiting examples of non-natural residues useful as mimetics of natural amino acid residues are mimetics of aromatic amino acids include, for example, D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole(alkyl)alanines; and D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid that can be used in place a natural aromatic rings include, for example, thiazolyl, thiophenyl, pyrazolyl, benzimidazolyl, naphthyl, furanyl, pyrrolyl, and pyridyl aromatic rings.

Mimetics of acidic amino acids can be generated by substitution with non-carboxylate amino acids while maintaining a negative charge; (phosphono)alanine; and sulfated threonine. Carboxyl side groups (e.g., aspartyl or glutamyl) can also be selectively modified by reaction with carbodiimides (R'—N—C—N—R') including, for example, 1-cyclohexyl-3(2-morpholinyl-(4-ethyl) carbodiimide or 1-ethyl-3(4-azonia-4,4-dimetholpentyl) carbodiimide.

Aspartyl or glutamyl groups can also be converted to asparaginyl and glutaminyl groups by reaction with ammonium ions.

Mimetics of basic amino acids can be generated by substitution, for example, in addition to lysine and arginine, with the amino acids ornithine, citrulline, or (guanidino)-acetic acid, or (guanidino)alkyl-acetic acid, where alkyl can be substituted or unsubstituted methyl, ethyl, propyl, hexyl, butyl, pentyl, isopropyl, iso-butyl, sec-isotyl, iso-pentyl, or a non-acidic amino acid. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine mimetics can be generated by reacting arginyl with one or more reagents including, for example, phenylglyoxal, 2,3-butanedione, 1,2-cyclohexanedione, or ninhydrin, optionally under alkaline conditions. Tyrosine residue mimetics can be generated by reacting tyrosyl with aromatic diazonium compounds or tetranitromethane. N-acetylimidizol and tetranitromethane can be used to form O-acetyl tyrosyl species and 3-nitro derivatives, respectively.

Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methytisourea, 2,4, pentanedione, and transamidase-catalyzed reactions with glyoxylate.

Methionine mimetics can be generated by reaction with methionine sulfoxide. Proline mimetics of include, for example, pipecolic acid, thiazolidine carboxylic acid, 3- or 4-hydroxy proline, dehydroproline, 3- or 4-methylproline, and 3,3,-dimethylproline. Histidine mimetics can be generated by reacting histidyl with diethylprocarbonate or para-bromophenacyl bromide. Other mimetics include, for example, those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D-amino acid, but which can additionally be referred to as the R- or S-form.

Invention peptides and peptidomimetics further include modified forms of the sequences set forth herein, provided that the modified form retains, at least a part of, the function of the unmodified or reference peptide or peptidomimetic. For example, a modified peptide or peptidomimetic will retain at least a part of cell proliferative inhibiting or G2 abrogating activity, but may have increased or decreased cell proliferative inhibiting or G2 abrogating activity relative to reference peptide or peptidomimetic.

Modified peptides and peptidomimetics can have one or more amino acid residues substituted with another residue, added to the sequence or deleted from the sequence. In one embodiment, the modified peptide or peptidomimetic has one or more amino acid substitutions, additions or deletions (e.g., 1–3,3–5, 5–10 or more). In one aspect, the substitution is with an amino acid or mimetic whose side chain occupies a similar space with the reference amino acid or mimetic (the amino acid or mimetic that is being substituted). In still another aspect, the substitution is with a non-human amino acid which is structurally similar to the human residue. In a particular aspect, the substitution is a conservative amino acid substitution.

As used herein, the term "similar space" means a chemical moiety that occupies a three-dimensional space similar in size to a reference moiety. Typically, a moiety that occupies a similar space will be similar in size to the reference moiety. An amino acid or mimetic that "occupies a similar side chain space" has a side chain that occupies a three-dimensional space similar in size to the reference amino acid or mimetic. Specific examples for d-(Phe-2,3,4,5,6-F), l-(Phe-2,3,4,5,6-F), d-(Phe-3,4,5F), l-(Phe-3,4,5F), d-(Phe-4CF3) or l-(Phe-4CF3), are (1 or d-Phe-2R1,3R2,4R3,5R4,6R5) where R1,R2,R3,R4,R5 can be chloride, bromide, fluoride, iodide, hydrogen, hydrogen oxide or absent. For small molecules, e.g., fluoride which has a size of about 1 Angstrom, similar space may be absence of a moiety.

The term "conservative substitution" means the replacement of one amino acid by a biologically, chemically or structurally similar residue. Biologically similar means that the substitution is compatible with biological activity, e.g., anti-cell proliferative or G2 abrogating activity. Structurally similar means that the amino acids have side chains with similar length, such as alanine, glycine and serine, or having similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Invention peptides and peptidomimetics therefore include peptides and peptidomimetics having a sequence that is not identical to a sequence of peptides and peptidomimetics sequences set forth in Table 1. In one embodiment, a peptide or peptidomimetic has a sequence having 50%, 60%, 70%, 75%, 80%, 85%, 90%, 95%, or more identity with a sequence set forth in Table 1. In one aspect, the identity is over a defined area of the sequence, e.g., the amino or carboxy terminal 3–5 residues.

The compounds of the invention, including peptides and peptidomimetics can be produced and isolated using any method known in the art. Peptides can be synthesized, whole or in part, using chemical methods known in the art (see, e.g., Caruthers (1980) Nucleic Acids Res. Symp. Ser. 215–223; Horn (1980) Nucleic Acids Res. Symp. Ser. 225–232; and Banga, A. K., Therapeutic Peptides and Proteins, Formulation, Processing and Delivery Systems (1995) Technomic Publishing Co., Lancaster, Pa.). Peptide synthesis can be performed using various solid-phase techniques (see, e.g., Roberge (1995) Science 269:202; Merrifield (1997) Methods Enzymol. 289:3–13) and automated synthesis may be achieved, e.g., using the ABI 431A Peptide Synthesizer (Perkin Elmer) in accordance with the manufacturer's instructions.

Individual synthetic residues and polypeptides incorporating mimetics can be synthesized using a variety of procedures and methodologies known in the art (see, e.g., Organic Syntheses Collective Volumes, Gilman, et al. (Eds) John Wiley & Sons, Inc., NY). Peptides and peptide mimetics can also be synthesized using combinatorial methodologies. Techniques for generating peptide and peptidomimetic libraries are well known, and include, for example, multipin, tea bag, and split-couple-mix techniques (ses, for example, al-Obeidi (1998) Mol. Biotechnol. 9:205–223; Hruby (1997) Curr. Opin. Chem. Biol. 1:114–119; Ostergaard (1997) Mol. Divers. 3:17–27; and Ostresh(1996) Methods Enzymol. 267: 220–234). Modified peptides can be further produced by chemical modification methods (see, for example, Belousov (1997) Nucleic Acids Res. 25:3440–3444; Frenkel (1995) Free Radic. Biol. Med. 19:373–380; and Blommers (1994) Biochemistry 33:7886–7896).

Peptides can also be synthesized and expressed as fusion proteins with one or more additional domains linked thereto for producing a more immunogenic peptide, to more readily isolate a recombinantly synthesized peptide, or to identify and isolate antibodies or antibody-expressing B cells. Domains facilitating detection and purification include, for example, metal chelating peptides such as polyhistidine tracts and histidine-tryptophan modules that allow purification on immobilized metals; protein A domains that allow purification on immobilized immunoglobulin; and the domain utilized in the FLAGS™ extension/affinity purification system (Immunex Corp, Seattle, Wash.) The inclusion of a cleavable linker sequence such as Factor Xa or enterokinase (Invitrogen, San Diego Calif.) between a purification domain and the peptide can be used to facilitate peptide purification. For example, an expression vector can include a peptide-encoding nucleic acid sequence linked to six histidine residues followed by a thioredoxin and an enterokinase cleavage site (see e.g., Williams (1995) Biochemistry 34:1787–1797; Dobeli (1998) Protein Expr. Purif. 12:404–14). The histidine residues facilitate detection and purification of the fusion prtein while the enterokinase cleavage site provides a means for purifying the peptide from the remainder of the fusion protein. Technology pertaining to vectors encoding fusion proteins and application of fusion proteins is known in the art (see e.g., Kroll (1993) DNA Cell. Biol., 12:441–53).

The invention further provides nucleic acids encoding the peptides of the invention. In particular embodiments, a nucleic acid encodes invention peptide sequences having a length of about 8 to 12, 12 to 15, 15 to 18, 15 to 20, 18 to 25, 20 to 25, 25 to 35, 25 to 50 or 50 to 100 amino acids or more in length.

The terms "nucleic acid" and "polynueleotide" are used interchangeably herein to refer to all forms of nucleic acid, including deoxyribonucleic acid (DNA) and ribonucleic acid (RNA). The nucleic acids can be double, single strand, or triplex, linear or circular Nucleic acids include genomic DNA, cDNA, and antisense. RNA nucleic acid can be spliced or unspliced mRNA, rRNA, tRNA or antisense (e.g., RNAi). Nucleic acids of the invention include naturally occurring, synthetic, as well as nucleotide analogues and derivatives. Such altered or modified polynucleotides include analogues that provide nuclease resistance, for example. Nucleic acid lengths also can be less than the exemplified peptide sequences. For example, a subsequence of any of the peptide sequences can encode a peptide having anti-proliferative or G2 abrogating activity.

Nucleic acid can be produced using any of a variety of well known standard cloning and chemical synthesis methods and can be altered intentionally by site-directed mutagenesis or other recombinant techniques known to those skilled in the art. Purity of polynucleotides can be determined through sequencing, gel electrophoresis and the like.

Nucleic acids of the invention may be inserted into a nucleic acid construct in which expression of the nucleic acid is influenced or regulated by an "expression control element," the combination referred to as an "expression cassette." The term "expression control element" means one or more sequence elements that regulates or influences expression of a nucleic acid sequence to which it is operatively linked. An expression control element operatively linked to a nucleic acid sequence controls transcription and, as appropriate, translation of the nucleic acid sequence.

The term "operatively linked" refers to a functional juxtaposition wherein the components so described are in a relationship permitting them to function in their intended manner. Typically expression control elements are juxtaposed at the 5' or at the 3' ends of the gene but can also be intronic. Promoters are generally positioned 5' of the coding sequence. A "promoter" is meant a minimal sequence element sufficient to direct transcription.

Expression control elements include promoters, enhancers, transcription terminators, gene silencers, a start codon (e.g., ATG) in front of a protein-encoding gene. Expression control elements activate constitutive transcription, inducible transcription (i.e., require an external signal for activation), or derepress transcription (i.e., a signal turns transcription off; removing the signal activates transcription). Expression cassettes can also include control elements sufficient to render gene expression controllable for specific cell-types or tissues (i.e., tissue-specific control elements).

Nucleic acids of the invention may be inserted into a plasmid for propagation into a host cell and for subsequent genetic manipulation. A plasmid is a nucleic acid that can be stably propagated in a host cell; plasmids optionally contain expression control elements in order to drive expression of the nucleic acid encoding peptide in the host cell. The term "vector" is used herein synonymously with a plasmid and may also include an expression control element for expression in a host cell. Plasmids and vectors generally contain at least an origin of replication for propagation in a cell and a promoter. Plasmids and vectors are therefore useful for genetic manipulation of peptide encoding nucleic acids, for producing peptides, and for expressing the peptides in host cells or whole organisms, for example.

Peptides may therefore be expressed in bacterial systems using constitutive promoters such as T7, or inducible promoters such as pL of bacteriophage $\pi$, plac, ptrp, ptac (ptrp-lac hybrid promoter); in yeast systems using constitutive promoters such as ADH or LEU2 or an inducible promoter such as GAL (see, e.g., Ausubel et al., In: *Current Protocols in Molecular Biology*, Vol. 2, Ch. 13, ed., Greene Publish. Assoc. & Wiley Interscience, 1988; Grant et al. *Methods in Enzymology,* 153:516 (1987), eds. Wu & Grossman; Bitter *Methods in Enzymology,* 152:673 (1987), eds. Berger & Kimmel, Acad. Press, N.Y.; and, Strathern et al., *The Molecular Biology of the Yeast Saccharomyces* (1982) eds. Cold Spring Harbor Press, Vols. I and II; R. Rothstein In: *DNA Cloning, A Practical Approach*, Vol. 11, Ch. 3, ed. D. M. Glover, IRL Press, Wash., D. C., 1986); in insect cell systems using constitutive or inducible promoters such as ecdysone; and in mammalian cell systems using constitutive promoters such as SV40, RSV, or inducible promoters derived from the genome of mammalian cells such as metallothionein IIA promoter, heat shock promoter, or derived from mammalian virus such as adenovirus late promoter or the inducible mouse mammary tumor virus long terminal repeat. Peptide expression systems further include vectors designed for in vivo use including adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979) and retroviral vectors (U.S. Pat. Nos. 5,624,820, 5,693,508 and 5,674,703 and WIPO publications WO92/05266 and WO92/14829). Bovine papilloma virus (BPV) has also been employed in gene therapy (U.S. Pat. No. 5,719,054). Such gene therapy vectors also include CMV based vectors (U.S. Pat. No. 5,561,063).

The invention therefore also provides nucleic acids encoding peptides of the invention inserted into host cells. In one embodiment, the host cell is a prokaryotic cell. In another embodiment, the host cell is a eukaryotic cell. In various aspects, the eukaryotic cell is a yeast or mammalian (e.g., human, primate, etc.) cell.

As used herein, a "host cell" is a cell into which a nucleic acid is introduced that can be propagated, transcribed, or encoded peptide expressed. The term also includes any progeny of the subject host cell.

Host cells include but are not limited to microorganisms such as bacteria or yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); or animal cell systems infected with recombinant virus expression vectors (e.g., retroviruses, adenovirus, vaccinia virus), or transformed animal cell systems engineered for stable expression, are provided.

The expression vector also can contain a nucleic acid encoding a selectable marker conferring resistance to a selective pressure or identifiable marker (e.g., β-galactosidase), thereby allowing cells having the vector to be identified, grown and expanded. Alternatively, a selectable marker can be on a second vector which is cotransfected into a host cell with a first vector containing an invention polynucleotide. A number of selection systems may be used, including, but not limited to the herpes simplex virus thymidine kinase gene (Wigler et al., Cell 11:223 (1977)), hypoxanthine-guanine phosphoribosyltransferase gene (Szybalska et al., Proc. Natl. Acad. Sci. USA 48:2026 (1962)), and the adenine phosphoribosyltransferase (Lowy et al., Cell 22:817 (1980)) genes can be employed in tk-, hgprt- or aprt- cells respectively. Antimetabolite resistance can be used as the basis of selection for dhfr, which confers resistance to methotrexate (O'Hare et al., Proc. Natl. Acad. Sci. USA 78:1527 (1981)); the gpt gene, which confers resistance to mycophenolic acid (Mulligan et al., Proc. Natl. Acad. Sci. USA 78:2072 (1981)); the neomycin gene, which confers resistance to the aminoglycoside G-418 (Colberre-Garapin et al., J. Mol. Biol. 150:1(1981)); and the hygromycin gene, which confers resistance to hygromycin (Santerre et al., Gene 30:147 (1984)). Additional selectable genes include trpB, which allows cells to utilize indole in place of tryptophan; hisD, which allows cells to utilize histinol in place of histidine (Hartman et al., Proc. Natl. Acad. Sci. USA 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology*, Cold Spring Harbor Laboratory).

As used herein, the terms "nucleic acid damaging treatment" and "nucleic acid damaging agent" means any treatment regimen that directly or indirectly damages nucleic acid (e.g., DNA, cDNA, genomic DNA, mRNA, tRNA or rRNA). Specific examples of such agents include alkylating agents, nitrosoureas, anti-metabolites, plant alkaloids, plant extracts and radioisotopes. Specific examples of agents also include nucleic acid damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochloride (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubibcin (Cerubicine), idarubicin (Idamycin) and epirubicin (Ellence), anthracyclin analogues such as mitoxantrone, actinimycin D, non intercalating topoisomerase inhibitors such as epipodophyllotoxins (etoposide=VP16, teniposide=VM–26), podophylotoxin, bleomycin (Bleo), pepleomycin, compounds that form adducts with nucleic acid including platinum derivatives (e.g., cisplatin (CDDP), trans analogue of cisplatin, carboplatin, iproplatin, tetraplatin and oxaliplatin), camptothecin, topotecan, irinotecan (CPT-11), and SN-38. Specific examples of nucleic acid damaging treatments include radiation (e.g., ultraviolet (UV), infrared (IR), or alpha-, beta- or gamma-radiation) and environmental shock (e.g., hyperthermia).

As used herein, the terms "anti-proliferative treatment" and "anti-proliferative agent" means any treatment regimen that directly or indirectly inhibits proliferation of a cell, virus, bacteria or other unicellular or multicellular organism regardless of whether or not the treatment or agent damages nucleic acid. Particular examples of anti-proliferative agents are anti-tumor and anti-viral drugs, which inhibit cell proliferation or virus proliferation or replication. Specific examples include, inter alia, cyclophosphamide, azathioprine, cyclosporin A, prednisolone, melphalan, chlorambucil, mechlorethamine, busulphan, methotrexate, 6-mercaptopurine, thioguanine, cytosine arabinoside, taxol, vinblastine, vincristine, doxorubicin, actinomycin D, mithramycin, carmustine, lomustine, semustine, streptozotocin, hydroxyurea, cisplatin, mitotane, procarbazine, dacarbazine and dibromomannitol. Anti proliferative agents that cause nucleic acid replication errors or inhibit nucleic acid replication such as nucleoside and nucleotide analogues (e.g., AZT or 5-AZC).

Invention peptides and peptidomimetics can also augment the anti-cell proliferative activity of microtubule stabilizing or destabilizing agents such as vinca alkaloids (vinblastine=VLB, vincristin=VCR, vinorelbine=VRLB, vinflunine=VFL), and taxanes (paclitaxel and docetaxel=taxotare). Thus, such agents may be further included in the compositions of the invention and used in the methods of the invention.

Cells that may be treated with the compounds of the invention include any cell whose proliferation it is desired to inhibit or prevent in vitro, ex vivo or in vivo. Particular target cells exhibit a shorter than normal cell cycle G 1 checkpoint time or have an impaired cell cycle G1 checkpoint such that the cells exit the G1 checkpoint before enough time has passed to complete nucleic acid repair. Candidate cells therefore include cells that rapidly proliferate whether the cells are normal or abnormal. Specific examples are benign or tumorous, metastatic or non-metastatic cells. Additional candidate cells can be identified by measuring their proliferation rate or the length of time that the cells remain in G1 phase. Candidate cells can also be identified by contacting a test cell with an invention compound alone, or in combination with a nucleic acid damaging treatment, and determining if the contacted cell exhibits decreased proliferation or increased cell death or apoptosis/catastrophe.

Invention compounds are therefore useful for inhibiting cell proliferation in vitro, ex vivo and in vivo. As such, subjects having or at risk of having a disorder or physiological condition characterized by abnormal or undesirable or unwanted cell proliferation or cell survival, or abnormal or deficient cell differentiation, can be treated with an invention compound alone or in combination with a treatment that directly or indirectly causes nucleic acid damage or an anti-proliferative treatment.

Thus, in accordance with the invention, there are provided methods for inhibiting cell proliferation, methods for increasing sensitivity of a cell to a nucleic acid damaging agent or treatment and methods for increasing nucleic acid damage to a cell in vitro, ex vivo and in vivo. In one embodiment, a method includes contacting a cell (e.g., a cultured cell or a cell present in a subject) with an amount of an invention peptide or peptidomimetic sufficient to inhibit proliferation of the cell. In another embodiment, a method includes contacting the cell with an amount of an invention peptide or peptidomimetic sufficient to increase sensitivity of the cell to a nucleic acid damaging agent or treatment. In yet another embodiment, a method includes contacting a cell with an amount of an invention peptide or peptidomimetic sufficient to increase nucleic acid damage of the cell. In various aspects, a method further includes contacting the cell with a nucleic acid damaging agent or exposing the cell to a nucleic acid damaging treatment.

Further provided are methods of treating a cell proliferative disorder or differentiative disorder in a subject, including conditions characterized by undesirable or unwanted cell proliferation or cell survival, conditions characterized by deficient or aberrant apoptosis, conditions characterized by aberrant or deficient cell survival, as well as conditions characterized by aberrant or deficient cell differentiation. In one embodiment, a method includes administering to a subject having or at risk of having a cell proliferative disorder, an amount of an invention peptide or peptidomimetic effective to treat the cell proliferative disorder. In one aspect, the amount is sufficient to improve the subjects condition. In particular aspects, the improvement includes, in at least a portion of the target cells (e.g., abnormally proliferating cells), decreased cell proliferation, decreased numbers of cells, inhibiting increases in the number of cells, increased apoptosis, or decreased survival. In yet another aspect, the subject is administered an invention compound prior to, contemporaneously with, or after administering a treatment that inhibits cell proliferation. In additional particular aspects, at least a part of the cells of the cell proliferative disorder are located in blood, breast, lung, thyroid, head or neck, brain, lymph, gastrointestinal tract, genito-urinary tract, kidney, pancreas, liver, bone, muscle, or skin.

In another embodiment, a method includes administering an amount of compound to the subject to treat a solid tumor. In yet another embodiment, a method includes administering an amount of compound to the subject to treat a liquid tumor. In various aspects, the subject having the tumor is administered with an invention compound prior to, contemporaneously with, or after another anti-tumor therapy.

As used herein, the terms "proliferative disorder" and "proliferative condition" mean any pathological or non-pathological physiological condition characterized by aberrant or undesirable proliferation (e.g., of a cell, virus, bacteria, fungus, etc.). The terms "cell proliferative disorder" and "cell proliferative condition" mean any pathological or non-pathological physiological condition characterized by aberrant or undesirable cell proliferation, as well as including conditions characterized by undesirable or unwanted cell proliferation or cell survival (e.g., due to deficient apoptosis), conditions characterized by deficient or aberrant or deficient apoptosis, as well as conditions characterized by aberrant or undesirable or unwanted cell survival. The term "differentiative disorder" means any pathological or non-pathological physiological condition characterized by aberrant or deficient differentiation.

Proliferative or differentiative disorders amenable to treatment include diseases and non-pathological physiological conditions, both benign and neoplastic, characterized by abnormal or undesirable cell numbers, cell growth or cell survival. Such disorders or conditions may therefore constitute a disease state and include all types of cancerous growths or oncogenic processes, metastatic tissues or malignantly transformed cells, tissues, or organs, or may be non-pathologic, i.e., a deviation from normal but which is not typically associated with disease. A specific example of a non-pathologic condition that may be treated in accordance with the invention is tissue re-growth from wound repair that results in scarring.

Cells comprising the proliferative or differentiative disorder may be aggregated in a cell mass or be dispersed. The term "solid tumor" refers to neoplasias or metastases that typically aggregate together and form a mass. Particular examples include visceral tumors such as gastric or colon cancer, hepatomas, venal carcinomas, lung and brain tumors/cancers. A "liquid tumor" refers to neoplasias of the haematopoetic system, such as lymphomas, myelomas and leukemias, or neoplasias that are diffuse in nature, as they do not typically form a solid mass. Particular examples of leukemias include acute and chronic lymphoblastic, myeolblasitc and multiple myeloma.

Such disorders include neoplasms or cancers, which can affect virtually any cell or tissue type, e.g., carcinoma, sarcoma, melanoma, metastatic disorders or haematopoictic neoplastic disorders. A metastatic tumor can arise from a multitude of primary tumor types, including but not limited to breast, lung, thyroid, head and neck, brain, lymphoid, gastrointestinal (mouth, esophagus, stomach, small intestine, colon, rectum), genito-urinary tract (uterus, ovary, cervix, bladder, testicle, penis, prostate), kidney, pancreas, liver, bone, muscle, skin, etc.

Carcinomas refer to malignancies of epithelial or endocrine tissue, and include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the cervix, lung, prostate, breast, head and neck, colon, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Sarcomas refer to malignant tumors of mesenchymal cell origin. Exemplary sarcomas include for example, lymphosarcoma, liposarcoma, osteosarcoma, and fibrosarcoma.

As used herein, the term "haematopoietic proliferative disorder" means a disease involving hyperplastic/neoplastic cells of haematopoietic origin, e.g., arising from myeloid, lymphoid or erythroid lineages, or precursor cells thereof. Typically, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML); lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Treatments for use in combination with the invention compounds include any anti-proliferative, nucleic acid damaging or anti-tumor treatment as disclosed herein or known in the art. For example, an anti-cell proliferative or anti-tumor treatment may comprise radiation treatment or surgical resection optionally in combination with drug treatment. The treatment may comprise administration of a chemical substance, such as a radioisotope, a drug, such as a chemotherapeutic agent, or genetic therapy, such as an anti-oncogene (e.g., Rb, DCC, p53, etc.), a dominant negative oncogene or an antisense to an oncogene. The compounds can be administered prior to, contemporaneously with or following other treatment protocols. For example, a candidate subject for anti-cell proliferative therapy (e.g., radiation therapy, chemotherapy, gene therapy, surgical resection, etc.) can be administered an invention compound prior to initiating the anti-cell proliferative therapy. Thus, prophylactic treatment methods are provided.

The term "subject" refers to animals, typically mammalian animals, such as primates (humans, apes, gibbons, chimpanzees, orangutans, macaques), domestic animals (dogs and cats), farm animals (horses, cattle, goats, sheep, pigs) and experimental animals (mouse, rat, rabbit, guinea pig). Subjects include animal disease models (e.g., tumor bearing mice).

Subjects appropriate for treatment include those currently undergoing or are candidates for treatment for a proliferative or differentiative disorder or (e.g., anti-tumor therapy). Additional candidate subjects include, for example, subjects at risk of developing a cell proliferative disorder. The invention methods are therefore applicable to treating a subject who is at risk of developing a cell proliferative disorder but who has not yet exhibited overt symptoms of the disorder. At risk subjects can be identified as having a genetic predisposition or family history to developing a cell proliferative disorder. For example, subjects having an activated oncogene or having a mutation or deletion of a tumor suppressor gene are candidate subjects. At risk subjects can therefore be identified using routine genetic screening for the presence of the genetic lesion, or inquiry into the subjects' family history to establish that they are at risk of the disorder. A particular example of an at risk subject would be one with a family history or other genetic characteristic indicating predisposition to a cancer in which the neoplastic or drug-resistant neoplastic cells express CD40. A particular specific example of a genetic disease is retinoblastoma, which is caused by a defect in the Rb tumor suppresor gene.

Amounts administered are typically in an "effective amount" or "sufficient amount" that is an amount sufficient to produce the desired affect. Effective amounts therefore include one or more of: decreasing cell proliferation, decreasing numbers of cells, inhibiting increased proliferation, inhibiting increased numbers of cells, increasing apoptosis, or decreasing survival, of at least a portion of the cells comprising the proliferating cells (e.g., at least some of the target cells). Thus, for example, where it is desired to inhibit cell proliferation, an effective amount will be an amount that detectably decreases cell proliferation or numbers of proliferating cells, or increases cell apoptosis or decreases cell survival. The amount can therefore be sufficient to reduce target cell numbers, stabilize target cell numbers or inhibit increases in target cell numbers. For example, where the disorder comprises a solid tumor, reducing tumor size, stabilizing tumor size, or preventing further growth of the tumor, of at least a portion of the tumor (e.g. inhibiting growth of 5–10% of the cells, or 10–20% or more of the cells comprising the tumor mass) is a satisfactory clinical endpoint. Where the disorder comprises a liquid tumor, reducing numbers of tumor cells, stabilizing tumor cell numbers or inhibiting further increases in tumor cell numbers, of at least a subpopulation of the tumor cells (e.g. inhibiting growth of 5–10% of the cells, or 10–20% or more of the cells) is a satisfactory clinical endpoint.

In addition, amounts considered effective can prevent or inhibit progression of the condition or disorder. For example, certain tumors as they progress become increasingly aggressive, including progressing to metastatic forms. Thus, amounts also considered effective would result in reducing or preventing the tumors from becoming increasingly aggressive or from metastasizing. Accordingly, inhibiting or preventing a worsening of the disorder or condition, i.e., stabilizing the condition is an additional satisfactory clinical endpoint.

Examination of a biological sample containing a liquid tumor (e.g., blood or a tissue sample), can establish whether tumor cell mass or numbers have been reduced, or inhibition of tumor cell proliferation has occurred. For a solid tumor, invasive and non-invasive imaging methods can ascertain a reduction in tumor size, or inhibiting increases in the tumor size. Decreasing counts of receptor of a receptor positive tumor, can be used to assess reduction or inhibition of tumor cell proliferation. Amounts of hormone of a hormone producing tumor, e.g., breast, testicular, or ovarian cancers, can be used to assess a reduction or inhibition of proliferation of the tumor.

Effective amounts can also objectively or subjectively reduce or decrease the severity or frequency of symptoms associated with the disorder or condition. For example, an amount of an invention compound that reduces pain, nausea or other discomfort, or increases appetite or subjective well being is a satisfactory clinical endpoint.

Effective amounts also include a reduction of the amount (e.g., dosage) or frequency of treatment with another protocol, which is considered a satisfactory clinical endpoint. For example, a cancer patient treated with an invention compound may require less nucleic acid damaging treatment in order to inhibit cancer cell proliferation. In this example, an effective amount would include an amount that reduces the dosage frequency or amount of a nucleic acid damaging agent that the subject is administered in comparison to the dosage frequency or amount administered without treatment with a compound of the invention.

Methods of the invention that lead to an improvement in the subject's condition or a therapeutic benefit may be relatively short in duration, e.g., the improvement may last several hours, days or weeks, or extend over a longer period of time, e.g., months or years. An effective amount need not be a complete ablation of any or all symptoms of the condition or disorder. Thus, a satisfactory clinical endpoint for an effective amount is achieved when there is a subjective or objective improvement in the subjects' condition as determined using any of the foregoing criteria or other criteria known in the art appropriate for determining the status of the disorder or condition, over a short or long period of time. An amount effective to provide one or more beneficial effects, as described herein or known in the art, is referred to as an "improvement" of the subject's condition or "therapeutic benefit" to the subject.

An effective amount of an invention compound can be determined based upon animal studies or optionally in human clinical trials. The skilled artisan will appreciate the various factors that may influence the dosage and timing required to treat a particular subject including, for example, the general health, age, or gender of the subject, the severity or stage of the disorder or condition, previous treatments, susceptibility to undesirable side effects, clinical outcome desired and the presence of other disorders or conditions. Such factors may influence the dosage and timing required to provide an amount sufficient for therapeutic benefit. The dosage regimen also takes into consideration the pharmacokinetics, i.e., the pharmaceutical composition's rate of absorption, bioavailability, metabolism, and clearance (see, e.g., Egleton (1997) "Bioavailability and transport of peptides and peptide drugs into the brain" Peptides 18:1431–1439; and Langer (1990) Science 249:1527–1533). In addition, doses or treatment protocols may be specifically tailored to the subject or modified based on pharmacogenomic data.

The compounds of the invention can therefore be administered alone or as a pharmaceutical composition, systemically, regionally (e.g., directed towards an organ or tissue, e.g., by injection into the portal vein for treating a cell proliferative disorder of the liver), or locally (e.g., directly into a tumor mass), in accordance with any protocol or route that achieves the desired effect. The compounds and pharmaceutical compositions can be administered as a single or multiple dose each day (e.g., at a low dose), or intermittently (e.g., every other day, once a week, etc. at a higher dose). The compounds and pharmaceutical compositions can be administered via inhalation (e.g., intra-tracheal), orally, intravenously, intraarterially, intravascularly, intrathecally, intraperitonealy, intramuscularly, subcutaneously, intracavity, transdermally (e.g., topical), transmucosally (e.g., buccal, bladder, vaginal, uterine, rectal, or nasal), by multiple administrations, sustained release (e.g., gradual perfusion over time) or a single bolus. Implantable devices, including microfabricated devices, for administering drugs are well known and are also applicable for delivering compounds of the invention to a subject.

Compounds administered intravenously (IV) would be at about 0.01 mg/hr to about 1.0 mg/hr over several hours (typically 1, 3, or 6 hours), which can be repeated for one or more weeks with intermittent cycles. Considerably higher dosages (e.g., ranging up to about 10 mg/ml) can be used, particularly when the drug is administered to a secluded site and not into the blood stream, such as into a body cavity or into a lumen of an organ, e.g., the cerebrospinal fluid (CSF).

The invention therefore further provides pharmaceutical compositions. Such pharmaceutical compositions are useful for administration to a subject in vivo or ex vivo, and for treating a subject with the invention compounds, for example.

As used herein the term "pharmaceutically acceptable" and "physiologically acceptable" includes solvents (aqueous or non-aqueous), solutions, emulsions, dispersion media, coatings, isotonic and absorption promoting or delaying agents, compatible with pharmaceutical administration. A "pharmaceutical composition" or "pharmaceutical formulation" therefore refers to a composition suitable for pharmaceutical use in a subject. The pharmaceutical compositions and formulations include an amount of an invention compound, for example, an effective amount of a peptide or peptidomimetic, nucleic acid encoding same, vector, or cell of the invention, and a pharmaceutically or physiologically acceptable carrier.

Pharmaceutical compositions can be formulated to be compatible with a particular route of administration, systemic or local. Thus, pharmaceutical compositions include carriers, diluents, or excipients suitable for administration by various routes.

Formulations or enteral (oral) administration can be contained in a tablet (coated or uncoated), capsule (hard or soft), microsphere, emulsion, powder, granule, crystal, suspension, syrup or elixir. Conventional nontoxic solid carriers which include, for example, pharmaceutical grades of mannitol, lactose, starch, magnesium stearate, sodium saccharin, talcum, cellulose, glucose, sucrose, magnesium carbonate, can be used to prepare solid formulations. Supplementary active compounds (e.g., preservatives, antibacterial, antiviral and antifungal agents) can also be incorporated into the formulations. A liquid formulation can also be used for enteral administration. The carrier can be selected from various oils including petroleum, animal, vegetable or synthetic, for example, peanut oil, soybean oil, mineral oil, sesame oil. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Pharmaceutical compositions for enteral, parenteral, or transmucosal delivery include, for example, water, saline, phosphate buffered saline, Hank's solution, Ringer's solution, dextrose/saline, and glucose solutions. The formulations can contain auxiliary substances to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. Additional parenteral formulations and methods are described in Bai (1997) J. Neuroimmunol. 80:65–75; Warren (1997) J. Neurol. Sci. 152:31–38; and Tonegawa (1997) J. Exp. Med. 186:507–515. The parenteral preparation can be enclosed in ampules, disposable syringes or multiple dose vials made of glass or plastic.

Pharmaceutical compositions for intradermal or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid, glutathione or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, sodium chloride may be included in the composition. The resulting solutions can be packaged for use as is, or lyophilized, the lyophilized preparation can later be combined with a sterile solution prior to administration.

Pharmaceutically acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760–1764; Samanen (1996) J. Pharm. Pharmacol. 48:119–135; and U.S. Pat. No. 5,391,377, describing lipid compositions for oral delivery of therapeutic agents).

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be through nasal sprays or suppositories (see, e.g., Sayani (1996) "Systemic delivery of peptides and proteins across absorptive mucosae" Crit. Rev. Ther. Drug Carrier Syst. 13:85–184). For transdermal administration, the active compound can be formulated into ointments, salves, gels, or creams as generally known in the art. Transdermal delivery systems can also be achieved using patches.

For inhalation delivery, the pharmaceutical formulation can be administered in the form of an aerosol or mist. For aerosol administration, the formulation can be supplied in finely divided form along with a surfactant and propellant. In another embodiment, the device for delivering the formulation to respiratory tissue is in which the formulation vaporizes. Other delivery systems known in the art include dry powder aerosols, liquid delivery systems, inhalers, air jet nebulizers and propellant systems (see, e.g., Patton (1998) Biotechniques 16:141–143; Dura Pharmaceuticals, San Diego, Calif.; Aradigm, Hayward, Calif.; Aerogen, Santa Clara, Calif.; and Inhale Therapeutic Systems, San Carlos, Calif.).

Biodegradable, biocompatable polymers can be used, such as ethylene vinyl acetate, polyanhydrides, polyglycolic acid, collagen, polyorthoesters, and polylactic acid. Methods for preparation of such formulations are known to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known in the art, for example, as described in U.S. Pat. Nos. 4,235,871; 4,501,728; 4,522,811; 4,837,028; 6,110,490; 6,096,716; 5,283,185; 5,279,833; Akimaru (1995) Cytokines Mol. Ther. 1:197–210;Alving (1995) Immunol. Rev. 145:5–31; and Szoka (1980) Ann. Rev. Biophys. Bioeng. 9:467). Biodegradeable microspheres or capsules or other biodegradeable polymer configurations capable of sustained delivery of small molecules including peptides are known in the art (see, e.g., Putney (1998) Nat. Biotechnol. 16:153–157). Compounds of the invention can be incorporated within micelles (see, e.g., Suntres (1994) J. Pharm. Pharmacol. 46:23–28; Woodle (1992) Pharm. Res. 9:260–265). Peptides can be attached to the surface of the lipid monolayer or bilayer. For example, peptides can be attached to hydrazide-PEG-(distearoylphosphatidyl) ethanolamine-containing liposomes (see, e.g., Zalipsky (1995) Bioconjug. Chem. 6:705–708). Alternatively, any form of lipid membrane, such as a planar lipid membrane or the cell membrane of an intact cell, e.g., a red blood cell, can be used. Liposomal and lipid-containing formulations can be delivered by any means, including, for example, intravenous, transdermal (see, e.g., Vutla (1996) J. Pharm. Sci. 85:5–8), transmucosal, or oral administration.

A pharmaceutically acceptable formulation can incorporate about 1% to 99.9% of active ingredient (e.g., peptide or peptidomimetic). The pharmaceutical compositions can be sterilized by conventional, well-known sterilization techniques, or can be sterile filtered.

Additional pharmaceutical formulations and delivery systems are known in the art and are applicable in the methods and compositions of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky et al., *Drug Delivery Systems*, R. L. Juliano, ed., Oxford, N.Y. (1980), pp. 253–315).

The pharmaceutical formulations can be packaged in unit dosage form for ease of administration and uniformity of dosage. "Unit dosage form" as used herein refers to physically discrete unitary dosages for administration to the subject to be treated; each unit contains a predetermined quantity of compound that produces a desired effect in combination with a pharmaceutical carrier or excipient.

The invention further provides kits including invention compounds and pharmaceutical formulations thereof, optionally packaged into suitable packaging material. A kit typically includes a label or packaging insert including a description of the components or instructions for use in vitro, in vivo, or ex vivo, of the components therein. A kit can contain a collection of such components, e.g., two or more invention compounds or an invention compound in combination with a nucleic acid damaging agent or an anti-proliferative agent.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions. Kits of the invention therefore can additionally include labels or instructions for using the kit components in any method of the invention. Instructions can include instructions for practicing any of the methods of the invention described herein including treatment, detection, monitoring or diagnostic methods. Thus, for example, a kit can include an invention compound in a pack, or dispenser together with instructions for administering the compound in a treatment method of the invention. Instructions may additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, IC tip and hybrids of these such as magnetic/optical storage media.

Invention kits can additionally include a buffering agent, or a preservative or a stabilizing agent in a pharmaceutical formulation. Each component of the kit can be enclosed within an individual container and all of the various containers can be within a single package. Invention kits can be designed for cold storage. The following are abbreviations used herein:

Cha: cyclohexyl-alanine
Phe-2,3,4,5,6-F: Fluorides are at position 2,3,4,5,6,on Phenyl residue of Phenylalanine
F: Fluoride
Bpa: Benzoyl-phenylalanine
Nal(2): 2-Naphthyl-alanyl
Ala(3-Bzt): (3-Benzothienyl)-Alanine
Nal(1): 1-Naphthyl-alanyl
Dph: Diphenyl-Alanine
Ala(tBu): t-Butyl-alanyl
Cys(tBu): t-Butyl-cysteine
Phe-3,4,5-F: Fluorides are at position 3,4,5 on the Phenyl of Phenylalanine
Phe-4CF3: CF3 is at position 4 on Phenyl residue of Phenylalanine
Phe-3Br,4Cl,5Br: Bromide is at position 3, Chloride is at position 4, and Bromide is at position 5 on the Phenyl of Phenylalanine
Phe-4Cl: Chloride is at position 4 on the Phenyl of Phenylalanine P1, P2, P3, P4, P5, P6, etc., and (P1, P2, P3, P4, P5, P6, etc.); and P7, P8, P9, P10, P11, P12, etc., and (P7, P8, P9, P10, P11, P12, etc.): contiguous sequence of P1, P2, P3, P4, P5, P6, etc.; and P7, P8, P9, P10, P11, P12, respectively.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

As used herein, the singular forms "a", "and," "the" and "is" include plural referents unless the context clearly indicates otherwise. Thus, for example, reference to a "compound" includes a plurality of compounds and reference to "a residue" or an "amino acid" includes reference to one or more residues and amino acids.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes materials and several methods. This example also describes the sequences of analyzed peptides/peptidomimetics.

Chemicals and reagents Bleomycin was purchased from Wako Pure Chemical Co. (Osaka, Japan) and it was dissolved in distilled $H_2O$ to 10 mg/ml. Propidium iodide (PI) and adriamycin were purchased from Sigma (St. Louis, Mo.).

Cell culture A human T-cell leukemia-derived cell line, Jurkat, was cultured in RPMI 1640 (Sigma) supplemented with 10% fetal calf serum (IBL: Immuno-Biological Laboratories, Gunma, Japan) at 37° C./5% $CO_2$. Human pancreatic cancer derived cell line, MIAPaCa2 was cultured in DMEM with 10% fetal calf serum at 37° C./5% $CO_2$.

Cell-cycle analysis The cell cycle status of the cells treated with bleomycin or adriamcin were analyzed by flow cytometry as described by Kawabe (1997) Nature 385: 454–458. In brief, two million cells were re-suspended and incubated in 200 μl Krishan's solution (0.1% Sodium citrate, 50 μg/ml PI, 20 μg/ml RNase A and 0.5% NP-40) for 1 hr at 4° C. and analyzed by a flow cytometry, FACScan™ (Beckton Dickinson, Mountain View, Calif.) with the program CELLQuest™ (Beckton Dickinson).

TABLE 1

Sequences and Corresponding Code Names of exemplary peptides/peptidomimetics.

| | |
|---|---|
| (l-Tyr)(l-Gly)(l-Arg)(l-Lys)(l-Lys)(l-Arg)(l-Arg)(l-Gln)(l-Arg)(l-Arg)(l-Cha)(l-Phe-2,3,4,5,6-F)(l-Arg)(l-Ser)(l-Pro)(l-Ser)(l-Tyr)(l-Tyr) (SEQ ID NO:105) | CBP413 |
| (l-Tyr)(l-Gly)(l-Arg)(l-Lys)(l-Lys)(l-Arg)(l-Arg)(l-Gln)(l-Arg)(l-Arg)(l-Cha)(l-Phe-2,3,4,5,6-F)(l-Arg)(l-Ser)(l-Pro)(l-Ser)(l-Tyr) (SEQ ID NO:106) | CBP420 |

TABLE 1-continued

Sequences and Corresponding Code Names of exemplary peptides/peptidomimetics.

| Sequence | Code |
|---|---|
| (l-Arg)(l-Arg)(l-Arg)(l-Cha)(l-Phe-2,3,4,5,6-F)(l-Arg)(l-Ser)(l-Pro)(l-Ser)(l-Tyr)(l-Tyr)(SEQ ID NO:107) | CBP430 |
| (l-Arg)(l-Arg)(l-Gln)(l-Arg)(l-Arg)(l-Arg)(l-Cha)(l-Phe-2,3,4,5,6-F)(l-Arg)(l-Ser)(l-Pro)(l-Ser)(l-Tyr)(l-Tyr)(SEQ ID NO:108) | CBP431 |
| (l-Arg)(l-Arg)(l-Gln)(l-Arg)(l-Arg)(l-Arg)(l-Cha)(l-Phe-2,3,4,5,6-F)(d-Ser)(d-Trp)(l-Pro)(l-Ser)(l-Tyr)(SEQ ID NO:109) | CBP432 |
| (l-Tyr)(l-Gly)(l-Arg)(l-Lys)(l-Lys)(l-Arg)(l-Arg)(l-Gln)(l-Arg)(l-Arg)(l-Cha)(l-Phe-2,3,4,5,6-F)(1-aminoundecanoic acid)(l-Tyr)(l-Tyr) (SEQ ID NO:110) | CBP440 |
| (d-Tyr)(d-Tyr)(d-Ser)(l-Gly)(d-Ser)(d-Arg)(d-Phe-2,3,4,5,6-F)(d-Cha)(d-Arg)(d-Arg)(d-Arg)(d-Gln)(d-Arg)(d-Arg)(d-Lys)(d-Lys)(d-Arg) (l-Gly)(d-Tyr)(SEQ ID NO:111) | CBP450 |
| (d-Tyr)(d-Ser)(d-Pro)(l-Trp)(l-Ser)(d-Phe-2,3,4,5,6-F)(d-Cha)(d-Arg)(d-Arg)(d-Arg)(d-Gln)(d-Arg)(d-Arg)(SEQ ID NO:87) | CBP451 |
| (d-Tyr)(d-Ser)(l-Pro)(l-Trp)(l-Ser)(d-Phe-2,3,4,5,6-F)(d-Cha)(d-Arg)(d-Arg)(d-Arg)(d-Gln)(d-Arg)(d-Arg)(SEQ ID NO:88) | CBP452 |
| (d-Tyr)(d-Ser)(d-Pro)(l-Trp)(l-Ser)(d-Phe-2,3,4,5,6-F)(d-Pro)(d-Arg)(d-Arg)(d-Arg)(d-Gln)(d-Arg)(d-Arg)(SEQ ID NO:112) | CBP454 |
| (d-Tyr)(d-Ser)(l-Pro)(l-Trp)(l-Ser)(d-Phe-2,3,4,5,6-F)(l-Pro)(d-Arg)(d-Arg)(d-Arg)(d-Gln)(d-Arg)(d-Arg)(SEQ ID NO:113) | CBP455 |
| (l-Tyr)(l-Tyr)(1-aminoundecanoic acid)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(l-Gly) (d-Tyr)(SEQ ID NO:114) | CBP460 |
| (l-Tyr)(1-aminoundecanoic acid)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(l-Gly)(d-Tyr) (SEQ ID NO:115) | CBP461 |
| (l-Tyr)(1-aminoundecanoic acid)(d-Phe-2,3,4,5,6-F)(d-Cha)(SEQ ID NO:116) | CBP462 |
| (1-aminoundecanoic acid)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(1-Gly)(d-Tyr) (SEQ ID NO:117) | CBP463 |
| (1-aminoundecanoic acid)(d-Phe-2,3,4,5,6-F)(d-Cha)(SEQ ID NO:118) | CBP464 |
| (1-aminoundecanoic acid)(d-Phe-2,3,4,5,6-F)(d-Cha)(d-Arg)(d-Arg)(d-Arg)(d-Gln)(d-Arg)(d-Arg)(SEQ ID NO:119) | CBP465 |
| (1-8-aminocaprylic acid)(d-Cha)(d-Phe-2,3,4,5,6-F)(d-Arg)(d-Arg)(d-Arg)(d-Gln)(d-Arg)(d-Arg)(SEQ ID NO:120) | CBP466 |
| (d-Phe-2,3,4,5,6-F)(d-Cha)(SEQ ID NO:121) | CBP470 |
| (d-Cha)(d-Phe-2,3,4,5,6-F)(d-Arg)(d-Arg)(d-Arg)(d-Gln)(d-Arg)(d-Arg)(SEQ ID NO:122) | CBP471 |
| (d-Tyr)(d-Ser)(d-Ser)(d-Trp)(d-Ser)(d-Phe-2,3,4,5,6-F)(d-Cha)(d-Arg)(d-Arg)(d-Arg)(d-Gln)(d-Arg)(d-Arg)(SEQ ID NO:123) | CBP481 |
| (d-Tyr)(d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg)(SEQ ID NO:124) | CBP500 |
| (d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg)(SEQ ID NO:80) | CBP501 |
| (d-Bpa)(1-8-aminocaprylic acid)(d-Cha)(d-Phe-2,3,4,5,6-F)(d-Arg)(d-Arg)(d-Arg)(d-Gln)(d-Arg)(d-Arg)(SEQ ID NO:125) | CBP502 |
| (d-Bpa)(1-8-aminocaprylic acid)(d-Phe-2,3,4,5,6-F)(d-Cha)(d-Arg)(d-Arg)(d-Arg)(d-Gln)(d-Arg)(d-Arg)(SEQ ID NO:126) | CBP503 |
| (d-Asp)(d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg)(SEQ ID NO:127) | CBP504 |
| (d-Bpa)(d-Asp)(d-Ser)(d-Trp)(d-Ser)(d-Phe-2,3,4,5,6-F)(d-Cha)(d-Arg)(d-Arg)(d-Arg)(d-Gln)(d-Arg)(d-Arg)(SEQ ID NO:128) | CBP505 |
| (d-Bpa)(d-Ser)(d-Trp)(d-Ser)(d-Asp)(d-Phe-2,3,4,5,6-F)(d-Cha)(d-Arg)(d-Arg)(d-Arg)(d-Gln)(d-Arg)(d-Arg)(SEQ ID NO:129) | CBP506 |
| (d-Arg)(d-Arg)(d-Arg)(d-Gln)(d-Arg)(d-Arg)(d-Cha)(d-Phe-2,3,4,5,6-F)(d-Ser)(d-Trp)(d-Ser)(d-Bpa)(SEQ ID NO:93) | CBP510 |
| (d-Arg)(d-Arg)(d-Arg)(d-Gln)(d-Arg)(d-Arg)(d-Bpa)(d-Ser)(d-Trp)(d-Ser)(d-Phe-2,3,4,5,6-F)(d-Cha)(SEQ ID NO:94) | CBP511 |
| (d-Arg)(d-Arg)(d-Arg)(d-Arg)(d-Arg)(d-Arg)(d-Cha)(d-Phe-2,3,4,5,6-F)(d-Ser)(d-Trp)(d-Ser)(d-Bpa)(SEQ ID NO:95) | CBP512 |
| (d-Bpa)(d-Ser)(d-Trp)(d-Ser)(d-Bpa)(d-Cha)(d-Arg)(d-Arg)(d-Arg)(d-Gln)(d-Arg)(d-Arg)(SEQ ID NO:130) | CBP601 |
| (d-Bpa)(1-8-aminocaprylic acid)(d-Bpa)(d-Cha)(d-Arg)(d-Arg)(d-Arg)(d-Gln)(d-Arg)(d-Arg)(SEQ ID NO:131) | CBP602 |
| (d-Bpa)(d-Ser)(d-Trp)(d-Ser)(d-Phe4No2)(d-Cha)(d-Arg)(d-Arg)(d-Arg)(d-Gln)(d-Arg)(d-Arg)(SEQ ID NO:89) | CBP603 |
| (d-Bpa)(d-Pro)(d-Trp)(d-Pro)(d-Phe4NO2)(d-Cha)(d-Arg)(d-Arg)(d-Arg)(d-Gln)(d-Arg)(d-Arg)(SEQ ID NO:132) | CBP604 |
| (d-Bpa)(d-Pro)(d-Trp)(d-Pro)(d-Phe4NO2)(d-Nal2)(d-Arg)(d-Arg)(d-Arg)(d-Gln)(d-Arg)(d-Arg)(SEQ ID NO:133) | CBP605 |
| (d-Phe4NO2)(d-Pro)(d-Trp)(d-Pro)(d-Phe4NO2)(d-Cha)(d-Arg)(d-Arg)(d-Arg)(d-Gln)(d-Arg)(d-Arg)(SEQ ID NO:134) | CBP606 |
| (d-Bpa)(d-Ser)(d-Trp)(d-Ser)(d-Phe-2,3,4,5,6-F)(d-Cha)(d-Arg)(d-Arg)(d-Arg)(d-Arg)(d-Arg)(d-Arg)(SEQ ID NO:90) | CBP607 |
| (d-Bpa)(d-Ser)(d-Trp)(d-Ser)(d-Phe-2,3,4,5,6-F)(d-Cha)(d-Arg)(d-Arg)(d-Arg)(d-Arg)(d-Arg)(d-Arg)(SEQ ID NO:91) | CBP608 |
| (d-Bpa)(d-Ser)(d-Trp)(d-Ser)(d-Phe-2,3,4,5,6-F)(d-Cha)(d-Lys)(d-Lys)(d-Lys)(d-Lys)(d-Lys)(d-Lys)(SEQ ID NO:92) | CBP609 |
| (d-Arg)(d-Arg)(d-Bpa)(d-Arg)(d-Arg)(d-Arg)(d-Phe-2,3,4,5,6-F)(d-Cha)(SEQ ID NO:96) | CBP700 |
| (d-Arg)(d-Arg)(d-Arg)(d-Bpa)(d-Arg)(d-Trp)(d-Arg)(d-Phe-2,3,4,5,6-F)(d-Cha)(SEQ ID NO:97) | CBP701 |
| (d-Arg)(d-Arg)(d-Arg)(d-Arg)(d-Bpa)(d-Arg)(d-Trp)(d-Arg)(d-Phe-2,3,4,5,6-F)(d-Cha)(SEQ ID NO:98) | CBP702 |
| (d-Arg)(d-Arg)(d-Arg)(d-Bpa)(d-Arg)(d-Arg)(d-Arg)(d-Phe-2,3,4,5,6-F)(d-Cha)(SEQ ID NO:99) | CBP703 |
| (d-Bpa)(d-Cys)(d-Trp)(d-Arg)(d-Phe-2,3,4,5,6F)(d-Cha)(d-Cys)(SEQ ID NO:135) | CBP524 |
| (d-Tyr)(d-Cys)(d-Pro)(d-Trp)(d-Arg)(d-Phe-2,3,4,5,6F)(d-Cha)(d-Cys)(SEQ ID NO:136) | CBP721 |

Example 2

This example describes data indicating the G2 abrogating activity of various peptides, and the effect of various sequence permutations on activity including the effect of decreasing sequence length.

Flow cytometry analysis of G2 checkpoint abrogation was performed using human leukemia derived Jurkat cell line. In brief, cultured cells were treated with various doses of peptide/peptidomimetic and 40 µg/ml bleomycine for 24 hr. The DNA of the cells was stained with propidium iodide and analyzed by flow cytometry. These results are summarized in Table 2.

A dose response curve of each peptide/peptidomimetic when used against bleomycin treated Jurkat cells are shown in FIGS. 1, 5, 6, 7, 8, 11 and 12; the Y-axis indicates the % G2/M Jurkat cells 24 hrs after the treatment.

Flow cytometry analysis of M phase checkpoint abrogation by the compounds was performed using human T cell leukemia Jurkat cell line treated with colchicine (5 µg/ml or 0.5 µg/ml) and various doses of peptide/peptidomimetics for 24 hr (FIG. 12). The DNA of the cells was stained and analyzed by flow cytometry as described above. These results are also summarized in Table 2.

Figure 1:
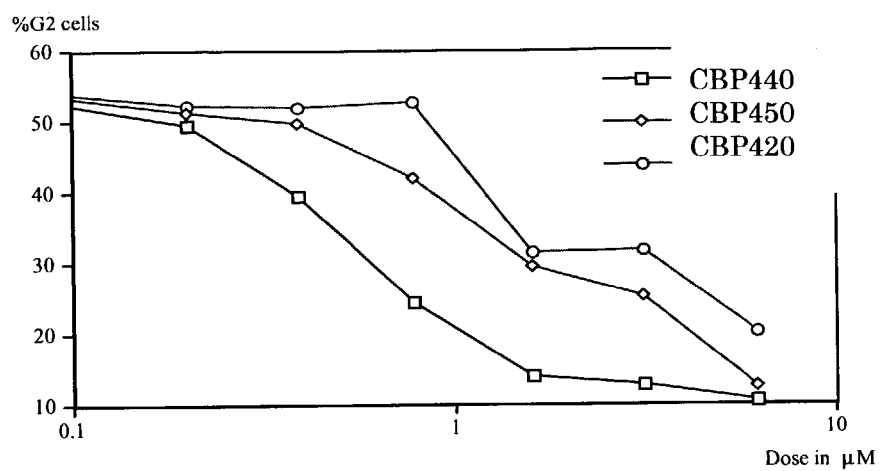
FIG. 1 shows a dose response curve of each compound when used against bleomycin treated Jurkat cells. X-axis indicates the dose and Y-axis indicates the % G2/M cells after treatment.
Figure 2:
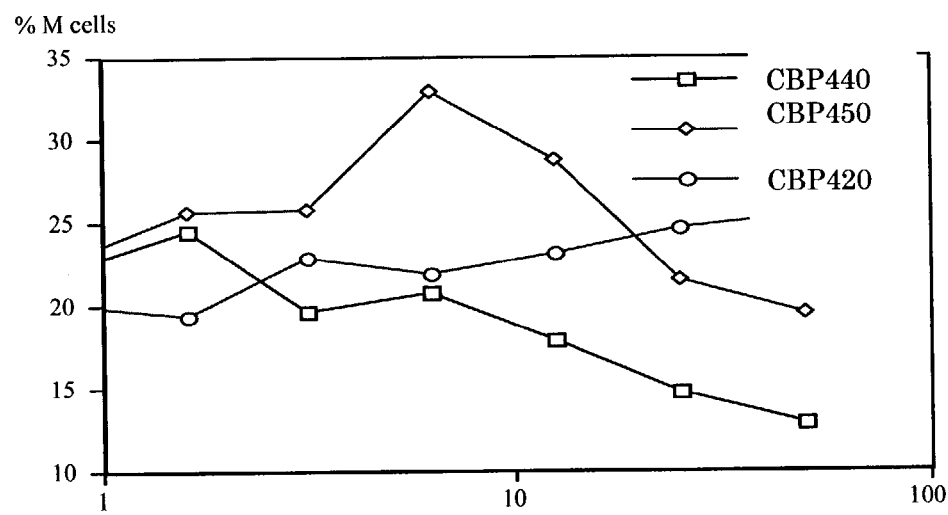
FIG. 2 shows a dose response curve of each compound when used against colchicine treated Jurkat cells. X-axis indicates the dose and Y-axis indicates the % G2/M cells after treatment.

Dose response curves of each peptide/peptidomimetic when used against colchicine treated Jurkat cells are shown in FIGS. 2 and 14; the Y-axis indicates the % G2/M Jurkat cells 24 hrs after the treatment.

TABLE 2

Doses of compounds that induce G2 checkpoint abrogation or side effect

| Code name | Appearance of side effect when used alone (µM) | G2 abrogating dose (µM) | Appearance of side effect when used with Colchicine (µM) |
|---|---|---|---|
| CBP441 | >50 | >50 | >50 |
| CBP462 | >50 | >50 | >50 |
| CBP464 | >50 | >50 | >50 |

TABLE 2-continued

Doses of compounds that induce G2 checkpoint abrogation or side effect

| Code name | Appearance of side effect when used alone ($\mu$M) | G2 abrogating dose ($\mu$M) | Appearance of side effect when used with Colchicine ($\mu$M) |
|---|---|---|---|
| CBP470 | >50 | >50 | >50 |
| CBP430 | >50 | 50 | >50 |
| CBP481 | >50 | >6.25 | >12.5 |
| CBP431 | >50 | ≧3.125 | >50 |
| CBP420 | >50 | ≧1.56 | ≧50 |
| CBP440 | >12.5 | ≧1.56 | >3.125 |
| CBP413 | >25 | ≧1.56 | >25 |
| CBP450 | >6.25 | ≧0.78 | >6.25 |
| CBP460 | >3.125 | ≧0.39 | >3.125 |
| CBP461 | >6.25 | ≧0.39 | >6.25 |
| CBP463 | >6.25 | ≧0.39 | >6.25 |
| CBP500 | >50 | ≧0.39 | >12.5 |
| CBP501 | >50 | ≧0.39 | >25 |

The "Appearance of side effect when used alone" indicates the peptide/peptidomimetic dose that produced Jurkat cell cycle disturbance, i.e., the appearance of significant amounts of SubG1 cells (dead cells) or cells in which the DNA content of each varies more than usual. For example, G1 cells usually exhibit a sharp peak in FACS analysis, but following treatment the peak becomes broader and lower when the cell cycle is disturbed indicating improper cell cycle progression or the beginning of cell death. The "G2 abrogating dose" indicates the peptide/peptidomimetic dose with 40 $\mu$g/ml bleomycine that produced detectable G2 checkpoint abrogation activity following treatment for 24 hours. The "Appearance of side effect when used with colchicine" indicates the peptide/peptidomimetic dose with 5 $\mu$g/ml colchicine that produced Jurkat cell cycle disturbance following treatment for 24 hours.

The G2 checkpoint abrogating activity of CBP501 when combined with cis-platin was studied in various cells lines. Briefly, cis-platin (3 $\mu$g/ml) and CBP501 (0.4, 2 and 10 $\mu$M) were simultaneously added to the cell culture which was incubated 3 hr at 37 degree with 5% $CO_2$. The medium was aspirated, fresh medium without these compounds was added and the cells were incubated for an additional 45 hr. The cells including floating cells were harvested using trypsin-EDTA solution, incubated with Krishan's solution and analyzed for DNA content by flow cytometry as previously described. These results are summarized in Table 3. Shaded highlighting, other than HUVEC, denote cell lines having a significant loss of G2 population and increased subG1 population, indicating G2 checkpoint abrogation and sensitization to cisplatin by CBP501. The observation that HUVEC cells, which are cells having a normal G1 checkpoint, were not sensitized, at least up to 50 $\mu$M CBP501, indicates that CBP501 is specific for the G2 checkpoint rather than non specific.

TABLE 3

G2 checkpoint abrogating doses of CBP501 against various cell lines.

| CBP501 | origin | cis-platin |
|---|---|---|
| HUVEC | umbilical vein endothelium | >50 |
| HT-29 | colon | <2 |
| MIAPaCa2 | pancreas | 0.4<<2 |
| SK-OV-3 | ovary, hMLH1 | 50 |
| HCT116 | colon, hMLH1 | <2 |
| Panc1 | pancreas | >10 |
| MK45 | stomach | >10 |
| SW620 | colon | >10 |
| NCI-H226 | lung, SCC | 0.4 |
| SW900 | lung, SCC | >10 |
| NCI-H520 | lung, SOC | >10 |
| DU-145 | prostate, MLH1 | 0.4 |
| MCF-7 | mammary gland | >10 |

Figure 3:
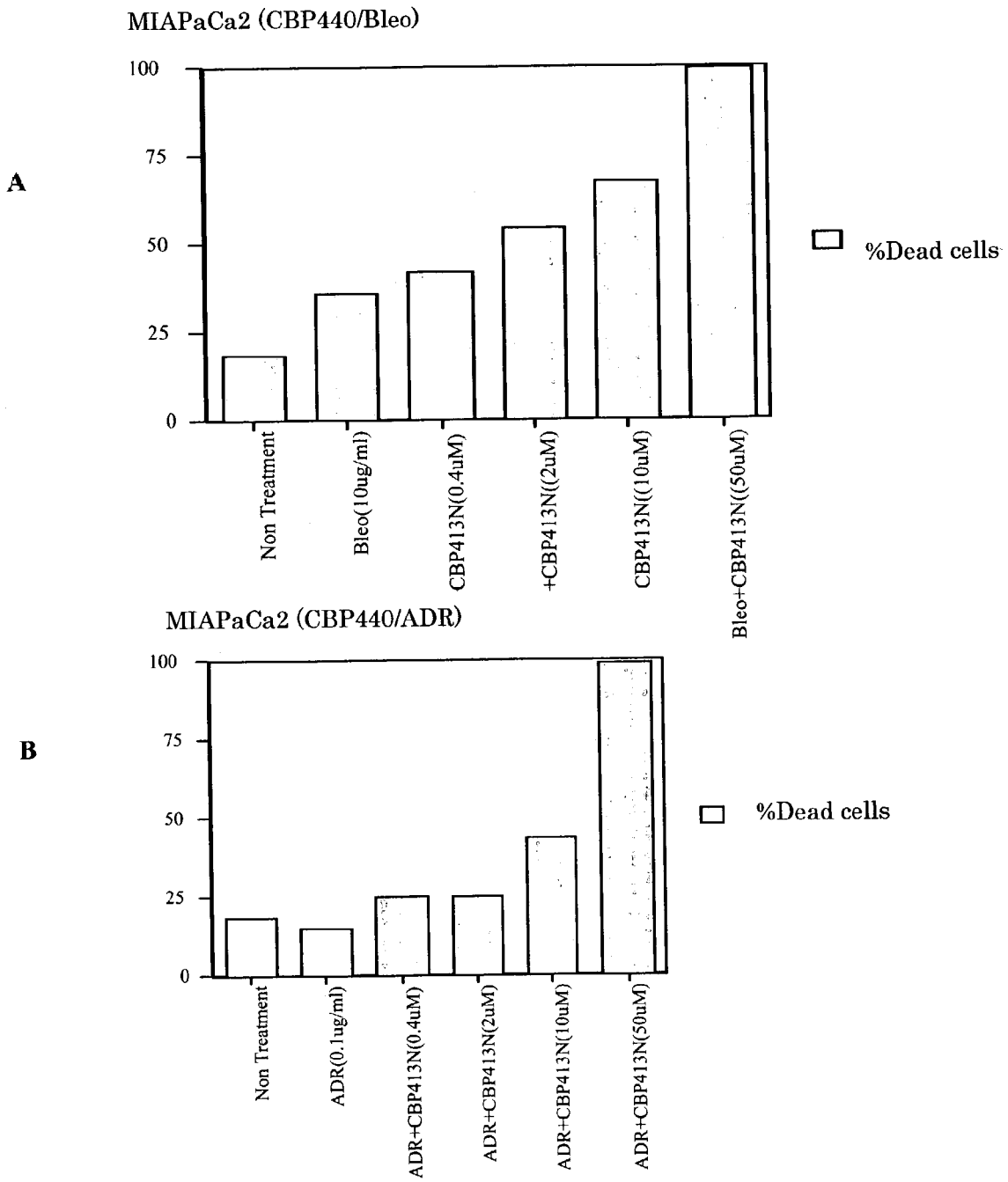
FIGS. 3A and 3B Human pancreatic cancer derived cell line MIAPaCa2 treated with (A) bleomycin (Bleo) or (B) adriamycin (ADR) with various doses of compounds. Harvested cells were stained for their DNA and analyzed with flow cytometry. The % population of sub-G 1 cells are indicated as dead cells.

The G2 checkpoint abrogating activity of various compounds at different doses on human pancreatic cancer derived cell line MIAPaCa2 treated with bleomycine (Bleo) or adriamycin (ADR) was studied. Briefly, cells were incubated with the compounds and bleomycine (10 $\mu$g/ml) or adriamycin (1 $\mu$g/ml) for 3 hours. The medium was changed and incubated for an additional 21 hours. Harvested cells were stained for DNA by propium iodide and analyzed with flow cytometry as previously described. The % of the sub-G1 cell population is indicated as dead cells in FIG. 3. The results indicate that CBP501 sensitized MIAPaCa2 cells to both bleomycin and adriamycin in a dose dependent manner.

Figure 4A:
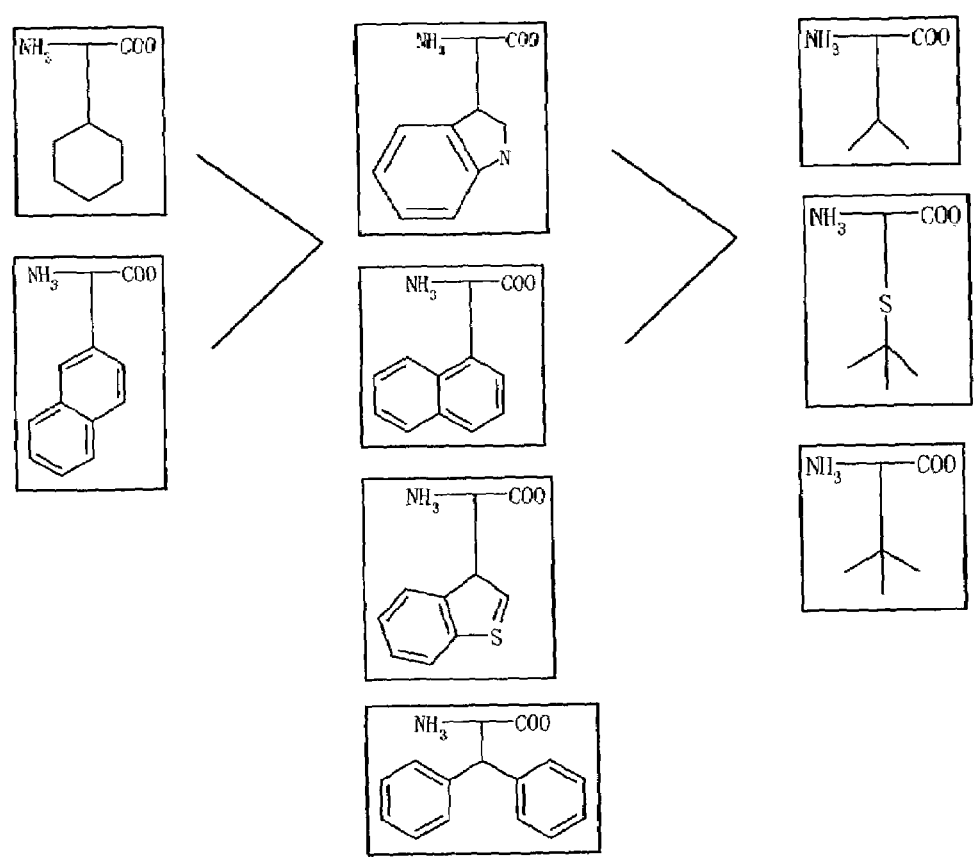
FIGS. 4A to 4C are a schematic diagram of the structure activity relationship of G2 checkpoint abrogator (l-Gly)(l-Arg)(l-Lys)(l-Lys)(l-Arg)(l-Arg)(l-Gln) (l-Arg) (l-Arg)(l-Cha)(l-Phe-2,3,4,5,6-F)(l-Arg)(l-Ser)(l-Pro)(l-Ser)(l-Tyr)(l-Tyr) (SEQ ID NO:78): (A) G2 checkpoint abrogation activity of amino acid substitutions for l-Cha in bleomycin treated Jurkat cells are indicted in order, [l-Cha=l-Nal(2)]>[l-Ala(3-Bzt)=l-Nal(1)=l-Trp=l-Dph]>[l-Ala(tBu)=Cys (tBu)=Leu]; (B) M phase checkpoint abrogating activity and/or non specific toxicity of amino acid substitutions for l-Cha in cholchicine treated Jurkat cells in order, [Ala(3-Bzt)=l-Nal(1)=l-Dph]>[l-Cha=l-Nal(2)]; (C) G2 checkpoint abrogating activity of amino acid substitution for l-Phe-2,3,4,5,6-F are indicted in order, l-(Phe-2,3,4,5,6-F)=l-(Phe-3,4,5-F)=l-(Phe-4CF3)]>[l-(Phe-3Br,4Cl,5Br)=l-(Phe-4Cl)=l-Tyr].
Figure 4B:
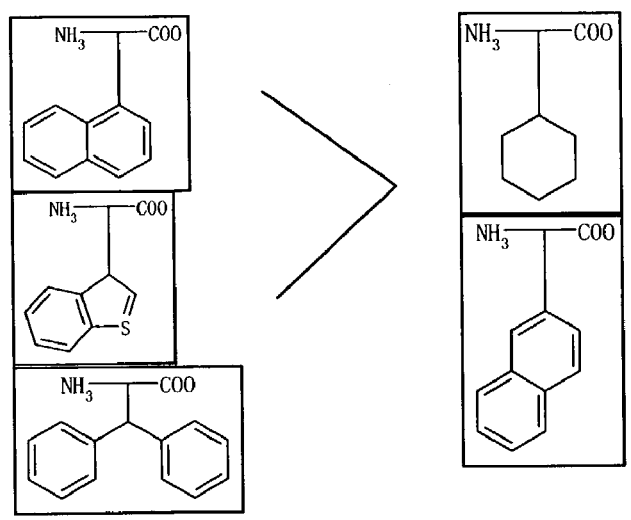
Figure 4C:
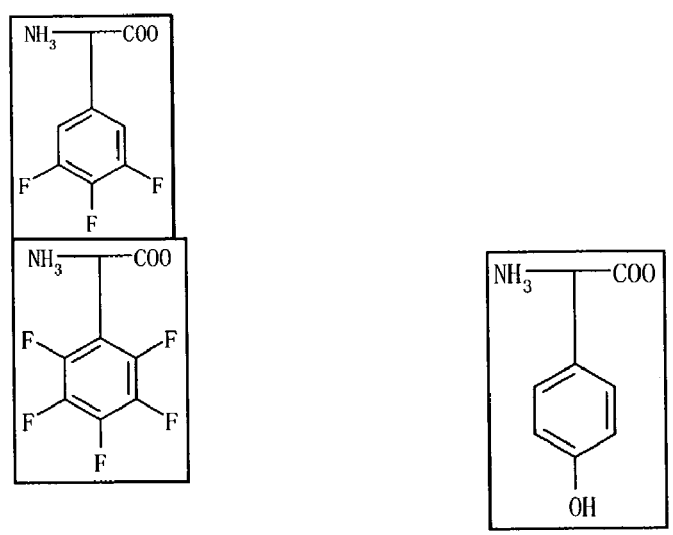
Figure 5:
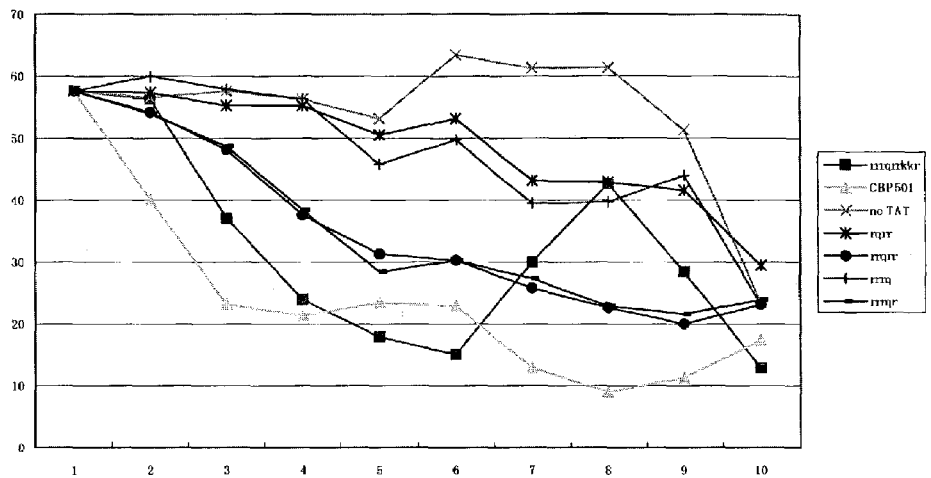
FIG. 5 shows G2 abrogating activity of various arginine rich sequences. Indicated peptides were added to Jurkat cells with or without bleomycin. The % G2/M cells is indicated on the Y-axis. X-axis is as follows: 1, Bleomycin alone; 2, 0.2 µg/ml peptide; 3, 0.39 µg/ml peptide; 4, 0.78 µg/ml peptide; 5, 1.56 µg/ml peptide; 6, 3.125 µg/ml peptide; 7, 6.25 µg/ml peptide; 8, 12.5 µg/ml peptide; 9, 25 µg/ml peptide; and 10, 50 µg/ml peptide. Peptide sequences are as follows: rrrqrrkkr, (d-Bpa)(d-Ser)(d-Trp)(d-Ser)(d-Phe-2,3,4,5,6-F)(d-Cha)(d-Arg)(d-Arg) (d-Arg)(d-Gln) (d-Arg) (d-Arg)(d-Lys)(d-Lys)(d-Arg) (SEQ ID NO:79); CBP501, (d-Bpa) (d-Ser)(d-Trp)(d-Ser) (d-Phe-2,3,4,5,6-F)(d-Cha) (d-Arg)(d-Arg)(d-Arg)(d-Gln) (d-Arg) (d-Arg)(SEQ ID NO:80); no TAT, (d-Bpa) (d-Ser)(d-Trp)(d-Ser)(d-Phe-2,3,4,5,6-F) (d-Cha) (SEQ ID NO:81); rqrr, (d-Bpa)(d-Ser)(d-Trp)(d-Ser) (d-Phe-2,3,4,5,6-F)(d-Cha) (d-Arg)(d-Gln)(d-Arg) (d-Arg)(SEQ ID NO:82); rrqrr, (d-Bpa)(d-Ser) (d-Trp) (d-Ser) (d-Phe-2,3,4,5,6-F)(d-Cha)(d-Arg)(d-Arg)(d-Gln) (d-Arg)(d-Arg)(SEQ ID NO:83); rrrq, (d-Bpa) (d-Ser)(d-Trp)(d-Ser) (d-Phe-2,3,4,5,6-F)(d-Cha) (d-Arg)(d-Arg)(d-Arg)(d-Gln)(SEQ ID NO:84); and rrrqr, (d-Bpa)(d-Ser)(d-Trp)(d-Ser) (d-Phe-2,3,4,5,6-F)(d-Cha)(d-Arg)(d-Arg)(d-Arg)(d-Gln) (d-Arg)(SEQ ID NO:85).
Figure 6:
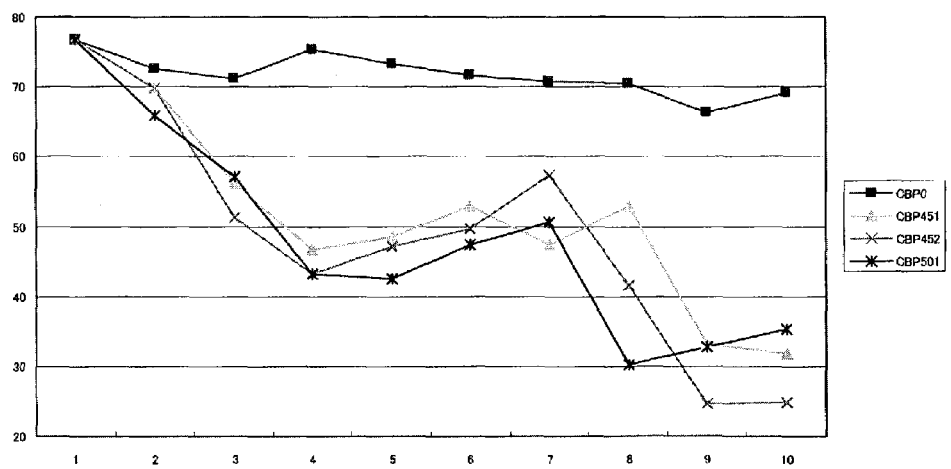
FIG. 6 shows G2 abrogating activity of various peptides without (d-Bpa). Indicated peptides were added to Jurkat cells with or without bleomycin. The % G2/M cells is indicated on the Y-axis. X-axis is as follows: 1, Bleomycin alone; 2, 0.2 µg/ml peptide; 3, 0.39 µg/ml peptide; 4, 0.78 µg/ml peptide; 5, 1.56 µg/ml peptide; 6, 3.125 µg/ml peptide; 7, 6.25 µg/ml peptide; 8, 12.5 µg/ml peptide; 9, 2.5 µg/ml peptide; and 10, 50 µg/ml peptide. Peptide sequences are as follows: CBP0, (d-Arg)(d-Arg) (d-Arg)(d-Gln)(d-Arg) (d-Arg)(SEQ ID NO:86); CBP451, (d-Tyr)(d-Ser)(d-Pro) (1-Trp)(1-Ser)(d-Phe-2,3,4,5,6-F)(d-Cha) (d-Arg)(d-Arg)(d-Arg)(d-Gln) (d-Arg) (d-Arg)(SEQ ID NO:87); CBP452, (d-Tyr)(d-Ser)(1-Pro)(1-Trp)(1-Ser)(d-Phe-2,3,4,5,6-F) (d-Cha)(d-Arg)(d-Arg) (d-Arg)(d-Gln) (d-Arg) (d-Arg) (SEQ ID NO:88); and CBP501, (d-Bpa)(d-Ser)(d-Trp)(d-Ser) (d-Phe-2,3,4,5,6-F)(d-Cha)(d-Arg)(d-Arg)(d-Arg)(d-Gln) (d-Arg)(d-Arg) (SEQ ID NO:80).
Figure 7:
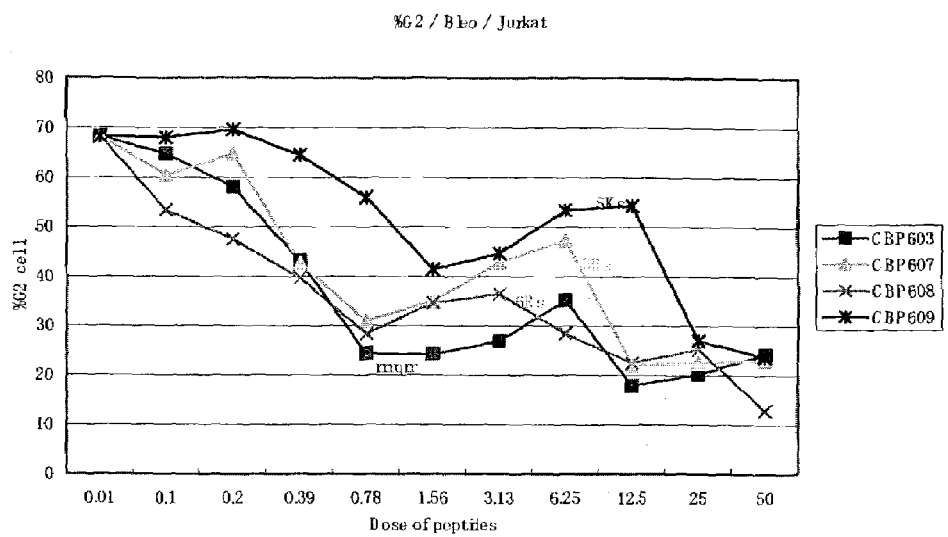
FIG. 7 shows G2 abrogating activity of various arginine rich and lysine rich peptide sequences. Indicated peptides were added to Jurkat cells as above and the % G2/M cells calculated (Y-axis). Peptide sequences are as follows: CBP603, (d-Bpa)(d-Ser) (d-Trp) (d-Ser)(d-Phe4NO2)(d-Cha)(d-Arg)(d-Arg)(d-Arg)(d-Gln) (d-Arg) (d-Arg)(SEQ ID NO:89); CBP607, (d-Bpa) (d-Ser)(d-Trp)(d-Ser) (d-Phe-2,3,4,5,6-F)(d-Cha) (d-Arg) (d-Arg) (d-Arg) (d-Arg) (d-Arg) (SEQ ID NO:90); CBP608, (d-Bpa)(d-Ser)(d-Trp)(d-Ser) (d-Phe-2,3,4,5,6-F)(d-Cha) (d-Arg) (d-Arg) (d-Arg) (d-Arg) (d-Arg) (d-Arg)(SEQ ID NO91:); and CBP609, (d-Bpa)(d-Ser)(d-Trp) (d-Ser) (d-Phe-2,3,4,5,6-F) (d-Cha) (d-Lys) (d-Lys) (d-Lys) (d-Lys) (d-Lys) (d-Lys) (SEQ ID NO:92).
Figure 8:
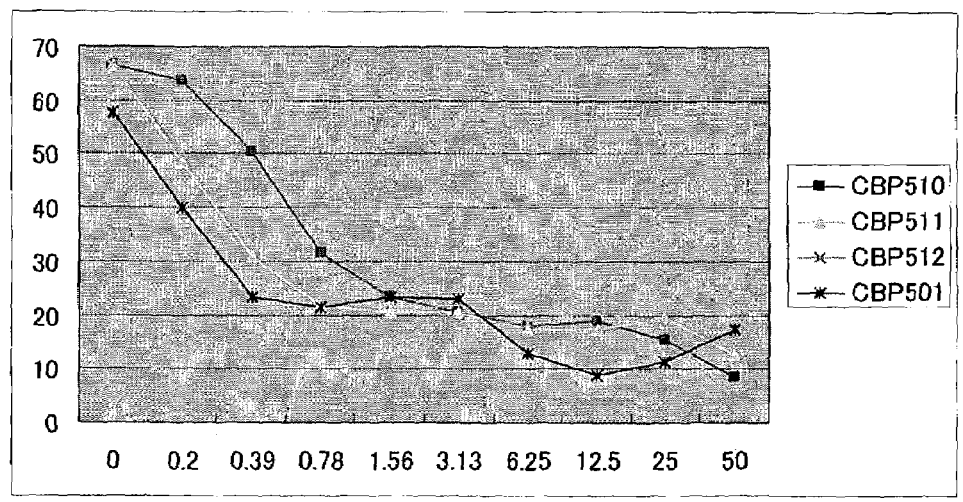
FIG. 8 shows that the location of the arginine rich portion of the sequence can be varied. Indicated peptides were added to Jurkat cells as above and the % G2/M cells calculated (Y-axis). Peptide sequences are as follows: CBP501, (d-Bpa) (d-Ser)(d-Trp)(d-Ser) (d-Phe-2,3,4,5,6-F) (d-Cha)(d-Arg)(d-Arg)(d-Arg)(d-Gln) (d-Arg) (d-Arg) (SEQ ID NO:80); CBP510, (d-Arg)(d-Arg) (d-Gln) (d-Arg) (d-Arg)(d-Arg) (d-Cha)(d-Phe-2,3,4,5,6-F) (d-Ser)(d-Trp) (d-Ser) (d-Bpa) (SEQ ID NO:93); CBP511, (d-Arg)(d-Arg) (d-Gln) (d-Arg) (d-Arg)(d-Arg) (d-Bpa)(d-Ser) (d-Trp)(d-Ser) (d-Phe-2,3,4,5,6-F)(d-Cha) (SEQ ID NO:94); and CBP512, (d-Arg) (d-Arg) (d-Arg) (d-Arg) (d-Arg) (d-Arg) (d-Cha)(d-Phe-2,3,4,5,6-F)(d-Ser)(d-Trp)(d-Ser) (d-Bpa) (SEQ ID NO:95).

FIGS. 4A and 4C are a summary of the G2 checkpoint abrogating activity performed with pairs of peptides in which one amino acid residue is different from the other. The G2 checkpoint abrogating activity of these peptides was analyzed using bleomycin treated Jurkat cells as described above. FIG. 4B is a summary of M checkpoint abrogating activity and/or non specific toxicity analysis performed with pairs of peptides in which one amino acid residue is different from the other. The M checkpoint abrogating activity and/or non specific toxicity of these peptides was analyzed using colchicine treated Jurkat cells as described above.

The G2 checkpoint abrogating activity of various arginine rich sequences at different doses on cells treated with bleomycine was studied. Briefly, peptides were added to culture medium of Jurkat cells with bleomycin (40 $\mu$g/ml) at 0.2 $\mu$g/ml, 0.39 $\mu$g/ml, 0.78 $\mu$g/ml, 1.56 $\mu$g/ml, 3.125 $\mu$g/ml, 6.25 $\mu$g/ml, 12.5 $\mu$g/ml, 25 $\mu$g/ml and 50 $\mu$g/ml. Cells were subsequently harvested after 24 hours, stained with Krishan's solution, and analyzed with flow cytometry as previously described. The % G2/M cells (Y-axis) was plotted against the peptide doses (X-axis) in FIG. 5. The data indicate that the "(d-Arg) (d-Arg) (d-Arg)(d-Gln) (d-Arg) (d-Arg) (SEQ ID NO:137)" basic residue rich sequence is the best sequence compared to sequences having fewer or greater numbers of residues.

The G2 checkpoint abrogating activity of peptides without (D-Bpa) at different doses on cells treated with bleomycine was studied. Briefly, peptides were added to culture medium of Jurkat cells with bleomycin (40 $\mu$g/ml) at 0.2 $\mu$g/ml, 0.39 $\mu$g/ml, 0.78 $\mu$g/ml, 1.56 $\mu$g/ml, 3.125 $\mu$g/ml, 6.25 $\mu$g/ml, 12.5 $\mu$g/ml, 25 $\mu$g/ml and 50 $\mu$g/ml. Cells were subsequently harvested and analyzed with flow cytometry as previously described. The % G2/M cells (Y-axis) was plotted against the peptide doses (X-axis) in FIG. 6. This result indicates that the sequence (Tyr)(Ser)(Pro)(Trp)(Ser) (Phe-2,3,4,5,6F)(Cha) (SEQ ID NO:138) has comparable G2 checkpoint abrogating activity to the sequence (Bpa)(Ser)(Trp)(Ser)(Phe-2,3,4,5,6F)(Cha) (SEQ ID NO: 139).

The G2 checkpoint abrogating activity of arginine rich and lysine rich sequences at different doses on cells treated with bleomycine was studied. Briefly, peptides were added to culture medium of Jurkat cells with bleomycin (40 μg/ml) at the indicated dose (X-axis). Cells were subsequently harvested and analyzed with flow cytometry as previously described. The % G2/M cells (Y-axis) was plotted against the peptide doses in FIG. 7. The results indicate that Arg sequences appear to provide better activity than Lys sequences for the basic amino acid rich sequence and that Gln is not essential for function of the sequence.

The G2 checkpoint abrogating activity of sequences in which the location of the arginine rich region is varied was studied. Briefly, peptides were added to culture medium of Jurkat cells with bleomycin (401 μg/ml) at the indicated dose (X-axis) for 24 hours. Cells were subsequently harvested and analyzed with flow cytometry as previously described. The % G2/M cells (Y-axis) was plotted against the peptide doses in FIG. 8.

The data indicate that the G2 abrogating activity of the peptides is not significantly altered by changing the location of the arginine rich region. In addition, CBP501 was soluble in water, whereas CBP511 was not. This difference can be advantageous for particular drug delivery systems, since some systems prefer water insoluble compounds.

Figure 9:
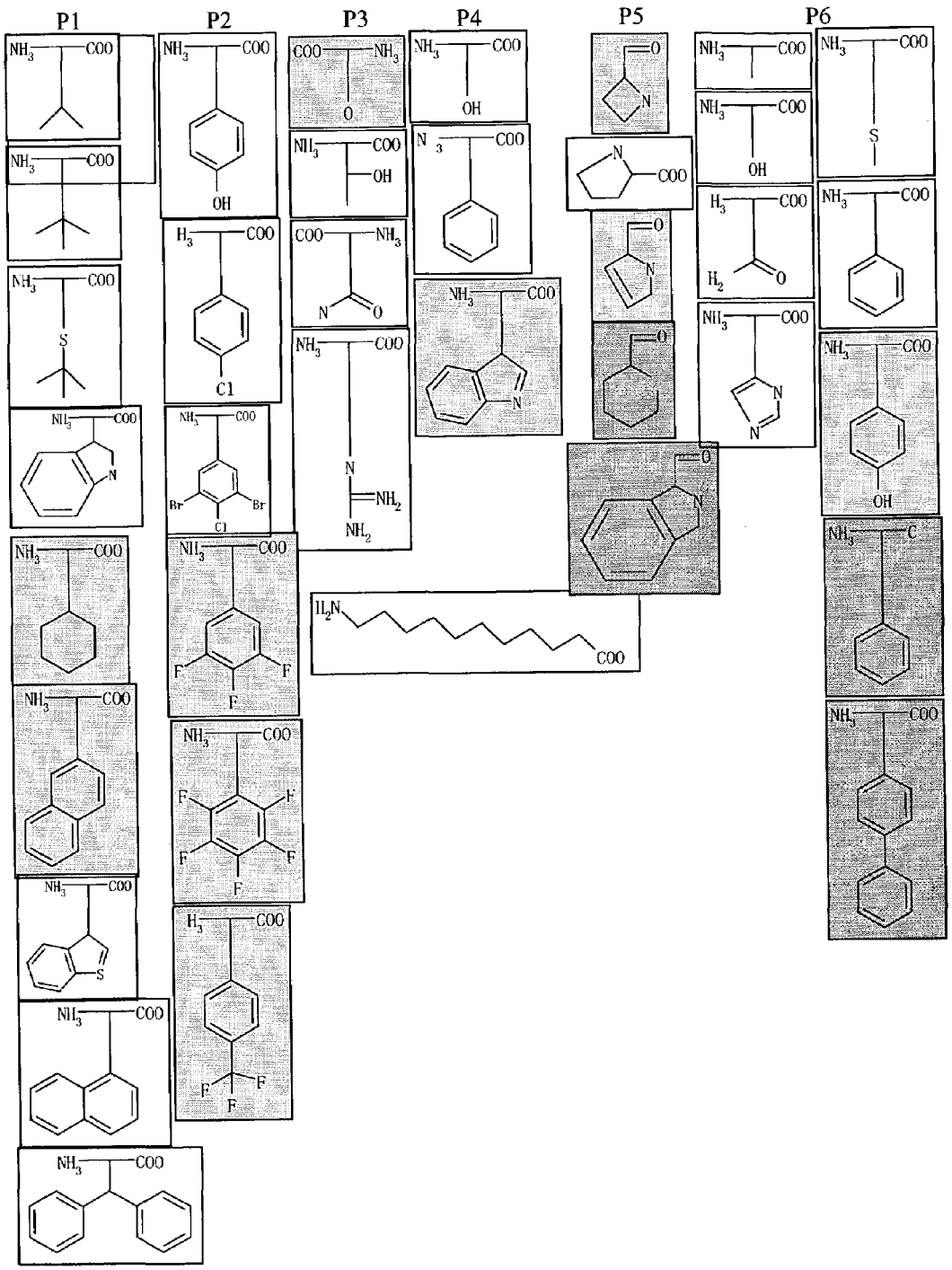
FIG. 9 shows the structure of several studied substituted peptide sequences. G2 abrogating activity increased with the light shaded substitutions (*), M phase checkpoint abrogating activity and/or non specific toxicity increased with the darker shaded substitutions (**) and remained about the same for the rest of the substitutions.

FIG. 9 illustrates a summary of the analysis performed with various peptide pairs in which only one amino acid residue was different between the pairs. The G2 checkpoint abrogating activity of these peptides was analyzed using bleomycin treated Jurkat cells as described.

The size, charge and hydrophobicity of each amino acid determine how effectively the sequence fits into a target molecule. The side chain of the peptide or peptidomimetic would move freely, so even with one or two unfavorable side chains the peptide or peptidomimetic could fit a pocket or groove of the target molecule. The summary indicates that there are preferable sizes for each side chain which suggest the size of the binding region (pocket or groove) of the target protein for each side chain. For example, side chains with a ring structure such as benzene, indole and cyclohexane, determine the strength of G2 abrogation or M abrogation and/or non specific toxicity; see FIGS. 9 and 4, where ring structures larger than 5 membered affect the G2 abrogating activity (moderate size at P1 and P2 increase G2 abrogating activity, whereas, too large of a structure (P1, P5 and P6) increase M abrogation and/or non specific toxicity.

Side chains without a ring structure appear neutral. So, to attain better activity a proper sized ring structure at P1, P2, P4 and P6, and either no ring structure at P3 and P5 or a ring structure less than 6 members is desired. A proper ring for P1, P2, and P6 is from a one to a 6 membered ring through fusion of two rings with either 5 or 6 membered. For P4, a proper size ring is a fusion of two rings, each of which are 5 or 6 membered. Thus, for P1, Cha or Nal(2) appear to be the best fits; for P2, Phe-2,3,4,5,6F, Phe-3,4,5F or Phe-CF3 appear best. These side chain sizes indicate that there are either two pockets or a single larger pocket in the target molecule where this region interacts. For P3 and P5, a small side chain such as Ser or Pro is acceptable and a larger side chain such as Arg is also acceptable, indicating that there is no pocket in this region of target molecule, so side chains can just lay opposite to target. However, it is possbile that a ring structure might enable the peptide or peptidomimetic to interact with another molecule (i.e., other than a target molecule) which may in turn increase side effect. For P6, Bpa or Ser-Tyr appear better than Tyr alone or a smaller side chain, indciating a deeper groove that lay horizontally in the target. There also may be a shallow and wider pocket for P4 in the target based on the sizes of the residues for P4.

Figure 11:
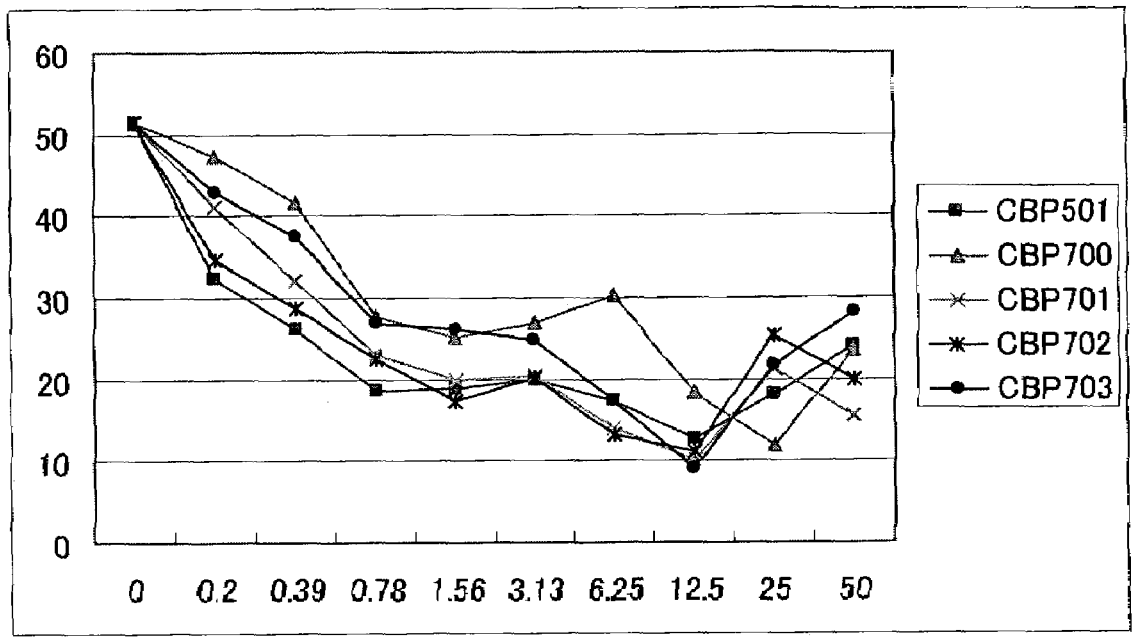
FIG. 11 shows G2 abrogating activity of peptides having a kinase inhibitng sequence region and a sequence region based upon an HIV-TAT transduction sequence, as above. The % G2/M cells is indicated on the Y-axis. X-axis is as follows: 1, Bleomycin alone; 2, 0.2 µg/ml peptide; 3, 0.39

The following peptides were analyzed using Jurkat and bleomycin as described. Sequences of peptides are as follows: CBP501, (d-Bpa) (d-Ser)(d-Trp)(d-Ser) (d-Phe-2,3,4, 5,6-F)(d-Cha) (d-Arg) (d-Arg) (d-Arg) (d-Gin) (d-Arg) (d-Arg) (SEQ ID NO:80); CBP700, (d-Arg) (d-Arg) (d-Bpa) (d-Arg) (d-Arg) (d-Arg) (d-Phe-2,3,4,5,6-F) (d-Cha) (SEQ ID NO:96); CBP701, (d-Arg) (d-Arg) (d-Arg) (d-Bpa)(d-Arg)(d-Trp) (d-Arg) (d-Phe-2,3,4,5,6-F)(d-Cha) (SEQ ID NO:97); CBP702, (d-Arg) (d-Arg) (d-Arg) (d-Arg) (d-Bpa) (d-Arg)(d-Trp)(d-Arg)(d-Phe-2,3,4,5,6-F)(d-Cha) (SEQ ID NO:98); and CBP703, (d-Arg) (d-Arg) (d-Arg)(d-Bpa)(d-Arg) (d-Arg) (d-Arg)(d-Phe-2,3,4,5,6-F) (d-Cha) (SEQ ID NO:99). The results indicate that CBP700, 701, 702, 703, although shorter than other exemplified peptides, retain G2 checkpoint abrogating activity comparable to other peptides having significant G2 checkpoint abrogating activity (FIG. 11).

A comparison between G2 checkpoint abrogating activity and non specific toxicity (M checkpoint abrogation) by CB501 was performed. In brief, Jurkat cells were treated with 40 μg/ml bleomycin or 0.5 μg/ml colchicine for G2 checkpoint abrogating activity and non specific toxicity, respectively. The DNA amount in each of the treated cells was analyzed by flow cytometry, as previously described. The data indicate that G2 checkpoint was abrogated in a dose dependent manner for CBP501 while non specific toxicity was absent up to 50 μM of peptide, as determined by the unchanged percentage of M phase arrested cells (FIG. 12).

Example 3

This example describes peptide/peptidomimetic kinase inhibition activity and serum stability analysis of various peptides.

Since two kinases, Chk1 and Chk2, are important for G2 checkpoint mechanism, kinase inhibition analysis of both enzymes was performed. In vitro kinase inhibition analysis was performed using "PepTag® Non-Radioactive Protein Kinase Assays", Promega, according to company's protocol, except purified CHK2 kinase was used instead of PKC. Purified PKC was purchased from Upstate Biotechnology, Inc. These results are shown in Table 4A.

TABLE 4A

| Kinase inhibition analysis of the compounds | | |
|---|---|---|
| $IC_{50}$ in μM | PKA | CHK2 |
| CBP450 | >400 | 10 |
| CBP440 | 180 | 8 |

In vitro kinase inhibition analysis was performed by CycLex, Co. Ltd., Nagano, Japan. Briefly, baculovirus derived recombinant human full length Chk1 with histidine tag or *E. Coli* derived recombinant human full length Chk2 fused with GST were used as kinases. *E. Coli* derived recombinant GST-Cdc25C (amino acis 167–267) was used as a substrate. Reaction conditions were 20 mM Hepes-KOH (pH7.5), 1 mM DTT, 801 g/ml BSA, 10 mM MgCl2 and 50 mM ATP at 30 degree for 60 min. The phosphorylation of serine 216 on GST-Cdc25C was detected by anti-Cdc25C-phosphorylated S216 antibody with enzyme linked immune assay. These results are shown in Table 4B.

TABLE 4B

Kinase inhibition analysis of peptides.

|  | CHK1 | CHK2 |
|---|---|---|
| CBP500 | 5.6 | 8 |
| CBP501 | 7.9 | 18.6 |
| CBP505 | 63.4 | >100 |
| CBP506 | 37.6 | 67 |
| CBP603 | 15.5 | 18.1 |

The data indicate that both Chk1 and Chk2 kinase inhibition occur at a dose higher than the G2 abrogating dose ($IC_{50}$ for G2 abrogation by CBP500, 501, 505, 506, 603 are all less than 1 $\mu$M). These results suggest that these peptides have a mechanism of action in addition to inhibiting Chk1/2 molecules. Alternatively, the peptides possibly accumulate within cells such that their concentration is greater within cells than in the surrounding medium.

Serum analysis was performed to determine the stability of peptides in mouse and human serum. Briefly, peptides (10 mM or 2.5 mM) were incubated with freshly prepared human serum at 37 degrees for 1 hr. CBP50 (10 mM) was incubated with freshly prepared mouse serum for 1 hr at 37 degree. Jurkat cells were treated with the serum with or without peptides and bleomycin (40 $\mu$g/ml) and incubated for 24 hr. The population of G2 phase cells was determined by flow cytometry as previously described. The residual G2 checkpoint abrogating activity of serum treated peptides were determined by comparing the % G2 cells of the treated serum and the standard curve produced with medium treated peptides, bleomycin and Jurkat cells (Table 5A). The residual CBP501 quantity was determined with HPLC after deproteinating with ethanol treatment (Table 5B). The data indicate that peptide with d-type amino acids such as CBP501 and CBP603 are more stable in serum than peptide with l-type amino acid such as CBP413.

TABLE 5A

Human serum treatment analysis

Residual activity of peptide after 1 hr human serum treatment

| | |
|---|---|
| CBP413 | <0.4% of original |
| CBP501 | >50% of original |
| CBP603 | >50% of original |

TABLE 5B

Mouse serum treatment analysis

Residual peptide after 1 hr human serum treatment

| | |
|---|---|
| CBP501 | >90% |

Example 4

This example describes the anti-cell proliferative activity of CBP501 on cultured cells. This example also describes data demonstrating in vivo activity of the peptides/peptidomimetics.

To demonstrate anti-cell proliferative activity of the compounds, cultured MIAPaCa2 human pancreatic carcinoma cells were treated with CBP501 (10 $\mu$mM), cisplatin (1, 3 or 9 $\mu$g/ml) and oxaliplatin (1, 3 or 9 $\mu$g/ml) alone, and in combination. Briefly, cells were plated at 300 cells/well in 6 well plates, incubated overnight, and treated with the compounds for three hours. The medium was changed and cultured for an additional 10 days. Cells were subsequently fixed with 70% methanol, stained with 0.1% crystal violet and visualized. The colony formation analysis results indicated that CBP501 enhanced the cyto-toxic activity of both cisplatin and oxaliplatin against MIAPaCa2 cells.

Similar studies were performed using normal human umbilical endothelial cells (HUVEC). Since normal cells do not form colonies, they were plated 3000 cell/well instead of 300 cell/well. The results indciate that peptide by itself does not disturb the growth of normal cells nor did the peptide augument cytotoxic activity of cisplatin and oxaliplatin towards the cell. The peptides therefore do not appear to exhibit significant G2 abrogating activity against normal cells subjected to nucleic acid damaging treatment, incontrast to hyperoliferating cells such as cancer cells, which are sensitized to nucleic acid damaging treatment. The results indicate the specificity of the peptide in sensitizing proliferating cells but not normal cells against nucleic acid damaging treatment.

TABLE 6

Growth inhibition analysis of MIAPaCa2 using alamar blue.

| | IC50 | | |
|---|---|---|---|
| | 24 hr | 48 hr | 72 hr |
| cisplatin | 16 $\mu$M | 31 $\mu$M | 46 $\mu$M |
| CBP501 | 6 $\mu$M | 10 $\mu$M | 13 $\mu$M |
| CBP501 with 10 uM cisplatin | 0.6 $\mu$M | 1 $\mu$M | 6 $\mu$M |

AlamarBlue analysis was performed to analyze the growth inhibiting activity of CBP501 with and without cisplatin. Briefly, MIAPaCa2 cells were exposed to 1, 3, 10, 30, 100 $\mu$M of cisplatin or 0.22, 0.67, 2, 6, and 18 $\mu$M of CBP501 with or without 10 $\mu$M cisplatin for three hours in 96 well plates at 2500cell/well in duplicate manner. The medium was changed and incubated an additional 24, 48 or 72 hour. Following incubation, 20 $\mu$l of alamarBlue 90% reagent was added to each well for another 6 hours for detection of cell viability by fluorescent intensity. Fluorescent intensity was measured using a Spectrafluor Plus plate reader with exitation 530 nm and emission 590 nm. The $IC_{50}$ was calculated (Table 6).

This study indicates that CBP501 alone inhibits cell growth better than cisplatin in molar dose. CBP501 suppressed cell growth at a much lower dose when combined with 10 $\mu$M of cisplatin, which is approximately the dose of cisplatin used for cancer treatment. Furthermore, growth suppressing activity of CBP501 was longer than cisplatin; the $IC_{50}$ at 72 hour was much better when CBP501 was used than cisplatin.

The in vivo half life of CBP501 was determined by quantifying CBP501 in mouse serum 1, 3 and 6 hr following intra-peritoneal injection of CBP501 (40 mg/kg). The residual intact CBP501 quantity was determined with HPLC after deproteinating mouse serum drawn from injected mice with ethanol treatment (Table 7).

TABLE 7 in vivo half life of CBP501

Half-life after 40 mg/kg intra-peritoneal injection

| | |
|---|---|
| CBP501 | 3 hr |

To determine tolerance to peptides, groups of ten mice were intravenously injected once with CBP501 (5, 8 or 10 mg/kg) or intra-peritonealy injected once with CBP501 (50, 80 or 100 mg/kg). Injected mice were observed for a week for their survival (Table 8).

TABLE 8

Maximal tolerated dose in mouse by single injection

|  | MTD (iv) | MTD (ip) |
|---|---|---|
| CBP413 | 14 mg/kg | 146.7 mg/kg |
| CBP501 | 10 mg/kg | 98.8 mg/kg |

Figure 10:
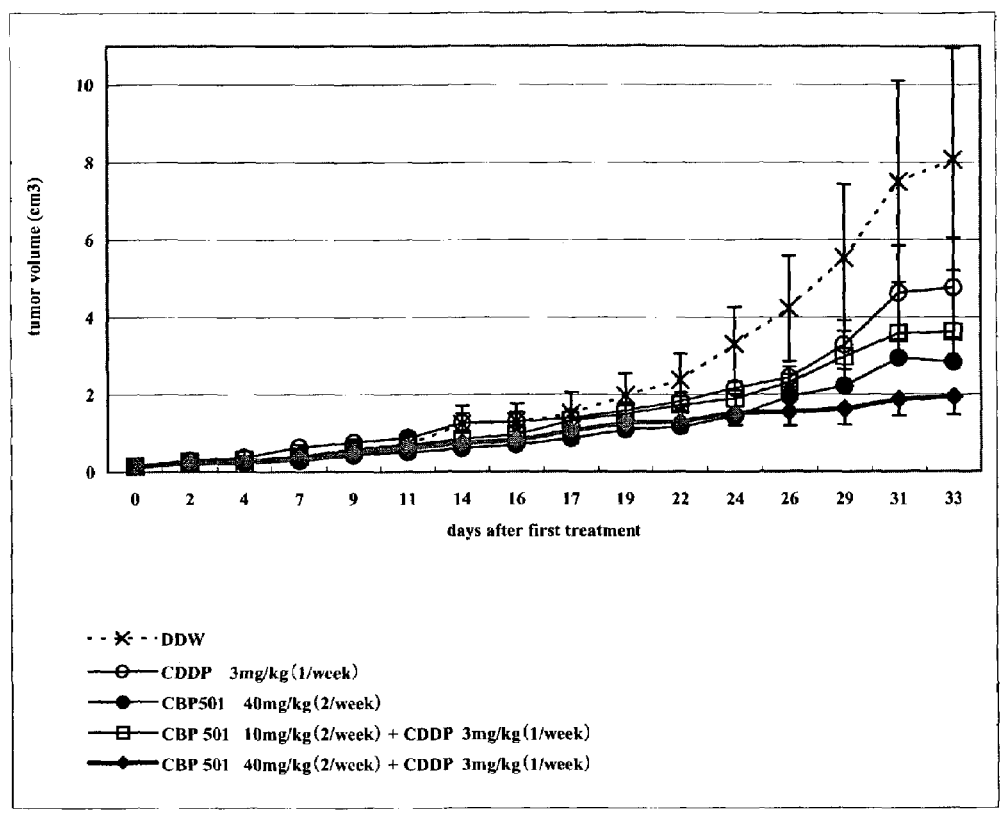
FIG. 10 shows inhibition of tumor growth (human pancreatic carcinoma) in scid mice following treatment with CBP501 and cisplatin. Day0 indicates treatment initiation. Mean tumor sizes with standard deviation for each treatment group are indicated on the Y-axis and the number of days following treatment initiation are indicated on the X-axis. DDW, double-distilled water.

To study in vivo efficacy of the compounds, MIAPaCa2 human pancreatic carcinoma cells were implanted subcutaneously in scid mice. The treatment was initiated when the size of the primary tumor became 0.1 cm3 (Day0) or larger, e.g., 7 or 8 mm in diameter. CDDP (3 mg/kg) and CBP 501 (10 or 40 mg/kg) were intra-peritoneally administered alone or in combination. Tumor sizes were measured using calipers three times a week, and volumes were calculated using the formula: weight(mg)=[width (mm)2×length (mm)]/2. Mean tumor sizes for each treatment group are plotted (n=4) against the days after the start of treatment (FIG. 10).

The results indciate that CBP501 treatment alone suppresses the growth of human pancreatic cancer cell in vivo. The results further indicate that CBP501 increased the anti-tumor activity of cisplatin.

What is claimed is:

1. A contiguous peptide or peptidomimetic sequence comprising the following structure: (d-Bpa)(d-(Ser)(d-Trp)(d-Phe-2,3,4,5,6-F)(d-Cha)(d-Arg)(d-Arg)(d-Arg)(d-Gln)(d-Arg)(d-Arg) (SEQ ID NO:80).

2. The peptide or peptidomimetic sequence of claim 1, wherein a d-residue is substituted with an 1-residue.

3. The peptide or peptidomimetic sequence of claim 1 wherein the sequence inhibits proliferation of a cell.

4. The peptide or peptidomimetic sequence of claim 1 wherein the sequence abrogates cell cycle G2 checkpoint of a cell.

5. The peptide or peptidomimetic sequence of claim 1 wherein the sequence has a length from about 6 to about 12, 10 to about 20, 18 to about 25, 25 to about 100, 25 to about 200, or 50 to about 300 residues in length.

6. A composition comprising the peptide or peptidomimetic sequence of claim 1 and a nucleic acid damaging agent.

7. A composition comprising the peptide or peptidomimetic sequence of claim 1 and an anti-proliferative agent.

8. A pharmaceutical composition comprising the peptide or peptidomimetic sequence of claim 1.

9. A pharmaceutical composition comprising the peptide or peptidomimetic sequence of claim 1 and a nucleic acid damaging agent or an anti-proliferative agent.

10. A kit comprising the peptide or peptidomimetic sequence of claim 1 and instructions for use.

11. The kit of claim 10, wherein the instructions for use include instructions for inhibiting cell proliferation in combination with a nucleic acid damaging treatment.

12. The kit of claim 10, further comprising a nucleic acid damaging agent.

13. The kit of claim 10, further comprising an anti-proliferative agent.

14. A method of inhibiting proliferation of a cell, comprising contacting a cell with an amount of a peptide or peptidomimetic of claim 1 sufficient to inhibit proliferation of the cell.

15. The method of claim 14, further comprising contacting the cell with a nucleic acid damaging agent or exposing the cell to a nucleic acid damaging treatment.

16. The method of claim 15, wherein the cell is a cultured cell, or is present in a subject.

17. A method of increasing sensitivity of a cell to a nucleic acid damaging agent or treatment, comprising contacting the cell with an amount of a peptide or peptidomimetic of claim 1 sufficient to increase sensitivity of the cell to a nucleic acid damaging agent or treatment.

18. The method of claim 17, further comprising contacting the cell with a nucleic acid damaging agent or exposing the cell to a nucleic acid damaging treatment.

19. The method of claim 32, wherein the cell is a cultured cell, or is present in a subject.

20. A method of increasing nucleic acid damage to a cell, comprising contacting a cell with an amount of a peptide or peptidomimetic of claim 1 sufficient to increase nucleic acid damage of the cell.

21. The method of claim 20, further comprising contacting the cell with a nucleic acid damaging agent or exposing the cell to a nucleic acid damaging treatment.

22. The method of claim 20, wherein the cell is a cultured cell, or is present in a subject.

23. A method of treating a cell proliferative disorder, comprising administering to a subject having or at risk of having a cell proliferative disorder an amount of peptide or peptidomimetic of claim 1 effective to treat the cell proliferative disorder.

24. The method of claim 23, wherein at least a part of the cells comprising the cell proliferative disorder is located in blood, breast, lung, thyroid, head or neck, brain, lymph, gastrointestinal tract, nasopharynx, genito-urinary tract, bladder, kidney, pancreas, liver, bone, muscle, or skin.

25. The method of claim 23, wherein the peptide or peptidomimetic is administered locally, regionally or systemically.

26. The method of claim 23, wherein the cell proliferative disorder comprises a benign or malignant solid or liquid tumor.

27. The method of claim 26, wherein the tumor is metastatic or non-metatstaic.

28. The method of claim 26, wherein the solid tumor comprises a sarcoma or carcinoma.

29. The method of claim 26, wherein the liquid tumor comprises a hematopoietic cancer.

30. The method of claim 29, wherein the hematopoietic cancer comprises a myeloma, lymphoma or leukemia.

31. The method of claim 26, wherein the treatment results in improving the subjects condition.

32. The method of claim 31, wherein the improvement comprises decreased cell proliferation, decreased numbers of cells, inhibiting increased cell proliferation, inhibiting increases in numbers of cells, increased apoptosis, or decreased survival, of at least a portion of the cells comprising the cell proliferative disorder.

33. The method of claim 29, further comprising administering a nucleic acid damaging agent, a nucleic acid damaging treatment, an anti-proliferative agent, or an anti-proliferative treatment to the subject.

34. The method of claim 33, wherein the agent or treatment comprises a drug, radiation, a radioisotope, environmental shock.

35. The method of claim 34, wherein the drug comprises a chemotherapeutic drug.

36. The method of claim 34, wherein the drug comprises 5-fluorouracil (5-FU), rebeccamycin, adriamycin (ADR), bleomycin (Bleo), pepleomycin, a cisplatin derivative, or camptotecin (CPT).

37. The method of claim 36, wherein the cisplatin derivative comprises cisplatin (CDDP) or oxaliplatin.

38. The method of claim 34, wherein the radioisotope comprises $I^{131}$, $I^{125}$, $^{90}Y$, $^{177}Lu$, $^{213}Bi$, or $^{211}At$.

39. The method of claim 34, wherein the radiation comprises UV radiation, IR radiation, or alpha-, beta- or gamma-radiation.

40. The method of claim 34, wherein the environmental shock comprises hyperthermia.

* * * * *

UNITED STATES PATENT AND TRADEMARK OFFICE
CERTIFICATE OF CORRECTION

PATENT NO.       : 6,995,135 B2
APPLICATION NO.  : 10/347145
DATED            : February 7, 2006
INVENTOR(S)      : Kawabe et al.

It is certified that error appears in the above-identified patent and that said Letters Patent is hereby corrected as shown below:

Col. 227, lines 39-40
replace "(d-Bpa)(d-(Ser)(d-Trp)(d-Phe-2,3,4,5,6-F)"
 with --(d-Bpa)(d-Ser)(d-Trp)(d-Ser)(d-Phe-2,3,4,5,6-F)--.

Signed and Sealed this

First Day of August, 2006

JON W. DUDAS
*Director of the United States Patent and Trademark Office*